(12) United States Patent
Benning et al.

(10) Patent No.: US 9,062,331 B2
(45) Date of Patent: Jun. 23, 2015

(54) ENZYME DIRECTED OIL BIOSYNTHESIS IN MICROALGAE

(71) Applicant: Board of Trustees of Michigan State University, East Lansing, MI (US)

(72) Inventors: Christoph Benning, East Lansing, MI (US); Rachel Miller, Holt, MI (US); Eric R. Moellering, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 218 days.

(21) Appl. No.: 13/719,868

(22) Filed: Dec. 19, 2012

(65) Prior Publication Data
US 2013/0212736 A1   Aug. 15, 2013

(51) Int. Cl.
| C12N 15/82 | (2006.01) |
| C07H 21/04 | (2006.01) |
| C12P 7/64  | (2006.01) |
| C12N 9/10  | (2006.01) |
| C12N 15/79 | (2006.01) |

(52) U.S. Cl.
CPC ............. C12P 7/6463 (2013.01); C12N 9/1029 (2013.01); C12N 15/8247 (2013.01); C12N 15/79 (2013.01)

(58) Field of Classification Search
None
See application file for complete search history.

(56) References Cited

U.S. PATENT DOCUMENTS

| 4,683,195 A | 7/1987 | Mullis et al. |
| 4,683,202 A | 7/1987 | Mullis |
| 4,695,411 A | 9/1987 | Stern et al. |
| 4,940,838 A | 7/1990 | Schilperoort et al. |
| 4,945,050 A | 7/1990 | Sanford et al. |
| 4,965,188 A | 10/1990 | Mullis et al. |
| 4,981,785 A | 1/1991 | Nayak |
| 5,057,422 A | 10/1991 | Bol et al. |
| 5,173,410 A | 12/1992 | Ahlquist |
| 5,187,267 A | 2/1993 | Comai et al. |
| 5,352,605 A | 10/1994 | Fraley et al. |
| 5,358,691 A | 10/1994 | Clark et al. |
| 5,451,513 A | 9/1995 | Maliga et al. |
| 5,500,360 A | 3/1996 | Ahlquist et al. |
| 5,501,967 A | 3/1996 | Offringa et al. |
| 5,538,848 A | 7/1996 | Livak et al. |
| 5,545,817 A | 8/1996 | McBride et al. |
| 5,545,818 A | 8/1996 | McBride et al. |
| 5,584,807 A | 12/1996 | McCabe |
| 5,599,677 A | 2/1997 | Dowell et al. |
| 5,639,606 A | 6/1997 | Willey |
| 5,643,765 A | 7/1997 | Willey |
| 5,672,480 A | 9/1997 | Dowell et al. |
| 5,824,877 A | 10/1998 | Hinchee et al. |
| 5,846,717 A | 12/1998 | Brow et al. |
| 5,846,795 A | 12/1998 | Ahlquist et al. |
| 5,866,330 A | 2/1999 | Kinzler et al. |
| 5,866,785 A | 2/1999 | Donson et al. |
| 5,876,978 A | 3/1999 | Willey et al. |
| 5,885,530 A | 3/1999 | Babson et al. |
| 5,965,794 A | 10/1999 | Turpen |
| 5,977,438 A | 11/1999 | Turpen et al. |
| 5,981,839 A | 11/1999 | Knauf et al. |
| 5,981,840 A | 11/1999 | Zhao et al. |
| 5,985,557 A | 11/1999 | Prudent et al. |
| 5,994,069 A | 11/1999 | Hall et al. |
| 6,001,567 A | 12/1999 | Brow et al. |
| 6,051,757 A | 4/2000 | Barton et al. |
| 6,090,543 A | 7/2000 | Prudent et al. |
| 6,159,750 A | 12/2000 | Edmonds |
| 7,122,367 B2 | 10/2006 | Milcamps et al. |
| 7,429,473 B2 | 9/2008 | Milcamps et al. |
| 7,511,189 B2 | 3/2009 | Zou et al. |
| 8,362,318 B2 | 1/2013 | Benning et al. |
| 2007/0028329 A1 | 2/2007 | Milcamps et al. |
| 2007/0204370 A1 | 8/2007 | Mietkiewska et al. |
| 2007/0231819 A1 | 10/2007 | Lawrence et al. |
| 2010/0317073 A1 | 12/2010 | Sayre et al. |
| 2011/0061130 A1 | 3/2011 | Zou et al. |
| 2013/0116462 A1 | 5/2013 | Durrett et al. |

FOREIGN PATENT DOCUMENTS

| DE | 4317414 C1 | 4/1994 |
| EP | 0292435 A1 | 11/1988 |
| EP | 0332581 A2 | 9/1989 |
| WO | WO-93/07278 A1 | 4/1993 |
| WO | WO-93/18176 A1 | 9/1993 |
| WO | WO-94/13822 A2 | 6/1994 |

(Continued)

OTHER PUBLICATIONS

"International Application Serial No. PCT/US2010/062407, International Preliminary Report on Patentability dated Jul. 4, 2012", 7 pgs.
"International Application Serial No. PCT/US2010/062407, International Search Report mailed Aug. 2, 2011", 5 pgs.
"International Application Serial No. PCT/US2010/062407, Invitation to pay additional fees mailed Jun. 6, 2011", 2 pgs.
"International Application Serial No. PCT/US2010/062407, Written Opinion mailed Aug. 2, 2011", 6 pgs.
"UniProt Direct Submission. B9SSQ4_RICCO", [online]. © 2002-2012 UniProt Consortium [retrieved on Jun. 27, 2012]. Retrieved from the Internet: <URL: http://www.uniprot.org/uniproVB9SSQ4>, (Apr. 18, 2012), 3 pgs.
"UniProt Direct Submission. D6NSS8_EUOAL", [online]. © 2002-2012 UniProt Consortium [retrieved on Jun. 27, 2012]. Retrieved from the Internet: <URL: http://www.uniprot.org/uniproVD6NSS8>, (Nov. 16, 2011), 3 pgs.
Burgal, J., et al., "Metabolic engineering of hydroxy fatty acid production in plants: RcDGAT2 drives dramatic increases in ricinoleate levels in seed oil", *Plant Biotechnplogy Journal*, 6(8), (2008), 819-831.

(Continued)

*Primary Examiner* — Eileen B O Hara
(74) *Attorney, Agent, or Firm* — Schwegman Lundberg & Woessner, P.A.

(57) ABSTRACT

The present invention is related to biosynthetic oil compositions and methods of making thereof. In some embodiments, the invention relates to the use of endogenous enzymes in plants capable of synthesizing oil. In preferred embodiments, said plants are algae. In further embodiments, said algae are from the family *Chlamydomonas, Nannochloropsis, Dunaliella, Chiarella* and *Scenedesmus*. In still further embodiments, said endogenous enzymes are diacylglycerol acyltransferases.

17 Claims, 18 Drawing Sheets

(56) References Cited

FOREIGN PATENT DOCUMENTS

| | | |
|---|---|---|
| WO | WO-95/14098 A1 | 5/1995 |
| WO | WO-95/16783 A1 | 6/1995 |
| WO | WO-2011/082253 A2 | 7/2011 |

OTHER PUBLICATIONS

Chen, Q., "Biosynthesis of Phytosterol Esters: Identification of a Sterol O-Acyltransferase in *Arabidopsis*", *Plant Physiol.*, 145, (2007), 974-984.

Datta, S. K., et al., "Genetically Engineered Fertile Indica-Rice Recovered from Protoplasts", *Nat. Biotechnol.* 8(8), (1990), 736-740.

Dehesh, K., et al., "Production of high levels of 8:0 and 10:0 fatty acids in transgenic canola by overexpression of Ch FatB2, a thioesterase cDNA from *Cuphea hookeriana*", *The Plant Journal*, 9(2), (1996), 167-172.

Dehesh, K., et al., "Two Novel Thioesterases are Key Determinants Distribution of the Bimodal Distribution of Acyl Chain Length of *Cuphea palustris* Seed Oil", *Plant Physiology*, 110(1), (1996), 203-210.

Durrett, T. P, et al., "A distinct DGAT with *sn*-3 acetyltransferaseactivity that synthesizes unusual, reduced-viscosity oils in *Euonytnus* and transgenic seeds" *Proc. Natl. Acad. Sci. USA.*, 107(20), (May 18, 2010), 9464-9469.

Durrett, T. P., et al., "Plant triacylglycerols as feedstocks for the production of biofuels", *The Plant Journal*, 54(4), (2008), 593-607.

Kalscheuer, R., et al., "A Novel Bifunctional Wax Ester Synthase/Acyl-CoA:Diacylglycerol Acyltransferase Mediates Wax Ester and Triacylglycerol Biosynthesis in *Acinetobacter calcoaceticus* ADPT", *J. Biol. Chem.*, 278(10), (2003), 8075-8082.

King, A., "Cuticular wax biosynthesis in petunia petals: cloning and characterization of an alcohol-acyltransferase that synthesizes waxesters", *Planta*, 226(2), (2007), 381-394.

Knothe, G., et al., "Kinematic viscosity of biodiesel fuel components and related compounds. Influence of compound structure and comparison to petrodiesel fuel components", *Fuel*, 84(9), (Jun. 2005), 1059-1065.

Kroon, J. T., et al., "Identification and functional expression of a type 2 acyl-CoA:diacylglycerol acyltransferase (DGAT2) in developing castor bean seeds which has high homology to the major triglyceride biosynthetic enzyme of fungi and animals", *Phytochemistry*, 67(23), (2006), 2541-2549.

Kunst, L., et al., "Fatty acid elongation in developing seeds of *Arabidopsis thaliana*", *Plant Physiol. Biochem.*, 30(4), (1992), 425-434.

Lardizabal, K. D., et al., "Purification of a Jojoba Embryo Wax Synthase, Cloning of its cDNA, and Production of High Levels of Wax in Seeds of Transgenic *Arabidopsis*", *Plant Physiol.*, 122(3), (2000), 645-655.

Li, F., et al., "Identification of the Wax Ester Synthase/Acyl-Coenzyme A:Diacylglycerol in Acyltransferase WSD1 Required for Stem Wax Ester Biosynthesis in *Arabidopsis*", *Plant Physiology*, 148(1), (2008), 97-107

Mietiewska, E., et al., "Seed-Specific Heterologous Expression of a Nasturtium *FAE* Gene in *Arabidopsis* Results in a DramaticIncrease in the Proportion of Erucic Acid", *Plant Physiol.*, 136(1), (2004), 2665-2675.

Millar, A. A., et al., "Very-long-chain fatty acid biosynthesis is controlled through the expression and specificity of the condensing enzyme", *Plant J.*, 12(1), (1997), 121-131.

Pillai, M. G., et al., "Biosynthesis of Triacylglycerol Molecular Species in an Oleaginous Fungus, *Modierella ramanniona var. angulispora*", *J. Biochem*, 132(1), (2002), 121-126.

Routaboul, J. M., et al., "The *TAG1* locus of *Arabidopsis* encodes for a diacylglycerol acyltransferase", *Plant Physiol. Bioch.*, 37(11), (1999), 831-840.

Saha, S., et al., "Cytosolic Triacylglycerol Biosynthetic Pathway in Oilseeds. Molecular Cloning and Expression of Peanut Cytosolic Diacylglycerol Acyltransferase", *Plant Physiology*, 141(4), (2006), 1533-1543.

Smith, S. J., "Obesity resistance and multiple mechanisms of triglyceride synthesis in mice lacking Dgat", *Nat. Genet.*, 25(1), (2000), 87-90.

Stone, S. J., "Lipopenia and Skin Barrier Abnormalities in DGAT2-deficient Mice", *J. Biol. Chem.*, 279(12), (2004), 11767-11776.

Wang, N., et al., "Assessment of FAE1 polymorphisms in three *Brassica* species using EcoTILLING and their association with differences in seed erucic acid content", *BMC Plant Biology*, 10: 137, (2010), 1-11.

Weising, K., et al., "Foreign Genes in Plants: Transfer, Structure, Expression and Applications", *Annu. Rev. Genet.* 22, (1988), 421-477.

Yen, C.-L. E., et al., "Thematic Review Series: Glycerolipids. DGAT enzymes and triacylglycerol biosynthesis", *J. Lipid Res.*, 49, (2008), 2283-2301.

Zhang, M., et al., "*DGAT1* and *PDAT1* Acyltransferases Have Overlapping Functions in *Arabidopsis* Triacylglycerol Biosynthesis and Are Essential for Normal Pollen and Seed Development", *Plant Cell*, 21(12), (2009), 3885-3901.

Zou, J., et al., "Modification of Seed Oil Content and Acyl Composition in the *Brassicaceae* by Expression of a Yeast *sn*-2 Acyltransferase Gene", *Plant Cell*, 9(6), (1997), 909-923.

"U.S. Appl. No. 12/639,304, Notice of Allowance mailed Sep. 18, 2012", 8 pgs.

"U.S. Appl. No. 12/639,304, Interview Summary mailed Sep. 18, 2012", 1 pg.

"U.S. Appl. No. 12/639,304, Non-Final Office Action mailed Mar. 15, 2012", 15 pgs.

"U.S. Appl. No. 12/639,304, Response filed Jan. 31, 2012 to Restriction Requirement mailed Jan. 3, 2012", 4 pgs.

"U.S. Appl. No. 12/639,304, Response filed Jun. 5, 2012 to Non-Final Office Action mailed Mar. 15, 2012", 13 pgs.

"U.S. Appl. No. 12/639,304, Restriction Requirement mailed Jan. 3, 2012", 6 pgs.

Adams, M. D., et al., "Rapid cDNA sequencing(expressed sequence tags) from a directionally cloned human infant brain cDNA library", *Nat. Genet.*, 4(4), (1993), 373-380.

Ballas, N. et al., "Efficient functioning of plant promoters and poly(A) sites in *Xenopus* oocytes.", *Nucleic Acids Res.*, 17(19), (1989), 7891-7903.

Baud, S., et al., "An integrated overview of seed development in *Arabidopsis thaliana* ecotype WS", *Plant Physiol. Biochem.*, 40(2). (2002), 151-160.

Bauer, D., et al., "Identification of differentially expressed mRNA species by an Improved display technique (DDRT-PCR)", *Nucleic Acids Res.*, 21(18), (1993), 4272-4280.

Beachy, R. N., et al., "Accumulation and assembly of soybean β-conglycinin in seeds of transformed petunia plants", *EMBO J.*, 4(12), (1985), 3047-3053.

Bertioli, D. J., et al., "An analysis of differential display shows a strong bias towards high copy number mRNAs", *Nucleic Acids Res.* 23(21), (1995), 4520-4523.

Bevan, M., et al., "A chimaeric antibiotic resistance gene as a selectable marker for plant cell transformation", *Nature*, 304, (1983), 184-187.

Bligh, E. G., et al., "A Rapid Method of Total Lipid Extraction and Purification", *Canadian Journal of Biochemistry and Physiology*, 37(8), (1959), 911-917.

Blochlinger, K., et al., "Hygromycin B Phosphotransferase as a Selectable Marker for DNA Transfer Experiments with Higher Eucaryotic Cells", *Mol. Cell. Biol.*, 4(12), (1984), 2929-2931.

Bourouis, M., et al., "Vectors containing a prokaryotic dihydrofolate reductase gene transform *Drosophila* cells to methotrexate-resistance", *The EMBO Journal*, 2(7), (1983), 1099-1104.

Bouvier-Nave, P., et al., "Expression in Yeast and Tobacco of Plant cDNAs Encoding Acyl CoA Diacylglycerol Acyltransferase", *Eur. J. Biochem.* 267(1), (2000), 85-96.

Callis, J., et al., "Introns Increase Gene Expression in Cultured Maize Cells", *Genes and Development*, 1(10), (1987), 1183-1200.

Casas, A. M., et al., "Transgenic sorghum plants via microprojectile bombardment", *Proc. Natl. Acad. Sci. USA*, 90(23), (1993), 11212-11216.

(56) References Cited

OTHER PUBLICATIONS

Chamberlin, M., et al., "New RNA polymerase from *Escherichia coli* infected with Bacteriophage T7", *Nature*, 228(5268), (1970), 227-231.

Chao, W. S., et al., "Leucine Aminopeptidase RNAs, Proteins, and Activities Increase in Response to Water Deficit, Salinity, and the Wound Signals Systemin, Methyl Jasmonate, and Abscisic Acid. ", *Plant Physiol*, 120(4), (1999), 979-992.

Christou, P., et al., "Production of Transgenic Rice (*Oryza sativa* L.) Plants from Agronomically Important Indica and Japonica Varieties via Electric Discharge Particle Acceleration of Exogenous DNA into Immature Zygotic Embryos", *Nature Biotechnology*, 9, (1991), 957-962.

Christou, P., et al., "Stable Transformation of Soybean Callus by DNA-Coated Gold Particles", *Plant Physiol.*, 87(3), (1988), 671-674.

Crossway, A., et al., "Integration of foreign DNA following microinject of tobacco mesophyll protoplasts", *Mol. Gen. Genet.*, 202 (2), (1986), 179-185.

Crossway, A., et al., "Micromanipulation Techniques in Plant Biotechnology", *BioTechniques*, 4(4), (1986), 320-334.

Dahlqvist, A., et al., "Phospholipid diacylglycerol acyltransferase: An enzyme that catalyzes the acyl-CoA-independent formation of triacylglycerol in yeast and plants", *Proc. Natl. Acad. Sci. USA.* 97(12), (2000), 6487-6492.

Dana, S. K., et al., "Genetically Engineered Fertile Indica-Rice Recovered from Protoplasts", *Nat. Biotechnol.* 8(8), (1990), 736-740.

Derisi, J., et al., "Use of a cDNA microarray to analyse gene expression patters in human cancer", *Nature Genetics*, vol. 14, (Dec. 1996), 457-460.

Dyer, J. D., et al., "Development and potential of genetically engineered oilseeds", *Seed Sci. Res.*, 15, (2005), 225-267.

Fraley, R. T., et al., "Liposome-mediated delivery of tobacco mosaic virus RNA into tobacco protoplasts: A sensitive assay for monitoring lipolipo-some-protoplast interactions", *Proc. Natl. Acad. Sci., USA*, 79, (1982), 1859-1863.

Fromm, M. E., et al., "Expression of genes transferred into monocot and dicot plant cells by electroporation", *Proc. Natl. Acad. Sci. USA*, 82, (1985), 5824-5828.

Fromm, M. E., et al., "Inheritance and Expression of Chimeric Genes in the Progeny of Transgenic Maize Plants", *Nature Biotechnology*, 8(9), (1990), 833-839.

Garbarino, J. E., et al., "Isolation of a ubiquitin-ribosomal protein gene(ubi3) from potato and expression of its promoter in transgenic plants.", *Plant Mol. Biol.*, 24(1), (1994), 119-127.

Gordon-Kamm, W. J., et al., "Transformation of Maize Cells and Regeneration of Fertile Transgenic Plants", *The Plant Cell*, 2(7), (1990), 603-618.

Guerineau, F., et al., "Effect of deletions in the cauliflower mosaic virus polyadenylation sequence on the choice of the polyadenylation sites in tobacco protoplasts.", *Mol. Gen. Genet.*, 262(1-2), (1991), 141-144.

Habu, Y., et al., "Amplified Restriction Fragment Length Polymorphism-based mRNA Fingerprinting Using a Single Restriction Enzyme That Recognizes a 4-bp Sequence", *Biochem Biophys Res Commun.*, 234(2), (1997), 516-521.

Hayashimoto, A., et al., "A Polyethylene Glycol-Mediated Protoplast Transformation System for Production of Fertile Transgenic Rice Plants.", *Plant Physiol.*, 93(3), (1990), 857-863.

He, X., et al., "Cloning and Characterization of a cDNA Encoding Diacylglycerol Acyltransferase from Castor Bean", *Lipids*, 39(4), (2004), 311-318.

He, X., et al., "Regulation of Diacylglycerol Acyltransferase in Developing Seeds of Castor", *Lipids*, 39(9), (2004), 865-871.

Hedrick, S. M., et al., "Sequence Relationships Between Putative T-cell Receptor Polypeptides and Immunoglobulins". *Nature*, 308(5955), (1984), 153-158.

Hill, M., et al., "Biolistic introduction of a synthetic *Bt* gene into elite maize.", *Euphytica*, 85(1-3),(1995), 119-123.

Hinchee, M. A., et al., "Production of Transgenic Soybean Plants Using Agrobacterium-Mediated DNA Transfer", *Nature Biotechnology*, 6, (1988), 915-922.

Hobbs, D. H., et al., "Cloning of a cDNA encoding diacylglycerol acyltransferase from *Arabidopsis thaliana* and its functional expression", *FEBS Lett.*, 452(3), (1999), 145-149.

Ichihara, K., et al., "Diacylglycerol Acyltransferase in Maturing Safflower Seeds: Its Influences on the Fatty Acid Composition of Triacylglycerol and on the Rate of Triacylglycerol Synthesis", *Biochem Biophys. Acta*, 958(1), (1998), 125-129.

Ishida, Y., et al., "High efficiency transformation of maize (*Zea mays* L.) mediated by *Agrobacterium ttirnefaciens*", *Nature Biotechnology*, 14(6), (1996), 745-750.

Ito, T., et al., "Fluorescent Differential Display Arbitrarily Primed RT-PCR Fingerprinting on an Automated DNA Sequencer", *FEBS Lett.*, 351(2), (1994), 231-236.

J. Sambrook, et al., *Molecular Cloning: A Laboratory Manual*, 2nd Ed., Cold Spring Harbor Laboratory Press, NY, (1989), pp. 16.6-16.8.

J. Sambrook, et al., *Molecular Cloning: A Laboratory Manual*, Cold Spring Harbor Press, NY, (1989), pp. 9.31-9.58.

J. Sambrook, et al., *Molecular Cloning: A Laboratory Manual*, Cold Spring Harbor Press, NY, (1989), pp. 7.39-7.52.

Jahne, A., et al., "Regeneration of Transgenic, Microspore-Derived, Fertile Barley", *Theor. Appl. Genet.*, 89(4), (1994), 525-533.

Jako, C, et al., "Seed-Specific Over-Expression of an *Arabidopsis* CDNA Encoding a Diacylglycerol Acyltransferase Enhances Seed Oil Content and Seed Weight", *Plant Physiology*, 126(2), (2001), 861-874.

Jaworski, J., et al., "Industrial Oils from Transgenic Plants", *Curr. Opin. Plant Biol.*, 6(2), (2003), 178-184.

Joshi, C. P., et al., "Putative polyadenylation signals in nuclear genes of higher plants: a compilation and analysis", *Nucleic Acid Res.*, 15(23), (1987), 9627-9640.

Kacian, D. L., et al., "A Replicating RNA Molecule Suitable for a Detailed Analysis of Extracellular Evolution and Replication", *Proc. Natl. Acad. Sci. USA*, 69(10), (1972), 3038-3042.

Katavic, V., et al,, "Alteration of Seed Fatty Acid Composition by an Ethyl Methanesulfonate-Induced Mutation in *Arabidopsis Thaliana* Affecting Diacylglycerol Acyltransferase Activity", *Plant Physiol.*, 108(1), (1995), 399-409.

Kennedy, E. P., "Biosynthesis of Complex Lipids", *Fed. Proc.*, 20, (1961), 934-940.

Klaus, D., et al., "Increased fatty acid production in potato by engineering of acetyl-CoA carboxylase", *Planta*. 219, (2004), 389-396.

Klein, T. M., et al., "Factors Influencing Gene Delivery into *Zea mays* Cells by High Velocity Microprojectiles", *Nature Biotechnology*, 6(5), (1988), 559-563.

Klein, T. M., et al., "Genetic Transformation of Maize Cells by Particle Bombardment", *Plant Physiology*, 91(1), (1989), 440-444.

Klein, T. M., et al., "Transfer of Foreign Genes into Intact Maize Cells with High-Velocity Microprojectiles", *Proc. Nat. Acad. Sci. USA*, 85, (1988), 4305-4309.

Knudsen, S., et al., "Transformation of the developing barley endosperm by particle bombardment". *Planta*. 185, (1991), 330-336.

Koziel, M. G., et al., "Field Performance of Elite Transgenic Maize Plants Expressing an Insecticidal Protein Derived from *Bacillus thuringlensis*", *Nature Biotechnology*, 11, (1993), 194-200.

Koziel, M. G., et al., "Transgenic Maize for the Control of European Corn Borer and Other Maize Insect Pests", *Ann. N Y Acad. Sci.* 792(1), (1996), 164-171.

Krens, F. A., et al., "In vitro transformation of plant protoplasts with Ti-plasmid DNA.", *Nature*, 296, (1982), 72-74.

Lardizabal, K. D., et al., "DGAT1 is a new Diacylglycerol Acyltransferase Gene Family—Purification, Cloning and Expression in Insect Cells of two Polypeptides from Mortierella Ramanniana with Diacylglycerol Acyltransferase Activity", *J. Biol. Chem.*. 276(42), (2001), 38862-38869.

Liang, P., et al., "Differential Display of Eukaryotic Messenger RNA by Means of the Polymerase Chain Reaction", *Science*, 257(5072), (1992), 967-971.

(56) References Cited

OTHER PUBLICATIONS

Liang, P., et al., "Distribution and cloning of eukaryotic mRNAs by means of differential display: refinements and optimization", *Nucleic Acids Research*, 21(14), (1993), 3269-3275.

Maniatis, T., et al., "Regulation of Inducible and Tissue-Specific Gene Expression", *Science*, 236(4806), (1987), 1237-1245.

McCabe, D. E., et al., "Stable Transformation of Soybean (*Glycine max*) by Particle Acceleration", *Nature Biotechnology*, 6, (1988), 923-926.

Milcamps, A., et al., "isolation of a Gene-Encoding a1,2 Diacylglycerol-sn-Acetyl-CoA Acetyltransferase from Developing Seeds of *Euonytnus alatus*", *J. Biol. Chem*. 280, (2005), 5370-5377.

Mogen, B. D., et al., "Upstream sequences other than AAUAAA are required for efficient messenger RNA 3'-end formation in plants.", *The Plant Cell*, 2(12), (1990), 1261-1272.

Munroe, D., et al., "Tales of poly(A): a review", *Gene*, 91(2), (1990), 151-158.

Murphy, D. J., "Production of novel oils in plants", *Curr Opin Biotechnol.*, 10, (1999), 175-180.

Nehra, N. S., et al., "Self-fertile transgenic wheat plants regenerated from isolated scutellar tissues following microprojectile bombardment with two distinct gene constructs", *The Plant Journal*, 5(2), (1994), 285-297.

Nykiforuk, C. L., et al., "Characterization of cDNAs encoding diacylglycerol acyltransferase from cultures of *Brassica napus* and sucrose-mediated induction of enzyme biosynthesis", *Biochem. Biophys Acta*, 1580(2-3), (2002), 95-109.

Odell, J., et al., "Identification of DNA Sequences Required for Activity of the Cauliflower Mosaic Virus 35S Promoter", *Nature*, 313, (1985), 810-812.

Ohlrogge, J., et al., "Lipid Biosynthesis", *The Plant Cell*, 7(7), (1995), 957-970.

Okubo, K., et al., "Large Scale cDNA Sequencing for Analysis of Quantitative and Qualitiative Aspects of Gene Expression", *Nat. Genet.*, 2(3), (1992), 173-179.

Paszkowski, J., et al., "Direct Gene Transfer to Plants", *The EMBO Journal*, 3(12), (1984), 2717-2722.

Proudfoot, N. J., "Poly(A)signals", *Cell*, 64, (1991), 671-674.

Riggs, C. D., et al., "Stable transformation of tobacco by electroporation: evidence for plasmid concatenation", *Proc. Natl. Acad. Sci. USA*, 83(15), (1986), 5602-5606.

Rosenberg, A. H., et al., "Vectors for selective expression of cloned DNAs by T7 RNA Polymerase", *Gene*, 56(1), (1987), 125-135.

Routaboul, C, et al., "Proposal for a new UVA protection factor: use of an in vitro model of immediate pigment darkening.", *European Journal of Dermatology*, 12(5), (Sep.-Oct. 2002), 439-44.

Sandager, L. et al., "Storage Lipid Synthesis Is Non-essential in Yeast", *J. of Biological Chem.*, 277, (2002), 6478-6482.

Sanfacon, H., et al., "A dissection of the cauliflower mosaic virus polyadenylation signal", *Genes Dev.*, 5, (1991), 141-149.

Sanford, J. C., et al., "Delivery of Substances into Cells and Tissues Using a Particle Bombardment Process", *Particulate Sci. Technol.*, 5, (1987), 27-37.

Schell, J., "Transgenic Plants as Tools to Study the Molecular Organization of Plant Genes", *Science*, 237(4819), (1987), 1176-1183.

Schena, M., "Quantitative Monitoring of Gene Expression Patterns with a Complementary DNA Microarray", *Science*, 270(5235), (1995), 467-470.

Shanklin, J., et al., "Desaturation and Related Modifications of Fatty Acids", Annual *Review Plant Physiol. Plant Mol. Biol.*, 49, (1998), 611-641.

Shimamoto, K., et al., "Fertile transgenic rice plants regenerated from transformed protoplasts", *Nature*, 338, (1989), 274-276.

Shimkets, R. A., et al., "Gene Expression Analysis by Transcript Profiling Coupled to a Gene Database Query", *Nat.Biotechnol.* 17(8), (1999), 798-803.

Shockey, J. M., et al., "Tung Tree DGAT1 and DGAT2 Have Nonredunclant Functions in Triacylglycerol Biosynthesis and Are Localized to Different Subdomains of the Endoplasmic Reticulum", *The Plant Cell*, 18(9), (2006), 2294-2313.

Singh, S. P., et al., "Metabolic Engineering of New Fatty Acids in Plants", *Cur Opin. Plant Biol.*, 8(2), (2005), 197-203.

Somers, D. A., et al., "Fertile, Transgenic Oat Plants." *Nature Biotechnology*, 10, (1992), 1589-1594.

Song, K., et al., "A Method for Examining Expression of Homologous Genes in Plant Polyploids", *Plant Mol Biol.* 26(4), (1994), 1065-1071.

Spencer, T. M., et al., "Bialaphos selection of stable tranformants from maize cell culture", *TAG Theoretical and Applied Genetics* 79(5), (1990), 625-631.

Stahl, U., et al., "Cloning and Functional Characterization of a Phospholipid Diacylglycerol Acyltransferase from *Arabidopsis*". *Plant Physiol*. 135, (2004), 1324-1335.

Staub, J. M., et al., "Accumulation of D1 polypeptide in tobacco plastids is regulated via the untranslated region of the psbA mRNA.", *EMBO J.*, 12(2), (1993), 601-606.

Staub, J. M., et al., "Long Regions of Homologous DNA are Incorporated into the Tobacco Plastid Genome by Transformation.", *The Plant Cell*, 4(1), (1992), 4-39.

Stone, B., et al., "Targeted RNA fingerprinting: the cloning of differentially-expressed cDNA fragments enriched for members of the zinc finger gene family", *Nucleic Acids Res*. 22(13), (1994), 2612-2618.

Svab, Z., et al., "High-frequency plastid transformation in tobacco by selection for a chimeric aadA gene", *Proc. Natl. Acad. Sci. USA*, 90(3), (1993), 913-917.

Svab, Z., et al., "Stable transformation of plastids in higher plants". *Proc. Natl. Acad. Sci. USA*, 87, (1990), 8528-8530.

Thelen, J J., et al., "Metabolic Engineering of Fatty Acid Biosynthesis in Plants.", *Metabolic Engineering*, 4(1), (2002), 12-21.

Torbert, K. A., et al., "Use of paromomycin as a selective agent for oat transformation", *Plant Cell Reports*, 14, (1995), 635-640.

Umbeck, P., et al., "Genetically transformed cotton (*Gossypiurn hirsutum* L.) plants.", *Nature Biotechnology*, 5, (1987), 263-266.

Vasil, V., et al., "Rapid Production of Transgenic Wheat Plants by Direct Bombardment of Cultured immature Embryos", *Nature Biotechnology*, 11, (1993), 1553-1558.

Velculescu, V. E., et al., "Serial Analysis of Gene Expression", *Science*, 270(5235), (1995), 484-487.

Vieira, J., et al., "The pUC plasmids, an M13mp7-derived system for insertion mutagenesis and sequencing with synthetic universal primers", *Gene* 19(3), (1982), 259-268.

Vogel, G., et al., "Cholinephosphotransferase and Diacylglycerol Acyltransferase—Substrate Specificities at a Key Branchpoint in Seed Lipid Metabolism", *Plant Physiol*, 110, (1996), 923-931.

Voss, S. D., et al., "The Role of Enhancers in the Regulation of Cell-Type-Specific Transcriptional Control", *Trends Biochem. Sci.*, 11, (1986), 287-289.

Wan, Y., et al., "Generation of Large Numbers of Independently Transformed Fertile Barley Plants", *Plant Physiol.*, 104, (1994), 37-48.

Wang, X., et al., "Direct Sequencing of DNA Isolated from mRNA Differential Display", *Biotechniques* 18(3), (1995), 448-453.

Weeks, J. T., et al., "Rapid Production of Multiple Independent Lines of Fertile Transgenic Wheat (*Triticum aestivum*)", *Plant Physiol.*, 102, (1993), 1077-1084.

Weisinger, K., et al., "Foreign Genes in Plants: Transfer, Structure, Expression and Applications", *Annu. Rev. Genet*. 22, (1988), 421-477.

White, J., et al., "A cassette containing the bar gene of Streptomyces hygroscopicus: a selectable marker for plant transformation", *Nucleic Acids Research*, 18(4), (1990), 1062.

Wu, D. Y., et al., "The Ligation Amplification Reaction (LAR)—Amplification of Specific DNA Sequences Using Sequential Rounds of Template-Dependent Ligation", *Genomics*, 4(4), (1989), 560-569.

Zhang, L., et al., "Gene Expression Profiles in Normal and Cancer Cells", *Science* 276, (1997), 560-569.

Zou, J., et al., "The *Arabidopsis Thaliana TAG1* Mutant has a Mutation in a Diacylglycerol Acyltransferase Gene", *Plant J.* 19(6), (1999), 645-653.

DGATs

DGTT1
Assigned name: FGENESH2_PG.C_SCAFFOLD_80000044
Protein ID: 180240
Location: Chlre3/scaffold_80:231821-234837

Genomic sequence
235037 CGCGAGCTACCTGAGGCGAGAATGATGCGCGAAAGCTGCCCTCCACGTCGCGGGGCCTGTAAGGGCCGTT 234968
234967 CACGATCAACTATTTAGTATATTTGCACCTGATAAAGCACTGCTTTCGCCATGCAACGCAAAATGAAGCT 234898
234897 TAAGAGTGCTCAACTCACCGGACATCCAGGCGCTAGTATCGCTTTCTCCCGCGAAGTACTATGCAAAGTA 234828
234827 AGCGTTGTGCAGAGCTGGCCTCTGGGGCTCTGTGGCCCATGGACCGCGACCAGATGCGCGACCGCGACCC 234758
234757 ATGGAAGCTGCGCGACCGAGGTGCGCTGCAAAGCACAGAAACCACACGCTCTGTATAGAGGAACCGCCAA 234688
234687 AATAAGCATAATACACGAGCTTGCAGCACTCACTCAAGTGAGCGGGCACCTTCTGAAACCCTTGACTTGG 234618
234617 AGCGTCGTGAGCAGAATGAACCAACTAGAGCTCGTGATGTGTCGATTAGCTGTGTCTTGGTTCCTAATCA 234548
234547 CAGCTATAAGCCAAGCATGGGTGTGGCCTCTGCTCATCGGCACATTGCTTTACGTGCAGAGCACCACGCT 234478
234477 CACAATTGCCTTCCTGCTGTAAGTGCACTATATGTATGGTATCTAGCGTGCTATGGAGTTGTCGACGACG 234408
234407 GGCGTTTCCGGGGTTCCAACCGTCGCCGAAATCGAAATAGAAGCTTGACATGGCCGACTTTGTGCGCAGG 234338
234337 TACCTCTATTATGTTGTCGTCGGCCCGGGCTCTAAAGATGACGCCAACTGCAAGTGGAAGCCGACCTTCC 234268
234267 GCAAGTAAGGGGCTTCTTAGTCTAAGCGGGGCCAGGCTCATCAGCCGGGGGCACGGGATAGGCCGCGGGT 234198
234197 GGGCTTTCTTGCTACCTAGATGCAATCTACGCCCCACCGTAGGCCTTATCTCCGCCCTCCACTTACCCCC 234128
234127 ATCCACTCGCAATCCCACCCCGTACACCCACACACAAACTCATTCCCACAGGTGGCATATCTGGAAGGTT 234058
234057 ATGGCCTCTTACTTCCCCGGCGCCCGCCTGATTAAGACCGCCGACCTGGATCCGGCTGGCCGCTATATAT 233988
233987 TCGTGAGCCACCCGACACGCGTCATCGCCATTTCCGACTGGCTGGCATTTGCCACAGAGGCGCTGGGCTT 233918
233917 CTCCAAACTGTTCCCAGGTGCGTGACGACATGGCGTTTGCGTTACTATGAATTCTTTGAGTGCGCGTGCC 233848
233847 GTATTTTGCCTTGTCGGCAGCATGGGCCTAATGCGACGGTACGGTCGTGTCGGCTCCCACCTTCCGGGCT 233778
233777 AGACACTAGGATTTCGTGGATCGAGTCCCCGATGCCCACGCACGCCTGCCCCCACCTCCTGTGCCCCGCC 233708
233707 GCTGCCCCTCAACCTGCCTCTCGACCTGCCCCTCAACCTGCCCCTCAACCTGCCTCTCAACCTGCCCCTC 233638
233637 AACCTGGCCGCTCAAGGCCCCACTAATGGTCTTGGTCTGGTTGGTTTTGGAGTAAACTACCACACACGCA 233568
233567 TAAGTTCCGCAACACTCGTCATACACACAGACACACACAGACAAACAGACACACACACGCGCACACACAC 233498
233497 AGACAGACACACACACACTCACACACACACACACACGGCCTGAGTCTGGGACTACGCTGCAAACTACGGC 233428
233427 ACCACGCCAACCTGCCCATTGCCCTGCCCCGCTGCACACACGCCAGGCCTGGACCTGCGCTGCGCCACGC 233358
233357 TGGCTTCAAACTTCTGGGTGCCTGGTTTGCGTGAGTACATCCTATCGCACGGCATGTGCGGCGTGGGGCG 233288
233287 AGACACTCTGGCGCGCGTGCTGACAGGGTGAGTGGGAGGCTGAAGAGAAAGAGCGTACGGTACCAGCAAG 233218
233217 TTGATGGGTTGTGTTTGCCAGGGGGGCAGGTGCATGCCCAAGCTTACCAAATAGATCCTGACTTGTCAA 233148
233147 AGAGGGCTGAACTGTTAAATGCGGTGCAGCTTCCTGGGCCGTTGCCATGTGCCTGTTTGGAACACGCTTC 233078
233077 CCCCTCCCCGCCGATGTGTGCGCACACAGAAAGCCGGGCCGTGCGGTTGTGTTGGTGGTGGGCGGCGCGT 233008
233007 CTGAGGCGCTGTTGGCGGCGGAGGGAACTTATGACCTGGTGAGAGGGACGGAAGGGGTGAGGACTGATGG 232938
232937 GGGGGAGTCATGTCAAGCCCACACTAACGGGAACCTAGGACATAACCTGGCAGGGGGAGGAATGTTGCGG 232868
232867 AGGTAGGTACGGAGTGTGGTGCAAAAACCCTAGTGGTGCGGTCCCGAGGAACGTGTGCCCACAACATGCG 232798

*Fig. 1A*

```
232797 TGTGCTCACAGCAAGACAGGAATAGAGGAGCATTGTGCAAACCCTCAACATTGCTGTGCCTGCATGCAAA 232728
232727 CCCTCGACGTCCTGCTCATGTGCTCGTGCTTCCACTACAGGTGCTGCGCAACCGCAAGGGCTTTGTGCGC 232658
232657 CTGGCGCTGCAGACCGGCGCCAGTCTGGTGCCGGTGCTGTCGTACGGTGAGACAGACACCTTCCACACCT 232588
232587 ACATCCCGCCGCCCTGCAGCCGGGCGGCCGCGGTCATGAAGTGAGCCCCGCCACGCATGGTTCACGTTAC 232518
232517 CGCCACGCTTGATACTTTTGGTATATGAGGGAGTCCTTCCGCCCCCGCTGAAGCCGGCGTGACCCCTGCC 232448
232447 AACACCAGGATACCATGGGTTTACTTGCCTTGTCCCTTGCCTTATGCAATGGGTTCGGTTCAGTATGGGC 232378
232377 TGCAACCTGCAATCCCCCCCCCGTGCCCCCCGCCCATCATGAATGTAACCCCCTCCCCCGCACGTGTGCA 232308
232307 CGCGAACCTCCCGCTCGTGCAGGGTGCTGAAGCAGGTGTTTGGCTTCTCCACGCCCCTGTGCTGGGGCAC 232238
232237 CGGACTGTTCGGGGGCTGGGGCATGCTAGCGCTGCAGGTGCCGCTCACTGTGGTGGTGGGGGCACCCATA 232168
232167 CAGGTGGACAAGTGAGTGCCCGGCTGCGCGCGCGAGGGAAGTGGTTGGGCATGGCTGCGGTAGCTTGCCA 232098
232097 GCTAGCTGAGGACAGGAGTGCGGGTGTCAGCTGGCAGTACCGACGGCTCTGACAAGCAAGCTCCCCGTCA 232028
232027 CATCCCACGCGCCCACGCGGCCTCGCCACTGTGCGGCCCCGACTGCACACGCACACATACACGCTCACAC 231958
231957 ACAGGGTGTCCAGTCCCACGGAGGCTGAGGTGGCGGCGCTGCATAAGACCTACACGGAGGCACTGCAGAA 231888
231887 GCTGTGGGATGACACAGTGGACAAGTACGGCAAGGGTGTCAAGCGGCCGCTGGCCATCGTGCAATGATAC 231818
231817 TATTACTATTAGCTAGGGACAGCAGTGGCAGACTGGAGCGGCGGCAGCAGCAGCAGCGGGGGAGGCA 231748
231747 GCGGCGGTGGCGTCAGCAGTGGCAGGAGCGGCGGTAGCAGCGGCAGGAGCAGAGGGTGCGGTGGAATCAG 231678
231677 GGCGGCGCCAGACTTGGCAGCAGCGTTGTGCGTGCACGGCACATGAGTGGCACTGAG 231621
```

*Fig. 1B*

Transcript sequence
```
  1 ATGCAAAGTAAGCGTTGTGCAGAGCTGGCCTCTGGGGCTCTGTGGCCCATGGACCGCGACCAGATGCGCG  70
 71 ACCGCGACCCATGGAAGCTGCGCGACCGAGCTATAAGCCAAGCATGGGTGTGGCCTCTGCTCATCGGCAC 140
141 ATTGCTTTACGTGCAGAGCACCACGCTCACAATTGCCTTCCTGCTGTGGCATATCTGGAAGGTTATGGCC 210
211 TCTTACTTCCCCGGCGCCCGCCTGATTAAGACCGCCGACCTGGATCCGGCTGGCCGCTATATATTCGTGA 280
281 GCCACCCGCACGGCGTCATCGCCATTTCCGACTGGCTGGCATTTGCCACAGAGGCGCTGGGCTTCTCCAA 350
351 ACTGTTCCCAGGCCTGGACCTGCGCTGCGCCACGCTGGCTTCAAACTTCTGGGTGCCTGGTTTGCGTGAG 420
421 TACATCCTATCGCACGGCATGTGCGGCGTGGGGCGAGACACTCTGGCGCGCGTGCTGACAGGAAAGCCGG 490
491 GCCGTGCGGTTGTGTTGGTGGTGGGCGGCGCGTCTGAGGCGCTGTTGGCGGCGGAGGGAACTTATGACCT 560
561 GGTGCTGCGCAACCGCAAGGGCTTTGTGCGCCTGGCGCTGCAGACCGGCGCCAGTCTGGTGCCGGTGCTG 630
631 TCGTACGGTGAGACAGACACCTTCCACACCTACATCCCGCCGCCCTGCAGCCGGGCGGCCGCGGTCATGA 700
701 AGGTGCTGAAGCAGGTGTTTGGCTTCTCCACGCCCCTGTGCTGGGGCACCGGACTGTTCGGGGCTGGGG 770
771 CATGCTAGCGCTGCAGGTGCCGCTCACTGTGGTGGTGGGGGCACCCATACAGGTGGACAAGGTGTCCAGT 840
841 CCCACGGAGGCTGAGGTGGCGGCGCTGCATAAGACCTACACGGAGGCACTGCAGAAGCTGTGGGATGACA 910
911 CAGTGGACAAGTACGGCAAGGGTGTCAAGCGGCCGCTGGCCATCGTGCAATGA 963
```

*Fig. 2*

Protein sequence
MQSKRCAELASGALWPMDRDQMRDRDPWKLRDRAISQAWVWPLLIGTLLYVQSTTLTIAFLLWHIWKVMASYFPGARLIK
TADLDPAGRYIFVSHPHGVIAISDWLAFATEALGFSKLFPGLDLRCATLASNFWVPGLREYILSHGMCGVGRDTLARVLT
GKPGRAVVLVVGGASEALLAAEGTYDLVLRNRKGFVRLALQTGASLVPVLSYGETDTFHTYIPPPCSRAAAVMKVLKQVF
GFSTPLCWGTGLFGGWGMLALQVPLTVVVGAPIQVDKVSSPTEAEVAALHKTYTEALQKLWDDTVDKYGKGVKRPLAIVQ

*Fig. 3*

DGTT2
Assigned name: ESTEXT_FGENESH2_KG.C_240043
Protein ID: 184281
Location: Chlre3/scaffold_24:1045601-1050433

Genomic sequence
1045401 AAGCGCGGTGTAGTATCCCGGGTAATGTTTTAGGATGCGATTAAGTGTGATCAGCGTATAGAGATGAGGC 1045470
1045471 GTGCAGACTACAGCGCCTGCTCGCGTGTGCAAAGGGCCATGCAGGGGTCTGATGGGGGGCGATGGTGGGC 1045540
1045541 CGGGAGCGCGGGGAACTTCTCTCGCGGCTTCCGGGCATGCATTTTGAGCTATTTGCATGTGGATTTGCAA 1045610
1045611 CTTTCGATATAGTTACGATTTGCGTGGGACCGCCCCATTCACCTAAGAAGCGGGCCTATTGGCCGCCCCA 1045680
1045681 CCCGCTGGTAAATTGCGAGTGGGGCGCGCGTCCTAGCTGGATTTAGGCCATCTGTTTTTGATTAAAATTG 1045750
1045751 CAAGTCCGTGTGTCGCGCTCCCCTAAACGTTGGCGCGCCATAATGGCGATTGATAAAGCACCGACAAATG 1045820
1045821 TGCGAATTTGGAGCGATGGCGTCACGGAGAAGGGCAAGCAAAGCATCTTCTCATCGCTGGTGGCTATGTT 1045890
1045891 GACGCTCTTCATCTACTGTGGTGAGTTTGTAGAGGCCGGATAAGTCGACGCGAACCGCGCTCCCAGAGGG 1045960
1045961 CGTCGAAAAGTTTCGTTGGCAACCTGCGGGGATGGCGCGTGTGAACCGTCACGCTCGTGCCAATCGACGC 1046030
1046031 CACCTGGCCGGCGGCCACCTCCCTGCGGCACCCGTCCCCGCCTGGATCAGGCTGGATGCATGTGCTGCTG 1046100
1046101 GCGCTTGTGATCCTGTCCTTCTGGTACCGCTGGGCGCTGGTGACGGTGCTGCTGCTGTACTCCACCCTGC 1046170
1046171 TGCTGCCGCCTAAGCCGGTGCGTGTGCGGGAAGCTCCGCCGACGGGCAGCGGCTCCACTGCCGCAGGGCC 1046240
1046241 CAGTCGCATGGCTGAAGTGCTACTTGTGTGGATCGGGTGGTATGCTGTCGGGGCTGCCGTTAACCACTGC 1046310
1046311 ATTTGGACGTATGGAAGCGGTCCCTGAAGCAGTCCCAAAGACCGCATAGTGATTCTTGGACCCCTATTCG 1046380
1046381 TGTTCGCGCGTGCAGGTGCTGTGGGGACCGGTCTGTCGCTCCTGGATCTTCCAGACCTGGCGGGAGTGAG 1046450
1046451 TGCTGGGAATCCTTGTGGGTCATTAGGGGCTAGCGGCCTGGTCGTGCCGCGCCAGGTGGACAGGGACTGC 1046520
1046521 ATTCTGCATGCGTGCAGGCTGGAGCAGCGGTGGAGGCAGCGGCAGAGCGGCGGCAGGCAGGCAGCATGGC 1046590
1046591 CCATGAGGGAGCCAGACACGTAGCAGTACCAGCAGTACCCAAAAGCAAAAAAAGAGTCGTGTAGCGGCAG 1046660
1046661 CGGCGAGCTACCAGTCAGCTGACAATGACATAAGAGAGCCAAGCACAAAGAAGGGCCGACCGTGCTACTG 1046730
1046731 GCATCTCGCTTTAGGGCAGGCAGGGCTGGGCGGGCGAGCTCCGCAGCACGCACTCCAAAAGCGTCTGGGG 1046800
1046801 AAGGGCGTACGCGGCCTGGCCGTAGTCAGGCGCCGCGTGCTAGTAGCCAGTGAACTACCGGCGCCGCGCT 1046870
1046871 CACCCCTTGAAGTCGACGACGTCGGGCAGGGGAACCGGTCGGGTTGCGGGGTGTGGACCTCGCCAACGTA 1046940
1046941 TCTAACCCCGCCCCTGCCCCTACTTGCTTCTGAAAGGTGTTGAATCACCTCCGTCCACCCGCCGCCTCTC 1047010

*Fig. 4A*

```
1047011 GCCAGGTACTTCAAGTTCTCTTACGTGTTTGATGAGGTGCTGGACTCGAAGAAGAAGTACATCTTCGCGG 1047080
1047081 AGTAAGTTTTGCGAGGTGGACATGTGGTTGCCGCCTTCAAGGCTACACACAGCTAGGGTTCCATCCTTGT 1047150
1047151 GGCTGCCATTTGCTACACCTGCGGATGCTGACACCCTTTGTCGCCCTTTCTTGCAGGTTCCCGCACGGTG 1047220
1047221 AGCTGTCGTGGAGGCGTAGGAGTAGCAGCGGCAGATGTGGTTTGCGCGCGTGCATGGGACTTGGCCTGGA 1047290
1047291 TCTATGTTGGTACCCAGGTTTACTAGTTAAGGGTTTCTCGGGAGCGTGCGCTCTAGGAGCTCTGCCAGCT 1047360
1047361 ACTGGTGCTGCGTTGCTTGCCGTGCTGCCGAGCACAATGGGAATGGAACCGTTGCGGCTGGGCCCATAAC 1047430
1047431 TTCCTGACGTACCCGTGCACTGCGTTGTACCCTGTGCATCAAGCACCTTACGGAACCTCTGACTGCCCCA 1047500
1047501 CCCGCCGCCCACCGCTACCGCCTACCTTCCAAAACCAGGTGTCTTCCCCATGGGCCCACTGTGAGTTCTG 1047570
1047571 CGTTTTGCGTGCGCCTGGTTCTACGTCACGGATTCTTGGAAAGGGTTAGCGCTGGGTACGAGGGGCGATT 1047640
1047641 GACGCATTTGGTAACGCTTTGACGCACTGGGAGAACGAGCGGCGCTGAACCTCACCGTTGCCGCGGCCGC 1047710
1047711 CATCACATTAGCGGGCGCACCAGTAGCGACCACAGCTACTGCCACGCCATGCCGGGTCATCCTTCGTTCT 1047780
1047781 GGCCGCCGTCCATGCCCTGGCCCTCCTCACGGGTTTGCGCATGTGCACCCGCAGCATTGGCGCCACAGAA 1047850
1047851 TGCCAGATCATGTTTCCCGGCTTTGACATCTTCGGGCTGGCGGCGAATGTGGTGAGTGCCTGTCCGTGGC 1047920
1047921 CTTGTGGCTGGTCGTTTTTTTGAGCTTTGGCGATTTGCTTTGTGTGAGAGAGTAGCTGCCTGACTTGTCC 1047990
1047991 ACGCCTGAGATCTTTGGCGTTTACACTCCCAGGTGTTCACGGTCCCCTTCTGGCGGCATTTCGTGGCGTG 1048060
1048061 GCTGGGCTCCGTGCCGGCCACCACACGCGACTTCAAGCGGGTGCTGAAGCAAGGAAGCGTGGCGGTCATC 1048130
1048131 GTGGGAGGCATCGCAGGTGCGTGGCGGCTGGCGGCTGCTAGTGGCTGTGTGGTGGTGCTAGGCGTGTGCG 1048200
1048201 TGTGGGTCGGTGTAACTGGAGCTTGGCTGGGGTGTGTATGGGCGTCAGCACATAAGCAGGGTTCTGTCAA 1048270
1048271 GGACAGATGCCGCTGCGGCGATGTGCTAGCAGGGAGGTTAGTTAGGCATGGGACCGTGCTATATGGGGTA 1048340
1048341 CGCAAGGGTTTTGCCCGGCATTACCTAGACGCAAGCTCGGGGTTGGCTGTCGAAGAAGATGGCCAATGTG 1048410
1048411 GGGCTACGAGGGTGCCGGGCTGTACCTGCGGTCCACATGCACGTGTGGTGCGGGCGGCATCGCCACCAGC 1048480
1048481 AGTCGGCTGCCGAGCTTGCAGCGAGAACCACTGACTCTGGTGTATGTCACCGACCCCGCCGCACCCCGCC 1048550
1048551 CGCAGAGATGTACATGCAGAGCCCACGAAGGAGCAGGTGACGAGGCGGGCGCCGGCGGGTGTGCGGGGC 1048620
1048621 ACCACCGGCAGCCAATGTGCCGCCGTGTCGCATGTTGCCAGTCGTAAACAGCTGATCGGATGCAATGCGA 1048690
1048691 TGCGATGTGCGTCAAGCAGTATGCGCTATGGCTGACGCACGTGTCTGCCGTACGATCGAACAGATCATGT 1048760
1048761 TGAAGGACCGCAAGGGCTTTGTTCGTGTGGCGGTGGAGGAGGGCGTGGATGGCGGCATCGTGCCGGTCTA 1048830
1048831 CCACTTTGGCAACTCTCAGGTGGGTGTGAAGCTCCGGACAAGGGAGCGAGCGCACGTGGGGGCGAGCGTA 1048900
1048901 CGTACATGGGAGCGGGAGGAGGAAGCGAGCGCGGGAATGTAATTAAATTTGGCCGTGCGCTGCCAACAGC 1048970
1048971 CACTGAGGGCTTGCTCAGCTGCGCTCCCGGCTTAGCGCCGCCTACCCATAGCCTTGCAGCCTGGCCTCAC 1049040
1049041 GCACCAATAGGTACCGCCTGCCCACCTGCATCTATCCACGTACGCCTGTTTCCGTCTTTCGCTTCGGCTT 1049110
1049111 TCCCTGCTCCACGCGCCCCGGCGCGGACCTGCAAATGGGCTCGGCCACAAGGCCTCCTCCCCTCCACCAA 1049180
1049181 CACTTCCACCTCCACCTCCCGCGCCCCCAGGTGCTGGACTTCGGCCCCCAGGCCATGGCCAGTGTGTCCC 1049250
1049251 GCCGGCTGCGTGCGGCCCTGGGCTTCCTGTACGGAGTGGCCTACCTGCCCCTGCCCAGGTGCGTGTGCGT 1049320
1049321 ATATGCGTGTGCTTGTGCGTGTGCGTGTGCGTGTGCGTGCGTTGTGCGTGTGCGTGTGCGTGTGTGTGT 1049390
1049391 GTGTGTGTGTGCGTGCGTGCGCGTGTGTGCGCGTGCGTGTGGGCCCCGCACTTGCATGTTGCGGTA 1049460
1049461 TCGCGCATGTATGTGTGTCGCTCCTGTATCCGCCCTGCAAGCCCGCAGCACCGCGGCCTGCTGCTTATGC 1049530
1049531 TGCCTCGCCCGCTCACCCGGTGCCGTCCGCACGGCTGCGCCTCCCTTGCACTCATGGACACAGGCGCCGC 1049600
1049601 AACATTTACATGGTGTGCGGCAAGCCCGTTCCCGTCACGCGCACCGCCCGCGACGACCCCAAGGTGTGTA 1049670
```

*Fig. 4B*

```
1049671 TGTGTGTGTTAAAGAGCACAAGGAAAACATTGCGCAAAGACAGTATGCGATGCAGCAAAGCGACTGTTTA 1049740
1049741 CGGATGTTACATGAACTTACCTCGCATGCCCGCTGCGGTGAGCCGCCGGCCTTACCAACCGGAAATCGCG 1049810
1049811 CAACCCCCGCTACTCAAACCTCGAGGGGGCATTAGCGTCCACACGCTCTCAAGGGTGCAAACCCAAGCAT 1049880
1049881 GTGCTCACGGTACCGTGTGTGTGTATGTATGTGTGCATGTGTGTGTTGGTGGGCGGGGCGGTTGAAGCG 1049950
1049951 TTGTTGGGGCCTGCAGGGCAATTCGTCAAGCCCCAGGGCGCATGACGAATTGACAAGAGCATTGCCGGCT 1050020
1050021 AGGTCGGCTCCGTATGCATGCGTCCTCTGGCCGACATACCAGTCCTTAAGCCCCTTGCTCGAGCACGACC 1050090
1050091 CCTATCCGTTTTGCCCCCAAACAATGGTACCACCGTCTCCTGCCTGCCTTCCACCCTGTATCCCGCCGCC 1050160
1050161 GCAGTTTGAGGAGGTGGTTGACGCCACTCACGCCGCTGTGATGGCGGCCCTGCAGGAGGCCTACGACCGC 1050230
1050231 CACAAGACCGAGTACGGCTGGGCCGACCGACCGCTGGTCATCAGCTGAGCGGGCGGCGGTTGAATGGCTG 1050300
1050301 GGATCTGTTGCTGGTGCTGATTTGTAAGTGTGGCTTGGCGCAATACAGGCGGCGGCAGCAGTGGCGGCGG 1050370
1050371 CAGCACCCAGGGTAGCAGGAGCTGCGCAGCCGAAAGTGAAGGCGCTGGGAGAGTTGTGCGTGCAACACAG 1050440
1050441 AGAGGGAGGGAAAGGGCGACCAGAGGCCAAGGGGAGACCACGCAGCGCGTCGCAGCGACATGGGCATGCG 1050510
1050511 TAGTGTGCTGACGGCCGCAGTCTGAGAGGGAAGTGTGAAAGTCAGGAATGAGGCTTTCTGGGGACGCACG 1050580
1050581 CGCGCATGCATGGCCTCAGCTGGTGGCCATGACTCCGGTGCGGGACTGCGGGC 1050633
```

*Fig. 4C*

Transcript sequence
```
   1 GGATTTGCAACTTTCGATATAGTTACGATTTGCGTGGGACCGCCCCATTCACCTAAGAAGCGGGCCTATT   70
  71 GGCCGCCCCACCCGCTGGTAAATTGCGAGTGGGGCGCGCGTCCTAGCTGGATTTAGGCCATCTGTTTTTG  140
 141 ATTAAAATTGCAAGTCCGTGTGTCGCGCTCCCCTAAACGTTGGCGCGCCATAATGGCGATTGATAAAGCA  210
 211 CCGACAAATGTGCGAATTTGGAGCGATGGCGTCACGGAGAAGGGCAAGCAAAGCATCTTCTCATCGCTGG  280
 281 TGGCTATGTTGACGCTCTTCATCTACTGTGGCTGGATGCATGTGCTGCTGGCGCTTGTGATCCTGTCCTT  350
 351 CTGGTACCGCTGGGCGCTGGTGACGGTGCTGCTGCTGTACTCCACCCTGCTGCTGCCGCCTAAGCCGGTG  420
 421 CTGTGGGGACCGGTCTGTCGCTCCTGGATCTTCCAGACCTGGCGGGAGTACTTCAAGTTCTCTTACGTGT  490
 491 TTGATGAGGTGCTGGACTCGAAGAAGAAGTACATCTTCGCGGAGTTCCCGCACGGTGTCTTCCCCATGGG  560
 561 CCCACTCATTGGCGCCACAGAATGCCAGATCATGTTTCCCGGCTTTGACATCTTCGGGCTGGCGGCGAAT  630
 631 GTGGTGTTCACGGTCCCCTTCTGGCGGCATTTCGTGGCGTGGCTGGGCTCCGTGCCGGCCACCACACGCG  700
 701 ACTTCAAGCGGGTGCTGAAGCAAGGAAGCGTGGCGGTCATCGTGGGAGGCATCGCAGAGATGTACATGCA  770
 771 GAGCCCCACGAAGGAGCAGATCATGTTGAAGGACCGCAAGGGCTTTGTTCGTGTGGCGGTGGAGGAGGGC  840
 841 GTGGATGGCGGCATCGTGCCGGTCTACCACTTTGGCAACTCTCAGGTGCTGGACTTCGGCCCCCAGGCCA  910
 911 TGGCCAGTGTGTCCCGCCGGCTGCGTGCGGCCCTGGGCTTCCTGTACGGAGTGGCCTACCTGCCCCTGCC  980
 981 CAGGCGCCGCAACATTTACATGGTGTGCGGCAAGCCCGTTCCCGTCACGCGCACCGCCCGCGACGACCCC 1050
1051 AAGTTTGAGGAGGTGGTTGACGCCACTCACGCCGCTGTGATGGCGGCCCTGCAGGAGGCCTACGACCGCC 1120
1121 ACAAGACCGAGTACGGCTGGGCCGACCGACCGCTGGTCATCAGCTGAGCGGGCGGCGGTTGAATGGCTGG 1190
1191 GATCTGTTGCTGGTGCTGATTTGTAAGTGTGGCTTGGCGCAATACAGGCGGCGGCAGCAGTGGCGGCGGC 1260
1261 AGCACCCAGGGTAGCAGGAGCTGCGCAGCCGAAAGTGAAGGCGCTGGGAGAGTTGTGCGTGC          1322
```

*Fig. 5*

Protein sequence
MAIDKAPTNVRIWSDGVTEKGKQSIFSSLVAMLTLFIYCGWMHVLLALVILSFWYRWALVTVLLLYSTLLLPPKPVLWGP
VCRSWIFQTWREYFKFSYVFDEVLDSKKKYIFAEFPHGVFPMGPLIGATECQIMFPGFDIFGLAANVVFTVPFWRHFVAW
LGSVPATTRDFKRVLKQGSVAVIVGGIAEMYMQSPTKEQIMLKDRKGFVRVAVEEGVDGGIVPVYHFGNSQVLDFGPQAM
ASVSRRLRAALGFLYGVAYLPLPRRRNIYMVCGKPVPVTRTARDDPKFEEVVDATHAAVMAALQEAYDRHKTEYGWADRP
LVIS

*Fig. 6*

DGTT3
Assigned name: ESTEXT_FGENESH2_PG.C_120236
Protein ID: 188937
Location: Chlre3/scaffold_12:1688101-1691558

Genomic sequence
1691758 GAAGCCCGCCTTGCGGGACAGCATGTTTGCGAGGGCCATTTTGAATCTAATTGAGGTGGGCTAAACGGGC 1691689
1691688 TTCCACACGAAGCTGTGCAAAACTTGGACTCCTTTGCAAGTTGCCGAGGTCGCCCATGCAGCGACTCGCG 1691619
1691618 CGCATGGTCCCCCCGCGGTGAACAAATGCCGCTCGCCTTCTCACGTAAACAATATAACTTGCTTACCAAT 1691549
1691548 ACTGTTTGCAATCGTATACGTGCGGCGCAGCGTGCGGGATACGTCCCATAAACACCACTGCATAATCCGC 1691479
1691478 GTTAGCCAACGAGCTTCCCCAGCGCCCCCGCGCGTGCACTGGCGGCTTTCGGCACTAGCCAAGCCTTTAG 1691409
1691408 GCGTAGACTGGGCGCCTGAGGCGCGGACACACAGCCGCACCGAGACGTTGAGCGTTTCATCCGAGCTCAC 1691339
1691338 TCACGCGCATCGCCGGCGGGACACTGCGCACGGAGCCCGCGCGCGTGGACACCTGGGCCCCTGCACGAAG 1691269
1691268 GGCCCCTGCGAGACGGAAGCAGATGGCAGGTGGAAAGTCAAACGGCACGGGCGCGGCGGACGCGCACGTG 1691199
1691198 CGTACCTCGCACTTGACCCTGAAAGCTGGGGAGGACCCGCCCCGAATGTTCGCATCTACAGTGACGGTG 1691129
1691128 AGCCCGGATACATGCATTACACGACAGCAGACCTCATGCTCCGGCGTATTATGACATCAGGGTGGACGGC 1691059
1691058 TGCTGTGCGGCGTATAGGGCGGCTACAGCCGTGGGCACAAACGCAGCACATGCCTTACCTCTCCTCACCT 1690989
1690988 GCAATGCTACTGCCGCCGCAGGCATCAAGCCGGACGCGCGGCAGAACCTGCTTGTTCAGATCCTGGCCGG 1690919
1690918 CATCACGATGTCGATTTATGTAGGCAAGTGCATTCAGCTGACAGGAAGGTCTGGGCGCGCTCCCAGGGCT 1690849
1690848 CCAACTGGATAGTGATTCCCACACTCGGACAGCGGACACGGCCGCACATAGCGGTAACAGCACATTCGGT 1690779
1690778 CGGGGCCTTGGGACTGTACCCGGCATCTAAGCATGCCGCGTAACTACTCGCGCACCGTGCATCCGCAACC 1690709
1690708 AAAACTTTGCCTCCATTCTTGAGCTCAACCCAACCTCATTCCTTGTTTGGACGTTCCCCGTCCCAAGGCT 1690639
1690638 TCATGAACTATTTCATGCTGCTGGTGGTGCTCTCCTACTGGAGCCGCATCTGCCGCTATGTGGTCCTGGC 1690569
1690568 GCTGCTAGGCACACTGGCGCTGCCCTGCAAGCCCGTGCTGTGGCCTGCCTTCAACAAGCTGTGGATCTTC 1690499
1690498 AAGACCTGGCGTCACTACTTCCACTACAGGTGCACAGCAACGGGCGGCTGAATGCCTTGGTGTATCGCTG 1690429
1690428 GCGGGCAGGACGTGGGCCCGGGTCTGCATGTGCTGTGCCGCTGCGCTGCGTTGCTACTCCTGCGCTTTGC 1690359
1690358 TGCACGGTCGCGGCGAGCAGCGGCCGGCGATGAATTTAGAAGACACTACAATCTCTGTATTTGTCGTCAT 1690289
1690288 GCTTCGTGCGTGTAGTTTCCTGATTGAGGAGCCGCTTGACCCCAACAAGCGCTACATCTTTGTCGAGTGA 1690219
1690218 GTGCGGGGACTGCAGCACAGGCATTCTACATGTGGCCAGGAAGTCAAGGTTGTATTGTTGGCTTCGGCTA 1690149
1690148 CTAGTATGCTCATTTTCTTACTCCCAGCCACTTTCGCTGCCGCCCTCACCTTGCAGGTTCCCGCACGGCG 1690079
1690078 CGTTCCCCATTGGTGAGTGGTTGTTTGTCCGGTGACGGCTGTGCGATTACCCGACTGGACTGACTGGGGT 1690009
1690008 CACGCATGGTGCTTGGCCTGGCTCAGCTCCGCAGGTGCCTTGTTTGTCGCAACGCCTTCGGGCAGTGCAG 1689939
1689938 TAATGCGCCCGCATTCCTTCACTCGTCCTTCCCCCCGCAGGTCCCATCGTGGCGGGCACGCTCATGCAGA 1689869
1689868 CTCTGTTCCCGCACATGATGATCTACAGCGTGGCCGCCTCCGTCGTGTTCTACATCCCCTTCTGGCGCCA 1689799
1689798 TTTCATCACGTAAGCTTGCAACAGGACAGACTCCCGCTGGGTCTACAGCAGTCGCCGACATCCCGATTTC 1689729
1689728 GCTAGGAAGAGCCGTACCATGCCGAATATGCTGCCGATCTCTCGGATTCACTGTGTTGCAAACCCTGGGC 1689659
1689658 GCTGTTGCAGGTGGATCGGCTCGGTGCCCGCAACGCCCGGCAACTTCAAGCGGCTGCTGAAGAAGGGCAG 1689589
1689588 TGTGGCGGTGGTGGTGGGCGGCATTGCCGAGGTAGGCGCGCCTAGGCGATGGGATCAGGGTCATGCTCTG 1689519
1689518 AGAGGGGTCGCGAAGCCATTCAGGACTGGCCACTCCGGCCAAACCAGCTACCATACGCGCTGTTCAAACC 1689449
1689448 CTCCCTTTCCCGCTCCTGCTTGCCCACCTGCCCCGTCCATCTGCAGATGTACATGGGCAACAAGAAGAAG 1689379
1689378 GAGCGCATTAAGCTAGTGGGCCGCCGCGGCTTCGCACGCATCGCGCTGGAGGAGCAGGTGGACGGCATTG 1689309
1689308 TGTGCGTGTACTACTTCGGTCAGAGCCAAGTGCTGGACTTCGGGCCCTCCTGGCTGGCGGACTTTAGCCG 1689239

*Fig. 7A*

```
1689238 CCGCATGCGCACCAGCTTCGGCTACCTCACGGGATGGATGGGGCTGCCGGTGCCGCGGCCCATCCCCATC 1689169
1689168 TACGTGAGTGGGGGAGTCGGGGGCCCCGGCCTGGTGGCAAGTCGCTTTCACGAAACTCGGCGCTCTGTGT 1689099
1689098 ACAGTATGTGGCCAAGAAGTAGAGGGGAAGGAAAACGGATGGCAACCACGAATACTCAAAAGCCATACGC 1689029
1689028 CACGGAAGGGTCAGACGCTAGGGATGTATCGTTGCTGCTCGGCTGGCGGCCACATCATTCAGCACTGCCC 1688959
1688958 GTCACCGGTCTCGCGGCACGTGCGGCTGCAATGCTCGCTGCATCCGCGTCAACCTTGCCGCCACTGCTCG 1688889
1688888 TGTACACGCACACGCAGATGGTGAATGGGAAGCCCATCCCGGTGCCCAAGGTGGCTCGTGACTCGCCCGA 1688819
1688818 GTTCGACAAGGAGGTGGATAAGCTGCTTGACGCCACCATCACGGAGCTGGGCGAGATGTACAACAGGCAC 1688749
1688748 AGAGGCGAGTACGGCTGGGGCGACCGCCCGCTGTCCATCGAGTAGATGCCCAACAAGTGGATTGGCACAG 1688679
1688678 TGGTGCCCTTGAAATGGCATGGCCAGAGTGAAAGCGGGATGGATCGTTGGAGATGGTTATGGAGGGGAGG 1688609
1688608 AAGGAATATCTTGAAAAGGCCACGCGGATGGGTTCGTGAGGCATGCAGGGCCTTTCGGGTTGGATGGGGG 1688539
1688538 TCGCACTAGTCGCACGTGCCGCGTGGGCACGTGTGTGCCGTAAACCTTTTATGGTATGGTGTGTCAAGAC 1688469
1688468 TAGTCTAGACGTACCGATGGCTATATGGTAGCTCAGCTATGCGAAAAGCTGCGAAACGGGCTGGCATTGC 1688399
1688398 CTTTGGGTGAACGTGCAAGTGTTGTGTTTAGATGCAAGGCAGGTGGATGCAGTTGTAGGTGTAGCAGACC 1688329
1688328 TTTACATCAGCACAGTTGGCTAGATAGGTCGCGTCAGCCAAGGAGGGAGCTCTGCGTTTGATTGGGTTGA 1688259
1688258 TGCTGCCAGCAGGCGGCATTAAAATGGACGTGGCAAGGGAGCAATAGAGCCTTTGAAAGAATGCCATATC 1688189
1688188 CTGAAGACACACGTGCATGACGCAAGGGTCCCGTTGCTGAGCTCCTGACTTGATCATCCCTTGGATGCTG 1688119
1688118 TCACGCAATGTGCTTCAAGTGCGCCGCTACTAACCTACTACCGTATGGTCACGGGTGCTCAACATATCAC 1688049
1688048 CGCTGCTGAGCGGTCATTACCTGCAGCCCAAGTGCCCAACCCTGCCCAGTGGAGGCCCACCCTGGACTTG 1687979
1687978 CGGGTCACCATCATCCTCCACAGCCCCACTTGCACAGTCTGACACTGCAGGACAGAACGCGGGCATTTA 1687909
1687908 GGACGCGG 1687901
```

*Fig. 7B*

Transcript sequence

```
   1 GCTTACCAATACTGTTTGCAATCGTATACGTGCGGCGCAGCGTGCGGGATACGTCCCATAAACACCACTG   70
  71 CATAATCCGCGTTAGCCAACGAGCTTCCCCAGCGCCCCCGCGCGTGCACTGGCGGCTTTCGGCACTAGCC  140
 141 AAGCCTTTAGGCGTAGACTGGGCGCCTGAGGCGCGGACACACAGCCGCACCGAGACGTTGAGCGTTTCAT  210
 211 CCGAGCTCACTCACGCGCATCGCCGGCGGGACACTGCGCACGGAGCCCGCGCGCGTGGACACCTGGGCCC  280
 281 CTGCACGAAGGGCCCCTGCGAGACGGAAGCAGATGGCAGGTGGAAAGTCAAACGGCACGGGCGCGGCGGA  350
 351 CGCGCACGTGCGTACCTCGCACTTGACCCTGAAAGCTGGGGAGGACCCGCCCCCGAATGTTCGCATCTAC  420
 421 AGTGACGGCATCAAGCCGGACGCGCGGCAGAACCTGCTTGTTCAGATCCTGGCCGGCATCACGATGTCGA  490
 491 TTTATGTAGGCTTCATGAACTATTTCATGCTGCTGGTGGTGCTCTCCTACTGGAGCCGCATCTGCCGCTA  560
 561 TGTGGTCCTGGCGCTGCTAGGCACACTGGCGCTGCCCTGCAAGCCCGTGCTGTGGCCTGCCTTCAACAAG  630
 631 CTGTGGATCTTCAAGACCTGGCGTCACTACTTCCACTACAGTTTCCTGATTGAGGAGCCGCTTGACCCCA  700
 701 ACAAGCGCTACATCTTTGTCGAGTTCCCGCACGGCGCGTTCCCCATTGGTCCCATCGTGGCGGGCACGCT  770
 771 CATGCAGACTCTGTTCCCGCACATGATGATCTACAGCGTGGCCGCCTCCGTCGTGTTCTACATCCCCTTC  840
 841 TGGCGCCATTTCATCACGTGGATCGGCTCGGTGCCCGCAACGCCCGGCAACTTCAAGCGGCTGCTGAAGA  910
 911 AGGGCAGTGTGGCGGTGGTGGTGGGCGGCATTGCCGAGATGTACATGGGCAACAAGAAGAAGGAGCGCAT  980
 981 TAAGCTAGTGGGCCGCCGCGGCTTCGCACGCATCGCGCTGGAGGAGCAGGTGGACGGCATTGTGTGCGTG 1050
1051 TACTACTTCGGTCAGAGCCAAGTGCTGGACTTCGGGCCCTCCTGGCTGGCGGACTTTAGCCGCCGCATGC 1120
1121 GCACCAGCTTCGGCTACCTCACGGGATGGATGGGGCTGCCGGTGCCGCGGCCCATCCCCATCTACATGGT 1190
1191 GAATGGGAAGCCCATCCCGGTGCCCAAGGTGGCTCGTGACTCGCCCGAGTTCGACAAGGAGGTGGATAAG 1260
1261 CTGCTTGACGCCACCATCACGGAGCTGGGCGAGATGTACAACAGGCACAGAGGCGAGTACGGCTGGGGCG 1330
1331 ACCGCCCGCTGTCCATCGAGTAGATGCCCAACAAGTGGATTGGCACAGTGGTGCCCTTGAAATGGCATGG 1400
1401 CCAGAGTGAAAGCGGGATGGATCGTTGGAGATGGTTATGGAGGGGAGGAAGGAATATCTTGAAAAGGCCA 1470
1471 CGCGGATGGGTTCGTGAGGCATGCAGGGCCTTTCGGGTTGGATGGGGGTCGCACTAGTCGCACGTGCCGC 1540
1541 GTGGGCACGTGTGTGCCGTAAACCTTTTATGGTATGGTGTGTCAAGACTAGTCTAGACGTACCGATGGCT 1610
1611 ATATGGTAGCTCAGCTATGCGAAAAGCTGCGAAACGGGCTGGCATTGCCTTTGGGTGAACGTGCAAGTGT 1680
1681 TGTGTTTAGATGCAAGGCAGGTGGATGCAGTTGTAGGTGTAGCAGACCTTTACATCAGCACAGTTGGCTA 1750
1751 GATAGGTCGCGTCAGCCAAGGAGGGAGCTCTGCGTTTGATTGGGTTGATGCTGCCAGCAGGCGGCATTAA 1820
1821 AATGGACGTGGCAAGGGAGCAATAGAGCCTTTGAAAGAATGCCATATCCTGAAGACACACGTGCATGACG 1890
1891 CAAGGGTCCCGTTGCTGAGCTCCTGACTTGATCATCCCTTGGATGCTGTCACGCAATGTGCTTCAA      1956
```

*Fig.8*

Protein sequence

MAGGKSNGTGAADAHVRTSHLTLKAGEDPPPNVRIYSDGIKPDARQNLLVQILAGITMSIYVGFMNYFMLLVVLSYWSRI
CRYVVLALLGTLALPCKPVLWPAFNKLWIFKTWRHYFHYSFLIEEPLDPNKRYIFVEFPHGAFPIGPIVAGTLMQTLFPH
MMIYSVAASVVFYIPFWRHFITWIGSVPATPGNFKRLLKKGSVAVVVGGIAEMYMGNKKKERIKLVGRRGFARIALEEQV
DGIVCVYYFGQSQVLDFGPSWLADFSRRMRTSFGYLTGWMGLPVPRPIPIYMVNGKPIPVPKVARDSPEFDKEVDKLLDA
TITELGEMYNRHRGEYGWGDRPLSIE

*Fig.9*

DGTT4
Assigned name: CGLD24 (annotated)
Protein ID: 190539
Location: Chlre3/scaffold_19:1174641-1178245

Genomic sequence
```
1174441 TCTGCTGGATAGCGAGACAAGAATTCGCTTGCACAATCATTGGGCGGGAAGCTTTCCTCGGGTGTTCGCA 1174510
1174511 AAGCTCCCATGGAGTTCTTTATTAAAGCATGTAACTGACAATCAGTATAACTAGCCTAGTTACGTAGCGC 1174580
1174581 AATCCATGCTTGCTTGCAAAGTTGTAAACCAGTAAACGAGCGTCGCTTTTATTTCCATTCTTCAAGGAGT 1174650
1174651 GCTGTATGAGTCTATAAACCAGTCAGGAGCTTGCCTCTTTCTTAGGGCCGAACGAGAATGCCGCTCGCAA 1174720
1174721 AGCTGCGAAACGTGGTGCTGGAGTACGCGGCCATAGCCATCTACGTCAGGTAATTTTGCTTAAGACGCGA 1174790
1174791 CTGTTCTGTGAAACTGACGAGCTCAGGAAATCGGCTGGGCCGAACCACCATGCGTCTCCCGTCCAAAGC 1174860
1174861 GTTCTTGCGCACCCCCTCCCCCGCCCAAGCTCTCGCCCCGCTGCCACACGCCCTGCAACCCCAAGCCTCC 1174930
1174931 AACCCCCAAACCCCCATCCTCTCCACAGCGCCATCTACACCTCGGTGGTGCTGCTGCCCTCGGCGCTCGC 1175000
1175001 GCTGTTCTACCTGTTTGGGGCCACCAGCCCCTCGGCCTGGCTGCTGCTAGCCGCCTTCCTGGCCCTCACC 1175070
1175071 TTCACGCCGCTGCAGCTGACCACCGGTGCGCTGTCGGAGCGGTTCGTGCAGTTCAGTGTGGCGCGGGCGG 1175140
1175141 CGGCCTACTTCCCCACCCGCGTGGTGGTCACGGACCCGGAGGTGAGGGCGCTGTGGGGCGCTGTACGGG 1175210
1175211 GGGCTGCTGGGGGTGGGGGGCGAAGGTTGTGGGGGCCGGACCTGTGGGGAAAGGGGGAGGAGTAGTCTGG 1175280
1175281 GGTCACGAGGGAGGAGACAGGGGGCGGGGCTGCACGGTTAAGGCAGTGGAAACTGGGTAAGAGCATCGGG 1175350
1175351 AACAGGGAACGGTGGGCAGTGCATCAGGCGTAGGTGAGTGGTTGCGTGCCGATGACCGGAGCAGGTGGGG 1175420
1175421 AAGGCGGGGTTTATTGCACTCCCAAAAGAAACCAAGACCCGGAACCAGCCCACAAAGGGTATCGTAGTGG 1175490
1175491 CATCGGGTTGAACGGCGACACCACCGCCCTGCATTGGCTTTGGCATTGACTGCGGTCCTGTGCCCTCCCC 1175560
1175561 CCCCCCAGGCCTTCCGCACTGACCGCGGCTACTTGTTCGGATTCTGCCCGCACTCGGCTCTGCCCATCGC 1175630
1175631 ACTGCCCATCGCCTTCGCCACCACCTCGCCGCTGCTGCCCAAGGAGCTGCGCGGCCGCACACACGGCTTG 1175700
1175701 GCGTCGTCCGTGTGCTTCAGCGCGCCCATAGGTGTGTGTGGCGGGGGGGCGGCGCGGGGGGAGGATGGG 1175770
1175771 CCGGGAGAGCACCCGGTGACAGGTTGGTGGTGTGGCGGGTTGTTCTCCGGGTAGGTGGCGAAGCCGTCCT 1175840
1175841 GTGCTCTCCACCGCTACCGCGACTGCTACCGTGGCTGCTCCCCAGAACATCACCCACATGTGTGTTCCCT 1175910
1175911 CTCCTGCTCCTCCTACGCCTCCCTCCTCCTCCTCCCTCCCCACGTGCTGCAGTGCGGCAGCTGTACTGGT 1175980
1175981 GGCTGGGCGTGCGGCCCGCCACGCGGCAGAGCATCAGCGGCCTGTTGCGGGCGCGCAAGGTGGCGGTGCT 1176050
1176051 GGTGCCGGGGGGCGTGCAGGAGGTGCTCAACATGGAGCACGGCAAGGAGGTGTGTGCGGCTGGGGTGTGT 1176120
1176121 GTGTCGTGTGCGTGTGCGTGTGTGTTAGGAAAGCGCAAAGGAGAGGGCCGACACCGTGCTTGCAAAATGC 1176190
1176191 AGCAAGAAAGCAAGCGTTTTGTGTGTGACAAGAGAAACGAACGAGTGCGTGTGTGTGTGTGTGTTAAA 1176260
1176261 CACAAAAACAAACGGAACAAAGCCGCTGTGTGTGTGTGTGTGTGTGTGGCGTCGTTAGGCGTTGTTTG 1176330
1176331 GTATAATGTTCGGTGAGCGTGTGAGGTTGCGCGGCAACCTTACGGTATGTGGGGTTGGCGAGATTCAATG 1176400
1176401 CAAACAGCGCACTGTGACGCCGCATGGAGAGCTCTGCACAGCATTGCTAGCATACAACCATCACCCTGGC 1176470
1176471 CCTCACACTGCTTGGCCCCCCCTTTGACAATTGGGACCTACATGGTTGGGCTCGAACATTTAACCACCCT 1176540
1176541 GTGGACGGGTTCTGGGTCTTGGCTTCTTTGGGATTGGAATACGCTACCTCCCCCGCTTCGCTAGTTTGGC 1176610
1176611 TTGGTTTGGTGTAGTTTGGCCTGGTACAATCCCCCCGCACACACATGCACACACGTACACTCACACACAC 1176680
1176681 ACACAATGCCCCCCCCCCCGCACAAACAGGTGGCCTACCTCTCCAGCCGCACCGGCTTCGTGCGACTGGC 1176750
1176751 CGTGCAGCACGGCGCGCCGCTGGTGCCAGTGTGGGCGTTCGGCCAGACGCGCGCGTACAGCTGGTTCCGG 1176820
1176821 CCGGGGCCGCCGCTCGTGCCCACGTGGCTCGTGGAGCGCATCTCACGTGCCGCCGGCGCCGTACCCATCG 1176890
1176891 GCATGTTTGGGCAGTACGGCACGCCCATGCCGCACCGCGAGCCCCTCACCATTGTGGTGGGTCGCCCCAT 1176960
```

```
1176961 CCCGGTGCCGGAGCTGGCGCCGGGCCAGCTCGAGCCCGAGCCCGAGGTGCTGGCGGCGCTCCTCAAGCGC 1177030
1177031 TTCACGGACGACCTGCAGGTGTGCGCGCGCGCGTGCGTGTGCCTGTGTTAAATAAAGGAAACGAAAGCCC 1177100
1177101 GTGTGTGCGTGTGTGTGTGTATGTGTGTGTGTGTGTGTGTGCGTGTGTGTCTGTGTGTGTGTGTGTGT 1177170
1177171 GTGTGTGTGTGTGTGTGTGTGTGTGTGTGTGTGTGTGTGTGTGTGTGTGCGTGCGTGTGTCT 1177240
1177241 GTGTGTGGAGGTAGGAGATGGGGAGCACGGGAAGGCAGTCACGATGAGTGGATTACGGCATGCGCTGGCG 1177310
1177311 GCCAGTCGTGCCACTTGTGTCCCAAAGAGAAAGGACTGCTGTTTTACTGCCACTGCAATCATTGACACAC 1177380
1177381 ACGCACACATTCACACACATACACACACGCACACACGCGCACACACACACACACACATACCTCTTCTG 1177450
1177451 GCCCGCACAGGCGCTGTACGACAAGCACAAGGCGCAGTTCGGCAAGGGCGAGGAGCTGGTCATAATGTAG 1177520
1177521 GCGCGGGGAGGCGGGGCCGGGGAGGTGTGGTGGATGGGTGGTGGTGGTGGGGCGCTGGTGCCGTGGT 1177590
1177591 TGTGTGGGGAGAGGGCGCAGCGCAGGTTATTGCGGCTGCGCCGTGAGAGGTTGACCGGTAAAGAAGCAGG 1177660
1177661 TGTGCCGGGCACCAGGAGTTCTAAATTCTCATTTTTGTACGGCCCACTCGGCAGAAAGCTAGCGTATAGA 1177730
1177731 GAGGCAAAGAGCGGAAGCAGGTGGTGAGGGAAAGAACTGAATGCTGATGTCTCAAGACTAAAACTGTTAG 1177800
1177801 TGCTGGTGTGGAAGGCTGGAGCCCGGAGGGCACGTGTATGTGGCGTGAGTGCATTTGCCAGATGGAAGGT 1177870
1177871 GGAGTGGTTGCACCGGTGCCTCCTAATGGTGGTGTGGAACCTAGCTGTCGCGGGTGTTTGACATGCATGC 1177940
1177941 AAGGCCGGGTGCATTAAGCCCAGTGGACCGCAAGCGGTTCGATGCAGCAACACGTGCAAGCCAGGCTTGA 1178010
1178011 GCTGTCACTCACGTCAGTGCCCCCTTCACCGCACATGCTTACAAGCTCAGATTCGCTTGACAGGGAGTTG 1178080
1178081 CTAGGCAACGCACAGGGAGCCAACAAGTAAAACCGTGCACAGTCGCACATAGCTTGCGCTTACACGCATA 1178150
1178151 CGGTATTGGCGGCGTCGGCCTCATCGGCCTGCTGACACACCATGCATCCCCGGATACCGGCGGATGCACC 1178220
1178221 CACATGACCTCCCTGCCGCCTTTCAGCGTTTATGTACAGCCCCGTCCTTTGCACACGCACGTGGCTGCAG 1178290
1178291 GCCCTGTAGTCGACACAGCCTGACACGCACCCCATGCACATGCGGGAGGTCTTCGCTGGGGTTCGGTCCG 1178360
1178361 ATTCCTCCTTCCCAAACAGCCACGCAACACCGTGTCCGTGCCCCACCTGATTCGCCGTGCTGACACGCCC 1178430
1178431 GCTCCTACAGTCCCC 1178445
```

*Fig. 10B*

Transcript sequence
```
   1 TTCAAGGAGTGCTGTATGAGTCTATAAACCAGTCAGGAGCTTGCCTCTTTCTTAGGGCCGAACGAGAATG   70
  71 CCGCTCGCAAAGCTGCGAAACGTGGTGCTGGAGTACGCGGCCATAGCCATCTACGTCAGCGCCATCTACA  140
 141 CCTCGGTGGTGCTGCTGCCCTCGGCGCTCGCGCTGTTCTACCTGTTTGGGGCCACCAGCCCCTCGGCCTG  210
 211 GCTGCTGCTAGCCGCCTTCCTGGCCCTCACCTTCACGCCGCTGCAGCTGACCACCGGTGCGCTGTCGGAG  280
 281 CGGTTCGTGCAGTTCAGTGTGGCGCGGGCGGCGGCCTACTTCCCCACCCGCGTGGTGGTCACGGACCCGG  350
 351 AGGCCTTCCGCACTGACCGCGGCTACTTGTTCGGATTCTGCCCGCACTCGGCTCTGCCCATCGCACTGCC  420
 421 CATCGCCTTCGCCACCACCTCGCCGCTGCTGCCCAAGGAGCTGCGCGGCCGCACACACGGCTTGGCGTCG  490
 491 TCCGTGTGCTTCAGCGCGCCCATAGTGCGGCAGCTGTACTGGTGGCTGGGCGTGCGGCCCGCCACGCGGC  560
 561 AGAGCATCAGCGGCCTGTTGCGGGCGCGCAAGGTGGCGGTGCTGGTGCCGGGGGGCGTGCAGGAGGTGCT  630
 631 CAACATGGAGCACGGCAAGGAGGTGGCCTACCTCTCCAGCCGCACCGGCTTCGTGCGACTGGCCGTGCAG  700
 701 CACGGCGCGCCGCTGGTGCCAGTGTGGGCGTTCGGCCAGACGCGCGCGTACAGCTGGTTCCGGCCGGGGC  770
 771 CGCCGCTCGTGCCCACGTGGCTCGTGGAGCGCATCTCACGTGCCGCCGGCGCCGTACCCATCGGCATGTT  840
 841 TGGGCAGTACGGCACGCCCATGCCGCACCGCGAGCCCCTCACCATTGTGGTGGGTCGCCCCATCCCGGTG  910
 911 CCGGAGCTGGCGCCGGGCCAGCTCGAGCCCGAGCCCGAGGTGCTGGCGGCGCTCCTCAAGCGCTTCACGG  980
 981 ACGACCTGCAGGCGCTGTACGACAAGCACAAGGCGCAGTTCGGCAAGGGCGAGGAGCTGGTCATAATGTA 1050
1051 GGCGCGGGGAGGCGGGGCCGGGGAGGTGTGGTGGATGGGTGGTGGTGGTGGGGCGCTGGTGCCGTGG 1120
1121 TTGTGTGGGGAGAGGGCGCAGCGCAGGTTATTGCGGCTGCGCCGTGAGAGGTTGACCGGTAAAGAAGCAG 1190
1191 GTGTGCCGGGCACCAGGAGTTCTAAATTCTCATTTTTGTACGGCCCACTCGGCAGAAAGCTAGCGTATAG 1260
1261 AGAGGCAAAGAGCGGAAGCAGGTGGTGAGGGAAAGAACTGAATGCTGATGTCTCAAGACTAAAACTGTTA 1330
1331 GTGCTGGTGTGAAGGCTGGAGCCCGGAGGGCACGTGTATGTGGCGTGAGTGCATTTGCCAGATGGAAGG 1400
1401 TGGAGTGGTTGCACCGGTGCCTCCTAATGGTGGTGTGGAACCTAGCTGTCGCGGGTGTTTGACATGCATG 1470
1471 CAAGGCCGGGTGCATTAAGCCCAGTGGACCGCAAGCGGTTCGATGCAGCAACACGTGCAAGCCAGGCTTG 1540
1541 AGCTGTCACTCACGTCAGTGCCCCCTTCACCGCACATGCTTACAAGCTCAGATTCGCTTGACAGGGAGTT 1610
1611 GCTAGGCAACGCACAGGGAGCCAACAAGTAAAACCGTGCACAGTCGCACATAGCTTGCGCTTACACGCAT 1680
1681 ACGGTATTGGCGGCGTCGGCCTCATCGGCCTGCTGACACACCATGCATCCCCGGATACCGGCGGATGCAC 1750
1751 CCACATGACCTCCCTGCCGCCTTTCA 1776
```

*Fig. 11*

Protein sequence
MPLAKLRNVVLEYAAIAIYVSAIYTSVVLLPSALALFYLFGATSPSAWLLLAAFLALTFTPLQLTTGALSERFVQFSVAR
AAAYFPTRVVVTDPEAFRTDRGYLFGFCPHSALPIALPIAFATTSPLLPKELRGRTHGLASSVCFSAPIVRQLYWWLGVR
PATRQSISGLLRARKVAVLVPGGVQEVLNMEHGKEVAYLSSRTGFVRLAVQHGAPLVPVWAFGQTRAYSWFRPGPPLVPT
WLVERISRAAGAVPIGMFGQYGTPMPHREPLTIVVGRPIPVPELAPGQLEPEPEVLAALLKRFTDDLQALYDKHKAQFGK
GEELVIM

*Fig. 12*

DGTT5

Assigned name: CHLRE2_KG.SCAFFOLD_7000128
Protein ID: 141301
Location: Chlre3/scaffold_7:877811-880673

Genomic sequence
```
877611 CCTGCAGTGGCAAGGGCTGCAAGGAGGCAGCGGCAGCGCCAGCACGCGATGGCGGCGCTGCCTGCGCCGC 877680
877681 CCCCATAACCGCCACTACTGCCACCATCACCACTACCACCGCCACTGCAATCAACGCCACCACAACTGTT 877750
877751 GCCGCCACCGCGCATTCCCCGCGCCCCCGCCCGGGCCCGGGCCCGCCAAAGCTGGTGGTGATGACCCCGC 877820
877821 GGGATCCGCCGGTGCCGCGGCCGCCGCCGGGCGTACGGCAGTACACTGACGGCCGGTCGGCGTCGTACGT 877890
877891 ACTGCCGCTGCCGTATCGCCTGCTGGCCCAGGTGGGTGTGACATTGACACGTTGCTGAACTTGCTACAGC 877960
877961 ACAAGGATGTCCACATGTGTTCGGTTGGCCCACGGCGCACGCGCACACGCTTGTCCTCGTATCTTCCTGA 878030
878031 GTCCACGCTCCTTCGCCTCTGACAGACTTACACGCACCCCATTGTCTAAGCCGGCTCTCCGAGACCACCC 878100
878101 TGACTAGCGCCCTCCCTCCCGCCGCGATTGCAGCTGACTCTGGGTTTGTACGTGGGCTTTCCCTACATCC 878170
878171 TGCTGGGGTTGTTGCTGGGCACGGCTGCCGGCTCGCGCGCCGCCGCCGCCGCCCTGGCTCTGACGCTGGG 878240
878241 CAGCCTGCTGGTGCCGGCCCCACCGCACATCCGGCAGGGCATGCTGGACTCGGCACTGTTCAGGTGGGTG 878310
878311 GCTGCGTGGAGGTGGGTGGAGGTTAGAGCGAGATGACCAACCCCATGGGCTTCGCTTGTGTGGAATGCGC 878380
878381 CCTGCGTGTACGGGGTATCTACCTGCTTCCGACCTCTTGCCTTGCGCCCCCGCCCCAACCCTGCCCGCCT 878450
878451 CGAACCCTGCTGCCTCCTCGCCCCTGCCCCGCCCCGCCCCGCCCCAGGCTGTGGCGCGCCTACTTCAACT 878520
878521 ACAGCTACGCCTACGACCAACTGCCCGACTTCAACCGCCCACACATCTTTGTCAACAGCCCGCACGGCGC 878590
878591 CTTCCCGCTGTCGCAGGTAGGTGGGGGCGTGTGCGTGTGCAAGTGTGTACATGCAGGGTCGCTGGCCGGG 878660
878661 TGCACGTGTGCTATAGCCTACAGGGTGACGGGGTTAGACGGCTGCCAACCTCCAAAACACTCCCAGGCCC 878730
878731 TGGGGGCTTCGTGGGTCCCATTCCATTACCCCTCCCCCACAGCCCTCACCACGCGCCTCACCCCCCACCTG 878800
878801 CCACACCCCCACCTTCCGCACCCCCACCTGCCGCACCCCCACAGATCCTGTGCATCTCCCTGTCCAACAT 878870
878871 CGTGTGGCCGGGCTTCCCCGTGCACAGCCTGGCGGCCTCGGTGCTGTGGTACATACCGCTGTGGCGCCAC 878940
878941 ATGAAGGCGGCGCTGGGGGCCGCGCCCGCCAGCCGGGACAACGCGCGCATGCTGCTGAGGCACCGCGGGT 879010
879011 GGGCGGGCGTGGCGTGGCGTGGCGTGTAATGGAATGTGCAACCGGGAGGGCTGTTGCGTGTGCAGTACAG 879080
879081 TATTACACGGTGTCACAATAGCAGTCAGCTGGTGCGGTAATGTTGCAGTCGGAAGAAGGTGCTATAACAC 879150
879151 AGCCTACTAGAGCTAGAGTAGGCCGACGGCGTTGCAGGCGGCGCGCCCCCGGGGTACAGAGCAGGGTGAT 879220
879221 CGTTCTTCCACGTCACTGGCCCTTGAACTGCGTCAGCAGGTCCCTATTATAACCAACGCAGTCTATAACA 879290
879291 CACTCAGCGTGCCGATGCGCATGCAGGTCGGTGGCGGTGCTGGCGGGCGGCATTGCGGAGATGTACACGT 879360
879361 CATCGCCCTCCCGCGCCGCCGCTGCCACCGAACCAGATGAGGCTGCGGCTGCGGGTGGGGCGATCGACAC 879430
879431 GACTGAAGCCGCCGGCGCCACCGGCTCAAGCAGCACCACCACTAGCCCGCCGCAGCCAAAGGAGCAGCAG 879500
879501 CGCGATGGGGAGCAGCGCCAGGGGCCGCGCAAGGGGCTGAAGGGGCTGCTGAAAGGCCCGAAGGACGATC 879570
879571 CCGATCCGGCGGCGGAGGAGGAGCAGGGCCTCGGGTTGGCACCTGAACGCATCAAGCTGCTGGGCCGGCG 879640
879641 CGGCTTCGTGCGGCTGGCGGTGGAGATGGGTGTGCCCATTGTACCCATATACCACATGGGCAACAGCAAG 879710
```

*Fig. 13A*

```
879711 GTGTGTGTGCGTGTGTGTGTGTGTGTGTGTTTGTGCGTGTGTGTATGTGTGTGTGTGTGTAAGTGTGTCT 879780
879781 TTGTGTGTGTGTGTGTGTGTGTGTGTGTGTGTGTAAGTGTGTCTTTGTGTGTGTGTGTGTGTGAGTGT 879850
879851 GTGTGTGTGTGTGTGTGTGTGAGTGTGTGTGTGTGTAAGTGTGTCTTTGTGTGTGTGTGTGTGTGTGT 879920
879921 GTACGGCGCGGCAGGGATGGGTGAAGCGCCTTGAGAGGGAGGAAGTAGGCGCAGGCAGGGAAGCGGCCAA 879990
879991 GCGGGTGCGCGCTCCAGTTGCTCCATGCAGTTGACTGACCTCACGGCACACTTGGTGAGTTGGCCCTTCC 880060
880061 TAAGCGCCACCTGCGCCGCCTGTGCCCTGCAGATCCTGACCTTCGGGCCGCAGTCACTGCAGCAGCTGTC 880130
880131 GCGCCGCCTGCGCATGGCGCTGGGCGCCGTGTTCGGTGAGTCCTGGCCTTCTTGCCCTGCCCCCCTAGTG 880200
880201 CAATGCTAGTGGGACTTTTGAGCGCCCCACGCCCCACGCCTGACGCCCCTCTCCCCTTCCATTGCTCGTT 880270
880271 CAACCCGTGCTTGAATGCTTGCCGTGCAAATGCGCGTACTCCACGGCGGCGCCATACGCCCAAGTGCCCG 880340
880341 GCGCTTCCCCCGATTGGGACCTGTTCCTTCGGGCTCGGACAAGTACCCTTCCCTCCCTCCTTCCCCACCC 880410
880411 CAGCCCTTACCCCCCTCACCGCCTCATGCCCCGCTTCAAACAGGCGTGTGGGGCCTGCCTGTGCCGCGCC 880480
880481 CCCAGCCGCTCATGATGTGTGTGGGCAGCCCCATTCCCGTGCCGTACGTGGATCCAGCCGCCGAGCCGGA 880550
880551 GCGCTTCGAGGCCGTGGTGGCGGCGGTGCACGGGCAGGTGGTGGCGGCCTTTCAGGATCTGTACAACAGG 880620
880621 TACCGCGTGCAGTACGGCTGCGGTTGGGAGCGCCGGCCGCTGGAGGTGTGCTGAGCCAACCGCCGGGTGC 880690
880691 GGTGGCGTGTGTGCGAGGCGTGTTGAGGTGTATGAGCGTGGGAGTGGCTGATTGGCACATGCGAGTGAGG 880760
880761 GGTTGGCGGGGAAGAGCTCGAGGCGATTGGGCACCGCCGCCAGGTGATGAATGCAGCTTTGGAGTTTCCA 880830
880831 AGGAACTGAGGGGCTGGCGGCTGGCGGCGGCACGGCTAAAGGT 880873
```

Fig. 13B

Transcript sequence
```
    1 ATGACCCCGCGGGATCCGCCGGTGCCGCGGCCGCCGCCGGGCGTACGGCAGTACACTGACGGCCGGTCGG   70
   71 CGTCGTACGTACTGCCGCTGCCGTATCGCCTGCTGGCCCAGCTGACTCTGGGTTTGTACGTGGGCTTTCC  140
  141 CTACATCCTGCTGGGGTTGTTGCTGGGCACGGCTGCCGGCTCGCGCGCCGCCGCCGCCGCCCTGGCTCTG  210
  211 ACGCTGGGCAGCCTGCTGGTGCCGGCCCCACCGCACATCCGGCAGGGCATGCTGGACTCGGCACTGTTCA  280
  281 GGCTGTGGCGCGCCTACTTCAACTACAGCTACGCCTACGACCAACTGCCCGACTTCAACCGCCCACACAT  350
  351 CTTTGTCAACAGCCCGCACGGCGCCTTCCCGCTGTCGCAGATCCTGTGCATCTCCCTGTCCAACATCGTG  420
  421 TGGCCGGGCTTCCCCGTGCACAGCCTGGCGGCCTCGGTGCTGTGGTACATACCGCTGTGGCGCCACATGA  490
  491 AGGCGGCGCTGGGGGCCGCGCCCGCCAGCCGGGACAACGCGCGCATGCTGCTGAGGCACCGCGGGTCGGT  560
  561 GGCGGTGCTGGCGGGCGGCATTGCGGAGATGTACACGTCATCGCCCTCCCGCGCCGCCGCTGCCACCGAA  630
  631 CCAGATGAGGCTGCGGCTGCGGGTGGGGCGATCGACACGACTGAAGCCGCCGGCGCCACCGGCTCAAGCA  700
  701 GCACCACCACTAGCCCGCCGCAGCCAAAGGAGCAGCAGCGCGATGGGGAGCAGCGCCAGGGGCCGCGCAA  770
  771 GGGGCTGAAGGGGCTGCTGAAAGGCCCGAAGGACGATCCCGATCCGGCGGCGGAGGAGGAGCAGGGCCTC  840
  841 GGGTTGGCACCTGAACGCATCAAGCTGCTGGGCCGGCGCGGCTTCGTGCGGCTGGCGGTGGAGATGGGTG  910
  911 TGCCCATTGTACCCATATACCACATGGGCAACAGCAAGATCCTGACCTTCGGGCCGCAGTCACTGCAGCA  980
  981 GCTGTCGCGCCGCCTGCGCATGGCGCTGGGCGCCGTGTTCGGCGTGTGGGGCCTGCCTGTGCCGCGCCCC 1050
 1051 CAGCCGCTCATGATGTGTGTGGGCAGCCCCATTCCCGTGCCGTACGTGGATCCAGCCGCCGAGCCGGAGC 1120
 1121 GCTTCGAGGCCGTGGTGGCGGCGGTGCACGGGCAGGTGGTGGCGGCCTTTCAGGATCTGTACAACAGGTA 1190
 1191 CCGCGTGCAGTACGGCTGCGGTTGGGAGCGCCGGCCGCTGGAGGTGTGCTG 1241
```

*Fig. 14*

Protein sequence
MTPRDPPVPRPPPGVRQYTDGRSASYVLPLPYRLLAQLTLGLYVGFPYILLGLLLGTAAGSRAAAAALALTLGSLLVPAP
PHIRQGMLDSALFRLWRAYFNYSYAYDQLPDFNRPHIFVNSPHGAFPLSQILCISLSNIVWPGFPVHSLAASVLWYIPLW
RHMKAALGAAPASRDNARMLLRHRGSVAVLAGGIAEMYTSSPSRAAAATEPDEAAAAGGAIDTTEAAGATGSSSTTTSPP
QPKEQQRDGEQRQGPRKGLKGLLKGPKDDPDPAAEEEQGLGLAPERIKLLGRRGFVRLAVEMGVPIVPIYHMGNSKILTF
GPQSLQQLSRRLRMALGAVFGVWGLPVPRPQPLMMCVGSPIPVPYVDPAAEPERFEAVVAAVHGQVVAAFQDLYNRYRVQ
YGCGWERRPLEVC

*Fig. 15*

ENZYME DIRECTED OIL BIOSYNTHESIS IN MICROALGAE

This invention was made with government support under FA9550-07-1-0212 awarded by the United States Air Force Office of Scientific Research. The government has certain rights in the invention.

RELATED APPLICATION

This application is a continuation of and claims the benefit of priority under 35 U.S.C. §120 to U.S. patent application Ser. No. 12/639,304, filed on Dec. 16, 2009, which claims priority to U.S. Provisional Application Ser. No. 61/138,716, filed on Dec. 18, 2008, which are hereby incorporated by reference herein in their entirety.

FIELD OF THE INVENTION

The present invention is related to biosynthetic oil compositions and methods of making thereof. In some embodiments, the invention relates to the use of endogenous enzymes in plants capable of synthesizing oil. In preferred embodiments, said plants are algae. In further embodiments, said algae are from the family *Chlamydomonas, Nannochloropsis, Dunaliella, Chlorella* and *Scenedesmus*. In still further embodiments, said endogenous enzymes are diacylglycerol acyltransferases.

BACKGROUND

The biosynthesis of oil in algae holds significant promise as a primary source for food oils, biodiesel and industrial chemicals. Algal oil biosynthesis is carried out naturally using a myriad of endogenous enzymes. However, neither the appropriate biomolecular targets nor the conditions for promoting the enhanced production of algal oils at levels have yet been identified. Thus, there is a need for reliable, large-scale oil production based on biosynthetic platforms.

SUMMARY OF THE INVENTION

The present invention is related to biosynthetic oil compositions and methods of making thereof. In some embodiments, the invention relates to the use of endogenous enzymes in plants capable of synthesizing oil. In preferred embodiments, said plants are algae. In further embodiments, said algae are from the family *Chlamydomonas, Nannochloropsis, Dunaliella, Chlorella* and *Scenedesmus*. In still further embodiments, said endogenous enzymes are diacylglycerol acyltransferases.

In one embodiment, the present invention comprises a method comprising: a) providing: i) algae (or other host), and ii) a vector comprising an algae gene encoding a diacylglycerol acyltransferase operably linked to a promoter (e.g. an inducible promoter, a heterologous promoter, etc.); and b) transfecting said algae (e.g. algae cells) with said vector under conditions such that said diacylglycerol acyltransferase is expressed. In a preferred embodiment, said expression is under conditions such that TAG, free fatty acid, and/or DAG is/are produced (and ideally increased in algae cells) and recovered (e.g. collected or extracted from the algae and/or oil from said algae). In a preferred embodiment, said expression is ectopic. The present invention also contemplates, as a composition, the transfected algae produced in this manner. In further embodiments, said expression of said gene is upregulated between 1.5-3 fold relative to the levels of said gene expression under native, wild type conditions. In still further embodiments, said expression of said gene is upregulated between 3.5-5 fold relative to the levels of said gene expression under native, wild type conditions. In additional embodiments, said expression of said gene is upregulated between 5.5-7 fold relative to the levels of said gene expression under native, wild type conditions. In some embodiments, said expression of said gene is upregulated between 7.5-10 fold relative to the levels of said gene expression under native, wild type conditions. In further embodiments, said method further comprises step (e) collecting the fatty acid, thereby forming a biosynthetic oil. In further embodiments, said algae is selected from the group consisting of *Chlamydomonas, Nannochloropsis, Dunaliella, Chlorella* and *Scenedesmus*. In still further embodiments, said algae is *Chlamydomonas reinhardtii*.

In some embodiments, the invention relates to a method comprising: providing a rutabaga, and a vector comprising an algae gene encoding a diacylglycerol acyltransferase operably linked to a promoter, and transfecting said rutabaga with said vector under conditions such that said diacylglycerol acyltransferase is expressed.

In some embodiments, the invention relates to nucleic acid encoding an algae diacylglycerol acyltransferase. In another embodiment, the nucleic acid is in a vector. Preferably, said nucleic acid sequence encoding a diacylglycerol acyltransferase operably linked to a promoter (e.g. homologous or heterologous). In one embodiment, said nucleic acid sequence comprises SEQ ID NO:2 (DGTT1). In one embodiment, said nucleic acid sequence comprises SEQ ID NO:5 (DGTT2). In additional embodiments, said nucleic acid sequence comprises SEQ ID NO:8 (DGTT3). In some embodiments, said nucleic acid sequence comprises SEQ ID NO:11 (DGTT4). In further embodiments, said nucleic acid sequence comprises SEQ ID NO:14 (DGTT5). In still further embodiments, said algae is an algae species is derived from a genus selected from the group consisting of *Chlamydomonas, Nannochloropsis* and *Dunaliella*. In additional embodiments, said algae species comprises *Chlamydomonas reinhardtii*.

Expression in heterologous systems is also contemplated. In some embodiments, the present invention contemplates DGTT genes in other species (e.g. other plants), host cells or vectors. In one embodiment, said species is *Brassica napobrassica*. In one embodiment, the present invention contemplates DGTT genes in a shuttle vector, e.g. a yeast shuttle vector, capable of functioning in both yeast and bacteria. In one embodiment, the present invention contemplates yeast, e.g. yeast cells, comprising one or more algae DGTT genes. In one embodiment, the present invention contemplates a method of making TAG, free fatty acid, and/or DAG in a non-algae host (e.g. yeast) comprising transforming said host with a vector comprising an algae DGTT under conditions such that TAG, free fatty acid, and/or DAG is produced.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "upregulated" as used herein, should be interpreted in the most general sense possible. For example, a special type of molecule may be "upregulated" in a cell if it is produced at a level significantly and detectably higher (i.e., for example, between 1.5-10 fold) than the natural expression rate.

The term "ectopic expression" as used herein, refers to the expression of a gene in an abnormal place in an organism.

The term "plant" is used in it broadest sense. It includes, but is not limited to; any species of woody, ornamental or decorative, crop or cereal, fruit or vegetable plant, and photosynthetic green algae (for example, *Chlamydomonas reinhardtii*). It also refers to a plurality of plant cells that are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (for example, single cells, protoplasts, embryos, callus, etc.). Plant tissue may be in planta, in organ culture, tissue culture, or cell culture. The term "plant part" as used herein refers to a plant structure or a plant tissue.

The term "crop" or "crop plant" is used in its broadest sense. The term includes, but is not limited to, any species of plant or algae edible by humans or used as a feed for animals or used, or consumed by humans, or any plant or algae used in industry or commerce.

The term "oil-producing species" refers to plant species that produce and store triacylglycerol in specific organs, primarily in seeds. Such species include, but are not limited to, green algae (*Chlamydomonas reinhardtii*), soybean (*Glycine max*), rutabaga (*Brassica napobrassica*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling *Brassica* species, and *Arabidopsis thaliana*, and wild species which may be a source of unique fatty acids.

The term "*Chlamydomonas*" refers to a plant or plants from the genus *Chlamydomonas*. Non-limiting examples of *Chlamydomonas* include plants from the species *C. reinhardtii*. The term also refers to *C. reinhardtii* algae from which nucleic acid sequence SEQ ID NOs: 1-15 were isolated.

The term plant cell "compartments or organelles" is used in its broadest sense. The term includes, but is not limited to, the endoplasmic reticulum, Golgi apparatus, trans Golgi network, plastids, sarcoplasmic reticulum, glyoxysomes, mitochondrial, chloroplast, and nuclear membranes, and the like.

The term "host cell" refers to any cell capable of replicating and/or transcribing and/or translating a heterologous gene.

The terms "diacylglycerol" and "diglyceride" refer to a molecule comprising a glycerol backbone to which two acyl groups are esterified. Typically, the acyl groups are esterified to the sn-1 and sn-2 positions, although the acyl groups may also be esterified to the sn-1 and sn-3 positions, or to the sn-2 and sn-3 positions; the remaining position is unesterified and contains a hydroxyl group. This term may be represented by the abbreviation DAG.

The terms "triacylglycerol" and "triglyceride" refer to a molecule comprising a glycerol backbone to which three acyl groups are esterified. This term may be represented by the abbreviation TAG.

The term "long chain triacylglycerol" refers to a triacylglycerol in which all three acyl groups are long chain, or in other words each chain is a linear aliphatic chain of 6 carbons or greater in length (an acyl group may be referred to by the letter C followed by the number of carbons in the linear aliphatic chain, as, for example, C6 refers to an acyl group of 6 carbons in length). This term may be represented by the abbreviation LcTAG.

The terms "acetyl glyceride" and "acetyl triacylglycerol" and the like refer to a triglyceride to which at least one acetyl or related group is esterified to the glycerol backbone. A particular acetyl glyceride is denoted by the position(s) to which an acetyl or related group is esterified; thus, "sn-3-acetyl glyceride" or "1,2-diacyl-3-acetin" refers to triacylglycerol with an acetyl group at the sn-3 position. These terms may be represented by the abbreviation AcTAG.

An "acetyl" or "related group", when used in reference to AcTAG, refers to an acyl moiety other than a long-chain acyl group esterified to TAG. The acyl moiety is any linear aliphatic chain of less than 6 carbons in length; it may or may not have side group chains or substituents. The acyl moiety may also be aromatic. Related group members include but are not limited to propionyl and butyryl groups, and aromatic groups such as benzoyl and cinnamoyl.

The term "diacylglycerol acyltransferase" (DGAT or DGTT) refers to a polypeptide with the capacity to transfer an acyl group to a diacylglycerol substrate. Typically, a diacylglycerol acyltransferase transfers an acyl group to the sn-3 position of the diacylglycerol, though transfer to the sn-1 and sn-2 positions are also possible. The acyl substrate for the transferase is typically esterified to CoA; thus, the acyl substrate is typically acyl-CoA. The enzyme is therefore also referred to as an "diacylglycerol:acyl-CoA acyltransferase," and in some particular embodiments, as an "acyl-CoA:sn-1, 2-diacylglycerol acyltransferase," and the like. The term may be referred to by the abbreviation DAGAT.

The term "diacylglycerol acetyltransferase" refers to a diacylglycerol acyltransferase polypeptide with a unique acyl group transfer specificity, such that the polypeptide is able to transfer an acetyl or related group to a diacylglycerol substrate, and such that the diacylglycerol acetyltransferase exhibits increased specificity for an acetyl or related group compared to a diacylglycerol acyltransferase obtained from a plant in which acetyl TAGs are not present, or are present in only trace amounts (in other words, less than about 1% of the total TAGs). The specificity may be determined by either in vivo or in vitro assays. From an in vivo assay, the specificity is the proportion of total TAGs that are AcTAGs, where the AcTAGs are synthesized by the presence of a heterologous diacylglycerol acetyltransferase. From an in vitro assay, the specificity is the activity of transfer of an acetyl or related group to a diacylglycerol, when the substrate is an acetyl-CoA or related group esterified to CoA. The increase in specificity of transferring an acetyl or related group for an AcDAGAT is at least about 1.5 times, or about 2 times, or about 5 times, or about 10 times, or about 20 times, or about 50 times, or about 100 times, or up to about 2000 times, the specificity of a DAGAT obtained from a plant in which acetyl TAGs are not present, or are present in only trace amounts. One standard DAGAT to which an AcDAGAT is compared, in order to determine specificity of transfer of an acetyl or related group, is a DAGAT obtained from *Arabidopsis* (AtDAGAT), as described in Example 4.

The acetyl or related group substrate of the transferase is typically esterified to CoA; thus, typical acetyl substrate include but are not limited to acetyl-CoA, propionyl-CoA, butyryl-CoA, benzoyl-CoA, or cinnamoyl-CoA, as described above. These CoA substrates are typically non-micellar acyl-CoAs, or possess high critical micelle concentrations (CMCs), in that they form micelles at relatively high concentrations when compared to the CMCs of long chain acyl-CoAs.

The diacylglycerol substrate of AcDAGAT is typically a long chain diacylglycerol, although other groups are also contemplated. The acyl (or other) groups are esterified to the sn-1 and sn-2 positions, although the acyl groups may also be esterified to the sn-1 and sn-3 positions, or to the sn-2 and sn-3 positions.

Thus, the enzyme is also referred to as an "diacylglycerol: acetyl-CoA acetyltransferase," or in particular embodiments, as an "acetyl-CoA:sn-1,2-diacylglycerol acetyltransferase" and the like. This term may be referred to by the abbreviation AcDAGAT, indicating an activity of increased specificity for transfer of acetyl or related groups The terms "*Chlamydomonas*" and "*Chlamydomonas*-like" when used in reference to a DAGAT refer to a DAGAT obtained from *Chlamydomonas reinhardtii* or with a substrate specificity that is similar to a DAGAT obtained from *Chlamydomonas reinhardtii*. The term may be referred to by the abbreviation, "ChDAGAT," indicating an enzyme obtained from *Chlamydomonas reinhardtii*, or from the genus *Chlamydomonas*, or from a closely related plant family, or an enzyme which has an amino acid sequence with a high degree of similarity to or identity with a DAGAT obtained from *Chlamydomonas reinhardtii*. By "high degree of similarity" it is meant that it is more closely related to ChDAGAT than to AtDAGAT by BLAST scores or other amino acid sequence comparison/alignment software programs.

The term "substrate specificity" refers to the range of substrates that an enzyme will act upon to produce a product.

The term "competes for binding" is used in reference to a first polypeptide with enzymatic activity which binds to the same substrate as does a second polypeptide with enzymatic activity, where the second polypeptide is variant of the first polypeptide or a related or dissimilar polypeptide. The efficiency (for example, kinetics or thermodynamics) of binding by the first polypeptide may be the same as or greater than or less than the efficiency substrate binding by the second polypeptide. For example, the equilibrium binding constants ($K_D$) for binding to the substrate may be different for the two polypeptides.

The terms "protein" and "polypeptide" refer to compounds comprising amino acids joined via peptide bonds and are used interchangeably.

As used herein, "amino acid sequence" refers to an amino acid sequence of a protein molecule. "Amino acid sequence" and like terms, such as "polypeptide" or "protein," are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid.

The term "homology" when used in relation to amino acids refers to a degree of similarity or identity. There may be partial homology or complete homology (in other words, identity). "Sequence identity" refers to a measure of relatedness between two or more proteins, and is given as a percentage with reference to the total comparison length. The identity calculation takes into account those amino acid residues that are identical and in the same relative positions in their respective larger sequences. Calculations of identity may be performed by algorithms contained within computer programs.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences include those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferable greater than 75% sequence identity, and still more preferably greater than 90% sequence identity, with a reference sequence.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties (for example, replacement of leucine with isoleucine). More rarely, a variant may have "non-conservative" changes (for example, replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (for example, DNA or RNA) sequence that comprises coding sequences necessary for the production of RNA, or a polypeptide or its precursor (for example, proinsulin). A functional polypeptide can be encoded by a full-length coding sequence or by any portion of the coding sequence as long as the desired activity or functional properties (for example, enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "heterologous gene" refers to a gene encoding a factor that is not in its natural environment (in other words, has been altered by the hand of man). For example, a heterologous gene includes a gene from one species introduced into another species. A heterologous gene also includes a gene native to an organism that has been altered in some way (for example, mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (for example, genes expressed in loci where the gene is not normally expressed).

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "an oligonucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in cDNA, genomic DNA or RNA form. When present in a DNA form, the oligonucleotide may be single-stranded (in other words, the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "complementary" and "complementarity" refer to polynucleotides (in other words, a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" when used in relation to nucleic acids refers to a degree of complementarity. There may be partial homology or complete homology (in other words, identity). "Sequence identity" refers to a measure of relatedness between two or more nucleic acids, and is given as a percentage with reference to the total comparison length. The identity calculation takes into account those nucleotide residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (in other words, the hybridization) of a sequence that is completely homologous to a target under conditions of low stringency. This is not to say that conditions of low stringency are such that non-specific binding is permitted; low stringency conditions require that the binding of two sequences to one another be a specific (in other words, selective) interaction. The absence of non-specific binding may be tested by the use of a second target which lacks even a partial degree of complementarity (for example, less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed. Numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (for example, the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (for example, increasing the temperature of the hybridization and/or wash steps, the use of formamide in the hybridization solution, etc.).

"High stringency" conditions are used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

The term "substantially homologous", when used in reference to a double-stranded nucleic acid sequence such as a cDNA or genomic clone, refers to any probe that can hybridize to either or both strands of the double-stranded nucleic acid sequence under conditions of low to high stringency as described above.

The term "substantially homologous", when used in reference to a single-stranded nucleic acid sequence, refers to any probe that can hybridize (in other words, it is the complement of) the single-stranded nucleic acid sequence under conditions of low to high stringency as described above.

The term "hybridization" refers to the pairing of complementary nucleic acids. Hybridization and the strength of hybridization (in other words, the strength of the association between the nucleic acids) is impacted by such factors as the degree of complementary between the nucleic acids, stringency of the conditions involved, the T$_m$ of the formed hybrid, and the G:C ratio within the nucleic acids. A single molecule that contains pairing of complementary nucleic acids within its structure is said to be "self-hybridized."

The term "T$_m$" refers to the "melting temperature" of a nucleic acid. The melting temperature is the temperature at which a population of double-stranded nucleic acid molecules becomes half dissociated into single strands. The equation for calculating the T$_m$ of nucleic acids may be calculated by: T$_m$=81.5.+−.0.41(% G+C), when a nucleic acid is in aqueous solution at 1 M NaCl (See for example, Anderson and Young, Quantitative Filter Hybridization (1985) in Nucleic Acid Hybridization). Other references include more sophisticated computations that take structural as well as sequence characteristics into account for the calculation of T$_m$.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (in other words, replication that is template-dependent but not dependent on a specific template). Template specificity is here distinguished from fidelity of replication (in other words, synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβreplicase, MDV-1 RNA is the specific template for the replicase (Kacian et al. (1972) Proc. Natl. Acad. Sci. USA, 69:3038), i.e. other nucleic acids will not be replicated by this amplification enzyme. Similarly, in the case of T7 RNA polymerase, this amplification enzyme has a stringent specificity for its own promoters (Chamberlin et al. (1970) Nature, 228:227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics, 4:560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (in other words, in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "polymerase chain reaction" ("PCR") refers to the method of Mullis as provided for in U.S. Pat. Nos. 4,683,195, 4,683,202, and 4,965,188, incorporated herein by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (in other words, denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified." With PCR, it is possible to amplify a single copy of a specific target sequence in genomic DNA to a level detectable by several different methodologies (for example, hybridization with a labeled probe; incorporation of biotinylated primers followed by avidin-enzyme conjugate detection; incorporation of .sup.32P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "RACE" refers to "Rapid Amplification of cDNA Ends".

The term "gene expression" refers to the process of converting genetic information encoded in a gene into RNA (for example, mRNA, rRNA, tRNA, or snRNA) through "transcription" of the gene (in other words, via the enzymatic action of an RNA polymerase), and into protein, through "translation" of mRNA. Gene expression can be regulated at many stages in the process. "Up-regulation" or "activation" refers to regulation that increases the production of gene expression products (in other words, RNA or protein), while "down-regulation" or "repression" refers to regulation that decrease production. Molecules (for example, transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc.

The terms "promoter" and "enhancer" as used herein are examples of transcriptional control signals. Promoters and enhancers comprise short arrays of DNA sequences that interact specifically with cellular proteins involved in transcription (Maniatis, et al., Science 236:1237, 1987). Promoter and enhancer elements have been isolated from a variety of eukaryotic sources including genes in yeast, algae insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (in other words precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA. Promoters may be tissue specific or cell specific.

The term "tissue specific" as it applies to a promoter refers to a promoter that is capable of directing selective expression of a nucleotide sequence of interest to a specific type of tissue (for example, seeds) in the relative absence of expression of the same nucleotide sequence of interest in a different type of tissue (for example, leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (for example, detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, for example, immunohistochemical staining. Briefly, tissue sections are embedded in paraffin, and paraffin sections are reacted with a primary antibody that is specific for the polypeptide product encoded by the nucleotide sequence of interest whose expression is controlled by the promoter. A labeled (for example, peroxidase conjugated) secondary antibody that is specific for the primary antibody is allowed to bind to the sectioned tissue and specific binding detected (for example, with avidin/biotin) by microscopy.

The term "constitutive" when made in reference to a promoter means that the promoter is capable of directing transcription of an operably linked nucleic acid sequence in the absence of a stimulus (for example, heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see for example, U.S. Pat. No. 5,352,605, incorporated herein by reference), mannopine synthase, octopine synthase (ocs), superpromoter (see for example, WO 95/14098), and ubi3 (see for example, Garbarino and Belknap (1994) Plant Mol. Biol. 24:119-127) promoters. Such promoters have been used successfully to direct the expression of heterologous nucleic acid sequences in transformed plant tissue.

The term "regulatable" or "induceable", when made in reference to a promoter is one that is capable of directing a level of transcription of an operably linked nuclei acid sequence in the presence of a stimulus (for example, heat shock, chemicals, light, etc.) which is different from the level of transcription of the operably linked nucleic acid sequence in the absence of the stimulus.

An "endogenous" enhancer or promoter is one that is naturally linked with a given gene in the genome.

An "exogenous", "ectopic" or "heterologous" enhancer or promoter is one that is placed in juxtaposition to a gene by means of genetic manipulation (in other words, molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (for example, the first and second genes can be from the same species, or from different species.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al. (1989) Molecular Cloning: A Laboratory Manual, 2nd ed., Cold Spring Harbor Laboratory Press, New York, pp. 16.7-16.8). A commonly used splice donor and acceptor site is the splice junction from the 16S RNA of SV40. Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "selectable marker" refers to a gene which encodes an enzyme having an activity that confers resistance to an antibiotic or drug upon the cell in which the selectable marker is expressed, or which confers expression of a trait which can be detected (for example luminescence or fluorescence). Selectable markers may be "positive" or "negative." Examples of positive selectable markers include the neomycin phosphotransferase (NPTII) gene that confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "vector" as used herein, refers to any nucleic acid molecule that transfers DNA segment(s) from one cell to another. The term "vehicle" is sometimes used interchangeably with "vector."

The terms "expression vector" or "expression cassette" as used herein, refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

The term "transfection", as used herein, refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (in other words, particle bombardment) and the like.

The term "*Agrobacterium*" refers to a soil-borne, Gram-negative, rod-shaped phytopathogenic bacterium that causes crown gall. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (for example, nopaline, agropine, octopine etc.) by the infected cell. Thus, *Agrobacterium* strains which cause production of nopaline (for example, strain LBA4301, C58, A208, GV3101) are referred to as "nopaline-type" *Agrobacteria*; *Agrobacterium* strains which cause production of octopine (for example, strain LBA4404, Ach5, B6) are referred to as "octopine-type" *Agrobacteria*; and *Agrobacterium* strains which cause production of agropine (for example, strain EHA105, EHA101, A281) are referred to as "agropine-type" *Agrobacteria*.

The terms "bombarding, "bombardment," and "biolistic bombardment" refer to the process of accelerating particles towards a target biological sample (for example, cell, tissue, etc.) to effect wounding of the cell membrane of a cell in the target biological sample and/or entry of the particles into the target biological sample. Methods for biolistic bombardment are known in the art (for example, U.S. Pat. No. 5,584,807, the contents of which are incorporated herein by reference), and are commercially available (for example, the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgenic" when used in reference to a plant or fruit or seed (in other words, a "transgenic plant" or "transgenic fruit" or a "transgenic seed") refers to a plant or fruit or seed that contains at least one heterologous gene in one or more of its cells. The term "transgenic plant material" refers broadly to a plant, a plant structure, a plant tissue, a plant seed or a plant cell that contains at least one heterologous gene in one or more of its cells.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "wild-type", "native", or "natural" when made in reference to a gene or protein that has the characteristics of a gene or protein isolated from a naturally occurring source. The term "wild-type" when made in reference to a gene or protein product refers to a gene or protein product that has the characteristics of a gene or protein product isolated from a naturally occurring source. A wild-type gene or protein is that which is most frequently observed in a population and is thus arbitrarily designated the "normal" form. In contrast, the term "modified" or "mutant" when made in reference to a gene, gene product, or protein refers, respectively, to a gene, gene product, or protein which displays modifications in sequence and/or functional properties (in other words, altered characteristics) when compared to the wild-type gene or gene product. It is noted that naturally occurring mutants can be isolated; these are identified by the fact that they have altered characteristics when compared to the wild-type gene, gene product or protein.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex that is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, in other words, at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of an siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "posttranscriptional gene silencing" or "PTGS" refers to silencing of gene expression in plants after transcription, and appears to involve the specific degradation of mRNAs synthesized from gene repeats.

The term "overexpression" refers to the production of a gene product in transgenic organisms that exceeds levels of production in normal or non-transformed organisms.

The term "cosuppression" refers to the expression of a foreign gene that has substantial homology to an endogenous gene resulting in the suppression of expression of both the foreign and the endogenous gene.

The term "altered levels" refers to the production of gene product(s) in transgenic organisms in amounts or proportions that differ from that of normal or non-transformed organisms.

The term "recombinant" when made in reference to a nucleic acid molecule refers to a nucleic acid molecule that is comprised of segments of nucleic acid joined together by means of molecular biological techniques.

The term "recombinant" when made in reference to a protein or a polypeptide refers to a protein molecule that is expressed using a recombinant nucleic acid molecule.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) Molecular Cloning: A Laboratory Manual, Cold Spring Harbor Press, NY, pp 9.31-9.58).

The term "Northern blot analysis" and "Northern blot" and "Northern" as used herein refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook et al. (1989) Molecular Cloning: A Laboratory Manual, Cold Spring Harbor Press, NY, pp 7.39-7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (for example, a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a plant DAGAT includes, by way of example, such nucleic acid in cells ordinarily expressing a DAGAT, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (in other words, the oligonucleotide may single-stranded), but may contain both the sense and anti-sense strands (in other words, the oligonucleotide may be double-stranded).

The term "purified" refers to molecules, either nucleic or amino acid sequences that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. The term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

BRIEF DESCRIPTION OF THE FIGURES

FIGS. 1A and 1B depict one embodiment of a nucleic acid genomic sequence (SEQ ID NO:1), termed DGTT1: Assigned name: GENESH2_PG.C_SCAFFOLD_ 80000044; Protein ID: 180240; Location: Chlre31scaffold_ 80:231821-234837.

FIG. 2 depicts one embodiment of a nucleic acid sequence (SEQ ID NO:2) within SEQ ID NO:1.

FIG. 3 depicts one embodiment of a protein (SEQ ID NO:3) encoded by SEQ ID NO:2.

FIGS. 4A, 4B and 4C depict one embodiment of a nucleic acid genomic sequence (SEQ ID NO:4), termed DGTT2: Assigned name: ESTEXT_FGENESH2_KG.C_240043; Protein ID: 184281; Location: Chlre3/scaffold 24:1045601-1050433.

FIG. 5 depicts one embodiment of a nucleic acid sequence (SEQ ID NO:5) within SEQ ID NO:4.

FIG. 6 depicts one embodiment of a protein (SEQ ID NO:6) encoded by SEQ ID NO:5.

FIGS. 7A and 7B depict one embodiment of a nucleic acid genomic sequence (SEQ ID NO:7), termed DGTT3: Assigned name: ESTEXT_FGENESH2_PG.C_120236: Protein ID: 1889379; Location: Chlre3/scaffold 12:1688101-1691558.

FIG. 8 depicts one embodiment of a nucleic acid sequence (SEQ ID NO:8) within SEQ ID NO:7.

FIG. 9 depicts one embodiment of a protein (SEQ ID NO:9) encoded by SEQ ID NO:8.

FIGS. 10A and 10B depict one embodiment of a nucleic acid genomic sequence (SEQ ID NO: 10), termed DGTT4: Assigned name: CGLD24 (annotated); Protein ID: 190539; Location: 15 Chlre3Vscaffold 19:11746414178245.

FIG. 11 depicts one embodiment of a nucleic acid sequence (SEQ ID NO:11) within SEQ ID NO:10.

FIG. 12 depicts one embodiment of a protein (SEQ ID NO:12) encoded by SEQ ID NO:11.

FIGS. 13A and 13 B one embodiment of a nucleic acid genomic sequence (SEQ ID NO:1.3), termed DGTT5: Assigned name: CHLRE2_KG.SCAFFOLD_7000128; Protein ID: 141301; Location: Chlre3/scaffold 7:877811-880673.

FIG. 14 depicts one embodiment of a nucleic acid sequence (SEQ ID NO:14) within SEQ ID NO:13.

FIG. 15 depicts one embodiment of a protein (SEQ ID NO:15) encoded by SEQ ID NO:14.

DETAILED DESCRIPTION OF THE INVENTION

Figure 16:
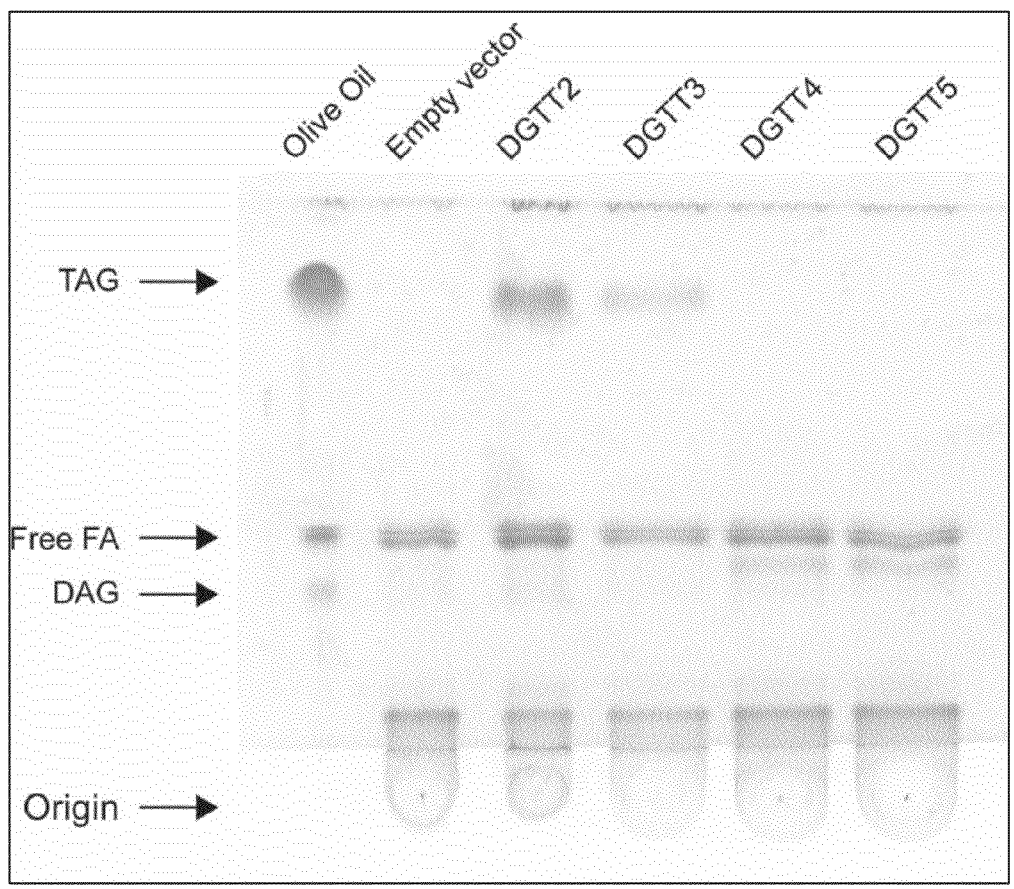
FIG. 16 shows TLC results demonstrating TAG synthesis in yeast transformed with a vector comprising DGTT genes. Yeast transformed with the pYES-DGTT2-5 constructs were grown for two days and 10 mL samples collected. The lipids were extracted with 2:1 methanol:chloroform and loaded on a TLC plate, along with olive oil as a TAG standard. The plate was run with 80:20:1 petroleum ether:diethyl ether: acetic acid as the solvent. The plate was developed with iodine.

The present invention is related to biosynthetic oil compositions and methods of making thereof. In some embodiments, the invention relates to the use of endogenous enzymes in plants capable of synthesizing oil. In preferred embodiments, said plants are algae. In further embodiments, said algae are from the family *Chlamydomonas, Nannochloropsis, Dunaliella, Chlorella* and *Scenedesmus*. In still further embodiments, said endogenous enzymes are diacylglycerol acyltransferases.

In a preferred embodiment, the invention relates to the production of oil by an algae. While not limiting the scope of the present invention, it is believed that oil production in algae occurs under stress conditions, e.g. nutrient stress. Diacylglycerol acyltransferases (DGATs) are a class of enzymes responsible for catalyzing the formation of triglycerides from diacylglycerides and acyl-CoA and may be essential to the formation of adipose tissue in some mammals. The present invention contemplates, in one embodiment, five nucleic acid sequences and their corresponding amino acid sequences in the *Chlamydomonas, Nannochloropsis, Dunaliella, Chlorella* and *Scenedesmus* genomes that are induced under non-stress conditions so that oil production is increased. In preferred embodiments, the invention relates to the expression of DGATs such that algae can produce oil in either the presence of naturally inducing conditions or under conditions introduced artificially. In further embodiments, the DGAT genes are derived from algae selected from the group consisting of *Chlamydomonas, Nannochloropsis, Dunaliella, Chlorella* and *Scenedesmus*.

The presently contemplated invention addresses a widely recognized need for the development of biomass-based domestic production systems for high-energy liquid transportation fuels. In one embodiment, the present invention contemplates inducing oil (i.e., for example, triacylglycerol) biosynthesis in microalgae. This novel inventive concept provides new insights that lay the foundation for rational engineering of algae-based production systems for high-energy fuels. Initial efforts are focused on the unicellular model green alga *Chlamydomonas* reinhardtii with its abundance of genetic and genomic resources.

I. Oil Biosynthesis from Plant Material

Many genes encoding enzymes of storage oil biosynthesis have been isolated from plants. In particular, acyltransferases, ketoacyl-acyl carrier protein synthetases desaturases and related enzymes have been reported. Genetic engineering of these enzymes has been attempted using a single or multiple insertion of a transgene into oil crops, but a method for reliably producing a desired phenotype has not been accomplished. Present research is identifying the complexities of oil storage and membrane lipid formation, including, but not limited to, acyl group remodeling and/or the turnover of unusual fatty acids. Understanding these processes may provide a basis for the rational engineering of transgenic oil crops. In parallel with this, the domestication of plants already synthesising useful fatty acids should be considered as a real alternative to the transgenic approach to producing novel oil crops as disclosed in Murphy D. J., "Production of novel oils in plants" *Curr Opin Biotechnol*. 10:175-180 (1999).

Engineering oilseed crops to produce oils has been a long-standing goal of academic researchers and the biotechnology industry. Many of these oils hold great promise for use in human and animal nutritional regimes, and several others may serve as renewable chemical feedstocks that could replace petroleum-based products in industrial applications. (reviewed in Jaworski et al., "Industrial oils from transgenic plants" *Curr. Opin. Plant Biol*. 6:178-184 (2003); Dyer et al., "Development and potential of genetically engineered oilseeds" *Seed Sci. Res*. 15:255-267 (2005); and Singh et al., "Metabolic engineering of new fatty acids in plants" *Curr. Opin. Plant Biol*. 8:197-203 (2005). For instance, the seed oils of many exotic plant species contain high amounts of unusual fatty acids (e.g., epoxy, hydroxy, conjugated, or acetylenic) that can serve as raw materials for the production of inks, dyes, coatings, and a variety of other bio-based products. Large-scale production of these oils through traditional farming is often impossible because of the poor agronomic traits of these plant species. Furthermore, efforts to transfer genes encoding the proteins responsible for unusual fatty acid biosynthesis to higher yielding plants have generally met with limited success, with much lower amounts of the desired fatty acid accumulating in the oils of transgenic plants (15 to 30%) compared with the native plant species (up to 90%). Thelen et al., "Metabolic engineering of fatty acid biosynthesis in plants" *Metab. Eng*. 4:12-21 (2002).

It is believed that there are at least three major biosynthetic events involved in the production of seed storage oils. The first may involve the synthesis of fatty acids in plastids. The second may involve a modification of these fatty acids by enzymes located primarily in the endoplasmic reticulum (ER). The third may involve packaging of nascent fatty acids into triacylglycerols (TAGs), which subsequently accumulate in oil bodies that bud off from the ER. Research information is currently available regarding the synthesis and modification of fatty acid-containing oil body structures. (Ohlrogge et al., "Lipid Biosynthesis: *Plant Cell* 7:957-970. (1995); and Shanklin et al., "Desaturation and related modifications of fatty acids" *Annu. Rev. Plant Physiol. Plant Mol. Biol.* 49:611-641 (1998).

Biochemical analyses have shown that TAG is synthesized in the ER by at least two pathways. The first involves the acyl-CoA-independent transfer of fatty acids from phospholipids to the sn-3 position of diacylglycerol to form TAG. This reaction is catalyzed by phospholipid:diacylglycerolacyltransferase (PDAT). Dahlqvist et al., "Phospholipid: diacylglycerol acyltransferase: An enzyme that catalyzes the acyl-CoA-independent formation of triacylglycerol in yeast and plants" *Proc. Natl. Acad. Sci. USA* 97:6487-6492 (2000); and Stahl et al., "Cloning and functional characterization of a phospholipid:diacylglycerol acyltransferase from *Arabidopsis*" *Plant Physiol* 135:1324-1335 (2004). TAG is also produced via three successive acylation reactions of the hydroxyl groups of glycerol, starting from glycerol-3-phosphate, with diacylglycerol acyltransferase (DGAT) catalyzing the committed step: the transfer of a fatty acyl moiety from acyl-CoA to the sn-3 position of diacylglycerol. (Kennedy, "Biosynthesis of complex lipids" *Fed. Proc.* 20:934-940 (1961). As such, it is believed that DGAT plays a role in controlling: i) the quantitative flux of fatty acids into storage TAGs (Ichihara et al., "Diacylglycerol acyltransferase in maturing safflower seeds: Its influences on the fatty acid composition of triacylglycerol and on the rate of triacylglycerol synthesis" *Biochim. Biophys. Acta* 958:125-129 (1988); and ii) the qualitative flux of fatty acids into storageTAGs. (Vogel et al., Cholinephosphotransferase and diacylglycerol acyltransferase (substrate specificities at a key branchpoint in seed lipid metabolism)" *Plant Physiol* 110:923-931 (1996); and He et al., "Regulation of diacylglycerol acyltransferase in developing seeds of castor" *Lipids* 39:865-871. (2004).

It has been reported that a developing plant seed generates an oil storage reserve in the form of triacylglycerols. Baud et al., "An integrated overview of seed development in *Arabidopsis thaliana* ecotype WS" *Plant Physiol. Biochem* 40:151-160 (2002). The impact that glycolytic metabolic pathways have on this oil storage process has been previously studied. Glycolysis is a ubiquitous pathway thought to be essential for the production of oil in developing seeds of *Arabidopsis thaliana* and oil crops. Compartmentation of primary metabolism in developing embryos poses a significant challenge for testing this hypothesis and for the engineering of seed biomass production. It also raises the question whether there is a preferred route of carbon from imported photosynthate to seed oil in the embryo. Plastidic pyruvate kinase catalyzes a highly regulated, ATP-producing reaction of glycolysis. The *Arabidopsis* genome encodes putative isoforms of pyruvate kinases. Three genes encode subunits α, β1, and β2 of plastidic pyruvate kinase. The plastid enzyme prevalent in developing seeds likely has a subunit composition of 4α4β1, is most active at pH 8.0, and is inhibited by glucose. Disruption of the gene encoding the β1 subunit causes a reduction in plastidic pyruvate kinase activity and 60% reduction in seed oil content. The seed oil phenotype is fully restored by expression of the β1 subunit-encoding cDNA and partially by the β2 subunit-encoding cDNA. Therefore, the identified pyruvate kinase catalyzes a crucial step in the conversion of photosynthate into oil, suggesting a preferred plastid route from its substrate phosphoenolpyruvate to fatty acids. Andre et al., "A Heteromeric Plastidic Pyruvate Kinase Complex Involved In Seed Oil Biosynthesis in *Arabidopsis*" The Plant Cell 19:2006-2022 (2007).

II. Biosynthetic Oil Producing Genes

Oil biosynthesis in algae has been reported to occur under stress conditions (i.e., for example, nutrient stress). The present invention contemplates engineering oil biosynthesis and increased oil yield in algae. The present invention also contemplates novel genes for the engineering of oil content in microalgae.

It is generally believed that many algae species including, but not limited to, *Chlamydomonas reinhardtii* accumulate biosynthetic oils (i.e., for example, triacylglycerols) when cultures enter a stationary cell cycle phase subsequent to nutrient limitation. In one embodiment, the present invention contemplates methods for identifying microalgal genes encoding biosynthetic oil regulatory enzymes and/or biosynthetic oil regulatory factors.

A. Biosynthetic Oil Producing Enzymes

In one embodiment, the present invention contemplates biosyntheic oil genes encoding diacylglycerol acyltransferases (DGATs). In one embodiment, the expression of DGAT results in the production of a biosynthetic oil. In one embodiment, the biosynthetic oil comprises a triacylglycerol.

DGAT enzyme activity is believed to be encoded by at least two classes of genes in eukaryotic cells. The type 1 class of DGAT enzymes (DGAT1) was discovered first in mouse based on homology with mammalian acyl-CoA:cholesterol acyltransferase genes. Cases et al., "Diacylglycerol acyltransferase in maturing oil seeds of maize and other species" *Plant Physiol.* 82:813-820 (1998). Subsequently, other DGAT1 genes were identified and characterized in several plant species. Hobbs et al., "Cloning of a cDNA encoding diacylglycerol acyltransferase from *Arabidopsis thaliana* and its functional expression" *FEBS Lett.* 452:145-149 (1999); Zou et al., "The *Arabidopsis thaliana* TAG1 mutant has a mutation in a diacylglycerol acyltransferase gene" *Plant J.* 19:645-653.1999; Bouvier-Navé et al., "Expression in yeast and tobacco of plant cDNAs encoding acyl CoA:diacylglycerol acyltransferase" *Eur. J. Biochem* 267:85-96 (2000); Nykiforuk et al., "Characterization of cDNAs encoding diacylglycerol acyltransferase from cultures of *Brassica napus* and sucrose-mediated induction of enzyme biosynthesis" *Biochim. Biophys. Acta* 1580:95-109 (2002); He et al., "Cloning and characterization of a cDNA encoding diacylglycerol acyltransferase from castor bean" *Lipids* 39:311-318 (2004); Milcamps et al., "Isolation of a gene encoding a 1,2-diacylglycerol-sn-acetyl-CoA acetyltransferase from developing seeds of *Euonymus alatus*" *J. Biol. Chem.* 280:5370-5377 (2005).

In *Arabidopsis thaliana*, the DGAT1 gene has been shown to contribute significantly to TAG biosynthesis. In one study, TAG biosynthesis was induced by DGAT1 overexpression. Jako et al., "Seed-specific over-expression of an *Arabidopsis* cDNA encoding a diacylglycerol acyltransferase enhances seed oil content and seed weight" *Plant Physiol.* 126:861-874 (2001). In another study, TAG biosynthesis was studied using mutational downregulation studies. Katavic et al., "Alteration of seed fatty acid composition by an ethyl methanesulfonate-induced mutation in *Arabidopsis thaliana* affecting diacylglycerol acyltransferase activity" *Plant Physiol.* 108:399-409 (1995); and Routaboul et al., "The TAG1 locus of *Arabidopsis* encodes for a diacylglycerol acyltransferase" *Plant Physiol. Biochem.* 37:831-840 (1999).

The type 2 class of DGAT enzymes (DGAT2) also has been identified in a number of eukaryotes, including fungi, *Caenorhabditis elegans*, humans, and *Arabidopsis*. Cases et al., "Diacylglycerol acyltransferase in maturing oil seeds of maize and other species" *Plant Physiol.* 82:813-820 (1998); and Lardizabal et al., "DGAT2 is a new diacylglycerol acyltransferase gene family: purification, cloning, and expression in insect cells of two polypeptides from *Mortierella ramanniana* with diacylglycerol acyltransferase activity" 1 *J. Biol. Chem.* 276:38862-38869 (2001). The physiological function(s) of these DGAT2 enzymes in plants, however, has not been determined. Characterizing the subcellular properties of these enzymes would provide new insight into the underlying mechanisms of oil biosynthesis. This knowledge may be especially important for the production of seed oils containing unusual fatty acids, because these structures are generally incompatible with normal membrane lipids and the spatial separation of lipid biosynthetic enzymes in the ER may provide an efficient mechanism for channeling these unusual fatty acids into storage oils.

In particular, one study has reported a detailed analysis of DGAT1 and DGAT2 in tung tree seeds. Seeds of the tung tree (*Vernicia fordii*) produce large quantities of triacylglycerols (TAGs) containing 80% eleostearic acid, an unusual conjugated fatty acid. We presented a comparative analysis of the genetic, functional, and cellular properties of tung type 1 and type 2 diacylglycerol acyltransferases (DGAT1 and DGAT2), two unrelated enzymes that catalyze the committed step in TAG biosynthesis. We showed that both enzymes are encoded by single genes and that DGAT1 is expressed at similar levels in various organs, whereas DGAT2 is strongly induced in developing seeds at the onset of oil biosynthesis. Expression of DGAT1 and DGAT2 in yeast produced different types and proportions of TAGs containing eleostearic acid, with DGAT2 possessing an enhanced propensity for the synthesis of trieleostearin, the main component of tung oil. Both DGAT1 and DGAT2 are located in distinct, dynamic regions of the endoplasmic reticulum (ER), and surprisingly, these regions do not overlap. Furthermore, although both DGAT1 and DGAT2 contain a similar C-terminal pentapeptide ER retrieval motif, this motif alone is not sufficient for their localization to specific regions of the ER. These data suggest that DGAT1 and DGAT2 have non-redundant functions in plants and that the production of storage oils, including those containing unusual fatty acids, occurs in distinct ER subdomains. Shockey et al., "Tung Tree DGAT1 and DGAT2 Have Nonredundant Functions in Triacylglycerol Biosynthesis and Are Localized to Different Subdomains of the Endoplasmic Reticulum" *The Plant Cell* 18:2294-2313 (2006).

B. Microalgal Diacylglycerol Acetyltransferase

In one embodiment, the present invention contemplates the biochemical characterization and use of microalgal DGATs and their role in oil biosynthesis. The newly identified genes and the functional genomic information will provide novel materials for engineering approaches towards inducing and optimizing microalgal oil production. In further embodiments, the genes are cloned from cDNA into pYES, a yeast shuttle vector capable of functioning in both yeast and bacteria. In still further embodiments, DGATs are cloned with N-terminal and C-terminal His tags.

III. Host Organisms

Host organisms that are transformed with a heterologous gene encoding a DGAT of the present invention include, but are not limited to, those organisms that naturally express triacylglycerols (TAGs) and those organisms in which it is commercially feasible to grow for harvesting in large amounts of the TAG products. Such organisms include but are not limited to, oleaginous yeast and algae, and plants and animals. Examples of yeasts include oleaginous yeast, which include but are not limited to the genera *Lipomyces, Candida, Rhodotorula, Rhodosporidium* and *Cryptococcus*, which can be grown in commercial-scale fermenters. Examples of algae include, but are not limited to, *Chlamydomonas, Nannochloropsis, Dunaliella, Chlorella* and *Scenedesmus*. Examples of plants include preferably oil-producing plants, such as soybean, rutabaga, rapeseed and canola, sunflower, cotton, corn, cocoa, safflower, oil palm, coconut palm, flax, castor, and peanut. Many commercial cultivars can be transformed with heterologous genes.

A heterologous gene encoding an DGAT of the present invention, including variants or mutations of DGAT, includes any suitable sequence of the invention as described above. Preferably, the heterologous gene is provided within an expression vector such that transformation with the vector results in expression of the polypeptide. Suitable vectors are described herein.

A transgenic organism (i.e., for example, a transgenic *C. reinhardtii*) is grown under conditions sufficient to effect production of TAGs. In some embodiments of the present invention, a transgenic organism is supplied with exogenous substrates of DGAT (as, for example, in a fermenter). Such substrates can comprise sugars as carbon sources for TAG synthesis, fatty acids and glycerol used directly for the production of DAG and TAG, DAG itself, and acetic acid which will both provide a general carbon source and be used for the production of acetyl-CoA and/or diacylglycerols (DAGs). When related groups are transferred to DAG, such substrates may instead or in addition be provided to the transgenic organism; exemplary related group include but are not limited to butyrate, propionate, and cinnamate. Substrates may be supplied in various forms including, but not limited to, aqueous suspensions prepared by sonication, aqueous suspensions prepared with detergents and other surfactants, dissolution of the substrate into a solvent, and dried powders of substrates. Such forms may be added to organisms or cultured cells or tissues grown in fermenters.

In yet other embodiments of the present invention, a transgenic organism (i.e., for example, a transgenic *C. reinhardtii*) comprises a gene encoding a DGAT of the present invention operably linked to an inducible promoter, and is grown either in either the presence or absence of the an inducing agent and/or inducing environmental condition (i.e., for example, nutrient stress), or is grown and then exposed to an inducing agent. In still other embodiments of the present invention, a transgenic organism comprises a gene encoding a DGAT of the present invention is operably linked to a promoter which is either species, cell, and/or tissue specific or developmentally specific, and is grown to the point at which the organism is developed or the developmental stage at which the developmentally-specific promoter is activated. Such promoters include, but are not limited to, seed specific promoters.

In alternative embodiments, a transgenic organism as described above is engineered to produce greater amounts of the diacylglycerol substrate. Thus, it is contemplated that a transgenic organism may include further modifications such that fatty acid synthesis is increased, and may in addition or instead include exogenous acyltransferases and/or phosphatidic acid phospatases.

In other embodiments of the present invention, a host organism produces large amounts of a desired substrate, such as acetyl-CoA or DAG; non-limiting examples include organisms transformed with genes encoding acetyl-CoA synthetases and/or ATP citrate lyase. In some embodiments, it is contemplated that certain DAGs will result in the synthesis of novel TAGs with desirable properties. Thus, a particularly suitable host is one that produces a high proportion of such a DAG.

In other embodiments, a host organism produces low amounts of a desired substrate such as DAG. It is contemplated that in such hosts, novel TAGs produced from an exogenous DGAT are a higher proportion of the total TAGs; advantages include less expensive purification of the novel TAGs. Non-limiting exemplary hosts include those with low flux through lipid synthetic systems or with low endogenous DGAT activity (either or both DGAT1 or DGAT2). Such hosts may occur naturally or via genetic engineering techniques. Non-limiting exemplary techniques include knockout produced by EMS and transposon tagging.

In other embodiments of the present invention, the methods for producing TAGs further comprise collecting the TAGs produced. Several methods have been reported, and include harvesting the transgenic organisms and extracting the TAGs (see, for example, Christie, W. W. (1982) Lipid Analysis. $2^{nd}$ Edition (Pergamon Press, Oxford); and Kates, M (1986) Techniques of Lipidology (Elsevier, Amsterdam)). Extraction procedures preferably include solvent extraction, and typically include disrupting cells, as by chopping, mincing, grinding, and/or sonicating, prior to solvent extraction. In one embodiment, lipids are extracted from the tissue according to the method of Bligh and Dyer (1959) (Can J Biochem Physiol 37: 911-917). In yet other embodiments of the present invention, the TAGs are further purified, as for example by thin layer liquid chromatography, gas-liquid chromatography, counter current chromatography or high performance liquid chromatography.

A. Vectors

The methods of the present invention contemplate the use of at least a heterologous gene encoding an DGAT gene of the present invention operably linked to a vector comprising a promoter.

Heterologous genes intended for expression in plant cells may first be assembled in expression cassettes comprising a promoter. Many methods may be used to construct expression vectors containing a heterologous gene and appropriate control elements. These methods include, but are not limited to, in vitro recombinant DNA techniques, synthetic techniques, and in vivo genetic recombination. Such techniques are widely described in the art (See for example, Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.).

In general, these vectors comprise a nucleic acid sequence of the invention encoding a DGAT gene of the present invention (as described above) operably linked to a promoter and other constructs (for example, enhancers, polyadenylation signals, etc.) required for expression in a plant cell.

Useful promoters include, but are not limited to, constitutive promoters, tissue-, organ-, and developmental-specific promoters, and inducible promoters. Examples of promoters include, but are not limited to: constitutive promoter 35S of cauliflower mosaic virus; a wound-inducible promoter from tomato, leucine amino peptidase ("LAP," Chao et al. (1999) Plant Physiol 120: 979-992); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (U.S. Pat. No. 5,187,267) (herein incorporated by reference); a tetracycline-inducible promoter (U.S. Pat. No. 5,057,422) (herein incorporated by reference); and seed-specific promoters, such as those for seed storage proteins (for example, phaseolin, napin, oleosin, and a promoter for soybean beta conglycin (Beachy et al. (1985) EMBO J. 4: 3047-3053)). All references cited herein are incorporated by reference in their entirety.

The expression cassettes may further comprise any sequences required for expression of mRNA. Such sequences include, but are not limited to, transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (See for example, Odell et al. (1985) Nature 313:810; Rosenberg et al. (1987) Gene, 56:125; Guerineau et al. (1991) Mol. Gen. Genet., 262:141; Proudfoot (1991) Cell, 64:671; Sanfacon Et al. Genes Dev., 5:141; Mogen et al. (1990) Plant Cell, 2:1261; Munroe et al. (1990) Gene, 91:151; Ballad et al. (1989) Nucleic Acids Res. 17:7891; Joshi et al. (1987) Nucleic Acid Res., 15:9627).

In addition, in some embodiments, constructs for expression of the gene of interest include one or more of sequences found to enhance gene expression from within the disclosed constructs. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Calais et al. (1987) Genes Develop. 1: 1183). Intron sequences have been routinely incorporated into plant transformation vectors, typically within the non-translated leader.

In preparing a construct comprising a nucleic acid sequence encoding the DGAT genes of the present invention, various DNA fragments can be manipulated, so as to provide for the DNA sequences in the desired orientation (for example, sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (for example, transitions and transversions) are involved.

Numerous transformation vectors are available for plant cell transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra (1982) Gene 19: 259; Bevan et al. (1983) Nature 304:184), the bar gene which confers resistance to the herbicide phosphinothricin (White et al. (1990) Nucl Acids Res. 18:1062; Spencer et al. (1990) Theor. Appl. Genet. 79:625), the hph gene which confers resistance to the antibiotic hygromycin (Blochlinger and Diggelmann (1984) Mol. Cell. Biol. 4:2929), and the dhfr gene, which confers resistance to methotrexate (Bourouis et al. (1983) EMBO J., 2:1099).

In some embodiments, the vector is adapted for use in an *Agrobacterium* mediated transfection process (See for example, U.S. Pat. Nos. 5,981,839; 6,051,757; 5,981,840; 5,824,877; and 4,940,838; all of which are incorporated herein by reference). Additional use can be made of accessory genetic elements sometimes found with the native plasmids and sometimes constructed from foreign sequences. These may include but are not limited to structural genes for antibiotic resistance as selection genes.

Exemplary systems of using recombinant plasmid vectors that are compatible with the present invention include, but are not limited to the "conintegrate" and "binary" systems. In the "cointegrate" system, the shuttle vector containing the gene of interest is inserted by genetic recombination into a non-oncogenic plasmid that contains both the cis-acting and trans-acting elements required fr plant cell transformation as, for example, in the pMLJ1 shuttle vector and the non-oncogenic plasmid pGV3850. The second system is called the "binary" system in which two plasmids are used; the gene of interest is inserted into a shuttle vector containing the cis-acting elements required for plant transformation. The other necessary functions are provided in trans by the non-oncogenic plasmid as exemplified by the pBIN19 shuttle vector and the non-oncogenic plasmid PAL4404. These and other vectors useful for these systems are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination. Generally, plant cells are incubated with an organism comprising a targeting vector in which sequences that are homologous to a DNA sequence inside the target locus are flanked by transfer-DNA (T-DNA) sequences. U.S. Pat. No. 5,501,967 (herein incorporated by reference). Homologous recombination may be achieved using targeting vectors that contain sequences that are homologous to any part of the targeted plant gene. Homologous recombination may be achieved at any region of a plant gene so long as the nucleic acid sequence of regions flanking the site to be targeted is known.

In yet other embodiments, the nucleic acids of the present invention are utilized to construct vectors derived from plant (+) RNA viruses (i.e., for example, brome mosaic virus, tobacco mosaic virus, alfalfa mosaic virus, cucumber mosaic virus, tomato mosaic virus, and combinations and hybrids thereof). Generally, the DGAT nucleic acid sequence of the present invention can be expressed from these vectors as a fusion protein (for example, coat protein fusion protein) or from its own sub-genomic promoter or other promoter. Methods for the construction and use of such viruses are described. U.S. Pat. Nos. 5,846,795; 5,500,360; 5,173,410; 5,965,794; 5,977,438; and 5,866,785, all of which are incorporated herein by reference.

In some embodiments of the present invention the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (WO 93/07278).

B. Transformation Techniques

In one embodiment, the present invention contemplates a composition comprising a nucleic acid sequence encoding a DGAT gene of the present invention that is operatively linked to an appropriate promoter and inserted into a suitable vector for a particular transformation technique. Recombinant DNA, such as that described above, can be introduced into a plant cell in a number of ways. The choice of any specific method might depend on the type of plant targeted for transformation. In some embodiments, a vector is maintained episomally (i.e., for example, transient transformation). In other embodiments, a vector is integrated into the genome (i.e., for example, stable transformation).

In some embodiments, direct transformation in the plastid genome is used to introduce the vector into a plant cell. U.S. Pat. Nos. 5,451,513; 5,545,817; 5,545,818; PCT application WO 95/16783 (all references herein incorporated by reference). The basic technique for chloroplast transformation involves introducing regions of cloned plastid DNA flanking a selectable marker together with the nucleic acid encoding the RNA sequences of interest into a suitable target tissue (i.e., for example, using biolistics or protoplast transformation with calcium chloride or polyethylene glycol). The 1 kb to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation. (Svab et al. (1990) PNAS, 87:8526; Staub and Maliga, (1992) Plant Cell, 4:39). The presence of cloning sites between these markers allowed creation of a plastid targeting vector introduction of foreign DNA molecules (Staub and Maliga (1993) EMBO J., 12:601). Substantial increases in transformation frequency may be obtained by replacement of the recessive rRNA or r-protein antibiotic resistance genes with a dominant selectable marker, such as a bacterial aadA gene encoding the spectinomycin-detoxifying enzyme aminoglycoside-3'-adenyltransferase (Svab and Maliga (1993) PNAS, 90:913). Other selectable markers have been shown useful for plastid transformation. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway (1985) Mol. Gen. Genet, 202:179). In still other embodiments, the vector is transferred into the plant cell by using polyethylene glycol (Krens et al. (1982) Nature, 296:72; Crossway et al. (1986) BioTechniques, 4:320); fusion of protoplasts with other entities, either minicells, cells, lysosomes or other fusible lipid-surfaced bodies (Fraley et al. (1982) Proc. Natl. Acad. Sci., USA, 79:1859); protoplast transformation (EP 0 292 435); direct gene transfer (Paszkowski et al. (1984) EMBO J., 3:2717; Hayashimoto et al. (1990) Plant Physiol. 93:857).

In still further embodiments, the vector may also be introduced into the plant cells by electroporation (Fromm, et al. (1985) Proc. Natl. Acad. Sci. USA 82:5824; Riggs et al. (1986) Proc. Natl. Acad. Sci. USA 83:5602). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (for example, available from Agracetus, Inc., Madison, Wis. and Dupont, Inc., Wilmington, Del.). (See for example, U.S. Pat. No. 4,945,050 (herein incorporated by reference); and McCabe et al. (1988) Biotechnology 6:923). See also, Weissinger et al. (1988) Annual Rev. Genet. 22:421; Sanford et al. (1987) Particulate Science and Technology, 5:27 (onion); Svab et al. (1990) Proc. Natl. Acad. Sci. USA, 87:8526 (tobacco chloroplast); Christou et al. (1988) Plant Physiol., 87:671 (soybean); McCabe et al. (1988) Bio/Technology 6:923 (soybean); Klein et al. (1988) Proc. Natl. Acad. Sci. USA, 85:4305 (maize); Klein et al. (1988) Bio/Technology, 6:559 (maize); Klein et al. (1988) Plant Physiol., 91:4404 (maize); Fromm et al. (1990) Bio/Technology, 8:833; and Gordon-Kamm et al. (1990) Plant Cell, 2:603 (maize); Koziel et al. (1993) Biotechnology, 11:194 (maize); Hill et al. (1995) Euphytica, 85:119 and Koziel et al. (1996) Annals of the New York Academy of Sciences 792:164; Shimamoto et al. (1989) Nature 338: 274 (rice); Christou et al. (1991) Biotechnology, 9:957 (rice); Datta et al. (1990) Bio/Technology 8:736 (rice); European Patent Application EP 0 332 581 (orchardgrass and other Pooideae); Vasil et al. (1993) Biotechnology, 11: 1553 (wheat); Weeks et al. (1993) Plant Physiol., 102: 1077 (wheat); Wan et al. (1994) Plant Physiol. 104: 37 (barley); Jahne et al. (1994) Theor. Appl. Genet. 89:525 (barley); Knudsen and Muller (1991) Planta, 185:330 (barley); Umbeck et al. (1987) Bio/Technology 5: 263 (cotton); Casas et al. (1993) Proc. Natl. Acad. Sci. USA 90:11212 (sorghum); Somers et al. (1992) Bio/Technology 10:1589 (oat); Torbert et al. (1995) Plant Cell Reports, 14:635 (oat); Weeks et al. (1993) Plant Physiol., 102:1077 (wheat); Chang et al., WO 94/13822 (wheat) and Nehra et al. (1994) The Plant Journal, 5:285 (wheat).

In addition to direct transformation, in some embodiments, the vectors comprising a nucleic acid sequence encoding a DGAT gene of the present invention are transferred using *Agrobacterium*-mediated transformation (Hinchee et al. (1988) Biotechnology, 6:915; Ishida et al. (1996) Nature Biotechnology 14:745). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (i.e., for example, nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell (1987) Science, 237: 1176). Species that are susceptible infection by *Agrobacterium* may be transformed in vitro. Alternatively, plants may be transformed in vivo, such as by transformation of a whole plant by *Agrobacteria* infiltration of adult plants, as in a "floral dip" method (Bechtold N, Ellis J, Pelletier G (1993) Cr. Acad. Sci. III-Vie 316: 1194-1199).

C. Differential Expression of Biosynthetic Oil Producing Genes

The data presented herein identify a set of differentially expressed genes for microalgal triacylglycerol biosynthesis. In one embodiment, the differentially expressed genes are identified under induced conditions. In one embodiment, the differentially expressed genes are identified under non-induced conditions. Global expression analysis is but one method that is capable of determining possible sets of the differentially expressed genes in question. Other methods, of course, are also useful.

The degree of differentiation or physiological state of a cell, a tissue or an organism is characterized by a specific expression status. Characterization of this expression status is indicative to answering many biological questions. Changes in gene expression in response to a stimulus, a developmental stage, a pathological state or a physiological state are important in determining the nature and mechanism of the change and in finding cures that could reverse a pathological condition. Patterns of gene expression are also expected to be useful in the diagnosis of pathological conditions, and for example, may provide a basis for the sub-classification of functionally different subtypes of cancerous conditions.

1. Traditional Differential Expression Analysis Techniques

Several methods that can analyze the expression status of genes are presently used. For example, differential display RT-PCR (DDRT) is one method for analyzing differential gene expression in which subpopulations of complementary DNA (cDNA) are generated by reverse transcription of mRNA by using a cDNA primer with a 3' extension (i.e., for example, by using two bases). Random 10-base primers are then used to generate PCR products of transcript-specific lengths. If the number of primer combinations used is large enough, it is statistically possible to detect almost all transcripts present in any given sample. PCR products obtained from two or more samples are then electrophoresed next to one another on a gel and differences in expression are directly compared. Differentially expressed bands can be cut out of the gel, reamplified and cloned for further analysis.

In one embodiment of DDRT it is possible to enrich the PCR amplification products for a particular subgroup of all mRNA molecules, e.g., members of a particular gene family by using one primer which has a sequence specific for a gene family in combination with one of the 10 base random primers. Liang et al., *Science*, 257:967-971 (1992); Liang et al., *Nucleic Acids Res* 21:3269-3275 (1993); Bauer et al., *Nucleic Acids Res.*, 21:4272-4280 (1993); Stone et al., *Nucleic Acids Res.*, 22:2612-2618 (1994); Wang et al., *Biotechniques* 18:448-453 (1995); WO 93/18176; and DE 43 17 414 (all references herein incorporated by reference in their entirety).

There are a number of disadvantages to the experimental design of DDRT. The differential banding patterns are often only poorly reproducible. Due to the design of the primers even the use of longer random primers of, e.g., 20 bases in length does not satisfactorily solve the problem of reproducibility. Ito et al., *FEBS Lett* 351:231-236 (1994). In order to evaluate a significant portion of differentially expressed genes, a large number of primer combinations must be used and multiple replicates of each study must be done. The method often results in a high proportion of false positive results and rare transcripts cannot be detected in many DDRT studies. Bertioli et al., *Nucleic Acids Res.* 23:4520-4523 (1995.)

Due to the non-stringent PCR conditions and the use of only one arbitrary primer further analysis by sequencing is necessary to identify the gene. Sequencing of selected bands is problematic since the same primer often flanks DDRT products at both ends so that direct sequencing is not possible and an additional cloning step is necessary. Due to the use of short primers, a further reamplification step with primer molecules extended on the 5' side is necessary even if two different primers flank the product. Finally, due to the use of random primers, it is never quite possible to be sure that the primer combinations recognize all transcripts of a cell. This applies, even when using a high number of primers, to studies that are intended to detect the entirety of all transcripts as well as to studies that are directed towards the analysis of a sub-population of transcripts such as a gene family.

A variant of DDRT, known as GeneCalling, has recently been described which addresses some of these problems. Shimkets et al., *Nat. Biotechnol.* 17:798-803 (1999). In this method, multiple pairs of restriction endonucleases are used to prepare specific fragments of a cDNA population prior to amplification with pairs of universal primers. This improves the reproducibility of the measurements and the false positive rate, but the patterns are very complex and identification of individual transcripts requires the synthesis of a unique oligonucleotide for each gene to be tested. In addition, the quantitative data obtained are apparently significant only for changes above 4-fold and only a weak correlation with other techniques is obtained. The ability of the technique to distinguish the gene-specific band from the complex background for any arbitrarily chosen gene has not been documented.

AFLP based mRNA fingerprinting further addresses some of the deficiencies of DDRT. AFLP allows for the systematic comparison of the differential expression of genes between RNA samples. Habu et al, *Biochem Biophys Res Commun* 234:516-21 (1997) The technique involves the endonuclease digestion of immobilized cDNA by a single restriction enzyme. The digested fragments are then ligated with a linker specific for the restriction cut site. The tailed fragments are subsequently amplified by PCR employing primers complementary to the linkers added to the digest with the addition of variable nucleotides at the 3' end of the primers. The products of the amplification are visualized by PAGE and banding patterns compared to reveal differences in RNA transcription patterns between samples. Although AFLP based RNA fingerprinting provides a indication of the RNA message present in a given sample, it fails to restrict the potential number of signals produced by each individual RNA strand. With this technique, each RNA strand may potentially produce multiple fragments and therefore multiple signals upon amplification. This failure to restrict the number of signals from each message complicates the results that must be evaluated.

Methods have been described for examining the expression of homologous genes in plant polyploids in which the techniques of RT-PCR. and restriction fragment length polymorphism (RFLP) analysis are combined with one another. Song et al., *Plant Mol. Biol.* 26:1065-1071 (1994). This method uses a cDNA produced from RNA by reverse transcription, and then amplified by using two gene-specific primers. The amplification products are transcript-specifically shortened by endonuclease cleavage, separated by electrophoresis according to their length, cloned, and then analyzed by sequencing. This method has the disadvantage of low sensitivity, as a cloning step is necessary to characterize the expression products. A further disadvantage of this method is that gene specific sequence information must be available on at least two regions within the analyzed genes in order to design suitable primers.

In principle, gene expression data for a particular biological sample could be obtained by large-scale sequencing of a cDNA library. The role of sequencing cDNA, generated by reverse transcription from mRNA, has been debated for its value in the human genome project. Proponents of genomic sequencing have argued the difficulty of finding every mRNA expressed in all tissues, cell types, and developmental stages. In addition, libraries of cDNA may to be dominated by repetitive elements, mitochondrial genes, ribosomal RNA genes, and other nuclear genes comprising common or housekeeping sequences. While some mRNAs are abundant, others are rare, resulting in cellular quantities of mRNA from various genes that can vary by several orders of magnitude. Therefore, sequencing of transcribed regions of the genome using cDNA libraries has been considered unsatisfactory.

Techniques based on cDNA subtraction or differential display can be used to compare gene expression patterns between two cell types. Hedrick et al., *Nature* 308:153-8 (1984); and Liang et al., *Science* 257:967-971 (1992). These techniques, however, provide only a partial analysis, with no quantitative information regarding the abundance of messenger RNA. Expressed sequence tags (EST) have been valuable for gene discovery. (Adams et al., *Nat Genet,* 4:373-4380 (1993); and Okubo et al., *Nat. Genet.* 2:173-179 (1992), but like Northern blotting, RNase protection, and reverse transcriptase-polymerase chain reaction (RT-PCR) analysis, this approach only evaluates a limited number of genes at a time.

2. Global Gene Expression

Several strategies for global gene expression analysis have recently become available. For example, Serial Analysis of Gene Expression (SAGE) is based on the use of short (i.e., for example, 9-10 base pairs) nucleotide sequence tags that identify a defined position in an mRNA and are used to ascertain the identity of the corresponding transcript and gene. U.S. Pat. No. 5,866,330 To Kinzler et al., (1995) (herein incorporated by reference). The cDNA tags are generated from mRNA samples, randomly paired, concatenated, cloned, and sequenced. While this method allows the analysis of a large number of transcripts, the identification of individual genes requires sequencing of tens of thousands of tags for comparison of even a small number of samples. Although SAGE provides a comprehensive picture of gene expression, it is difficult to specifically direct the analysis at a small subset of the transcriptome. (Zhang et al., *Science* 276:1268-1272 (1997); and Velculescu et al., *Cell* 88:243-251 (1995). Data on the most abundant transcripts is the easiest and fastest to obtain, while about a megabase of sequencing data is needed for confident analysis of low abundance transcripts.

Another global expression analysis method utilizes hybridization of cDNAs or mRNAs to microarrays containing hundreds or thousands of individual cDNA fragments or oligonucleotides specific for particular genes or ESTs. The matrix for hybridization is either a DNA chip, a slide or a membrane. This method can be used to direct a search towards specific subsets of genes, but cannot be used to identify novel genes as are expensive to produce. DeRisi et al., *Nature Genetics,* 14:457-460 (1996); and Schena et al., *Science* 270:467-470 (1995). For those methods using cDNA arrays, a library of individually cloned DNA fragments must be maintained with at least one clone for each gene to be analyzed. Because much of the expense of utilizing microarrays lies in maintaining the fragment libraries and programming equipment to construct the microarray, it is only cost-efficient to produce large numbers of identical arrays. These two techniques lack the flexibility to easily change the subset of the transcriptome being analyzed or to focus on smaller subsets of genes for more detailed analyses.

As described above, current techniques for analysis of gene expression either monitor one gene at a time, are designed for the simultaneous and therefore more laborious analysis of thousands of genes or do not adequately restrict the signal to message ratio. There is a need for improved methods which encompass both rapid, detailed analysis of global expression patterns of genes as well as expression patterns of defined sets of genes for the investigation of a variety of biological applications. This is particularly true for establishing changes in the pattern of gene expression in the same cell type, for example, in different developmental stages, under different physiologic or pathologic conditions, when treated with different pharmaceuticals, mutagens, carcinogens, etc. Identification of differential patterns of expression has several utilities, including the identification of appropriate therapeutic targets, candidate genes for gene therapy (including gene replacement), tissue typing, forensic identification, mapping locations of disease-associated genes, and for the identification of diagnostic and prognostic indicator genes.

D. High-Throughput cDNA Pyrosequencing

A high-throughput cDNA pyrosequencing experiment will be conducted under induced and non-induced conditions to generate a deep set of expressed sequence tags for comparative profiling.

IV. Nucleic Acid and Protein Detection

A. Detection of RNA mRNA expression may be measured by any suitable method, including but not limited to, those disclosed below.

In some embodiments, RNA is detection by Northern blot analysis. Northern blot analysis involves the separation of RNA and hybridization of a complementary labeled probe.

In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes.

In still further embodiments, RNA (or corresponding cDNA) is detected by hybridization to a oligonucleotide probe. A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

B. Detection of Protein

In other embodiments, gene expression may be detected by measuring the expression of a protein or polypeptide. Protein expression may be detected by any suitable method. In some embodiments, proteins are detected by immunohistochemistry. In other embodiments, proteins are detected by their binding to an antibody raised against the protein. The generation of antibodies is described below.

Antibody binding may be detected by many different techniques including, but not limited to, (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

C. Detection Kits

In other embodiments, the present invention provides kits for the detection and characterization of proteins and/or nucleic acids. In some embodiments, the kits contain antibodies specific for a protein expressed from a DGTT gene. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

EXPERIMENTAL

The following examples are provided in order to demonstrate and further illustrate certain preferred embodiments and aspects of the present invention and are not to be construed as limiting the scope thereof.

The five DGTT genes were cloned from cDNA into pYES, a yeast shuttle vector capable of functioning in both yeast and bacteria (Invitrogen). The pYES vector contains an inducible promoter for the expression of genes, as well as selectable markers for bacteria and yeast. Cloning was successful for DGTT2 through DGTT5, but DGTT1 remains recalcitrant. DGTT2 through DGTT5 were also cloned with N-terminal and C-terminal His tags, in order to allow for detect and purify the recombinant protein in later experiments.

In order to most easily detect the activity of the putative DGTTs, the yeast strain H1266 was used as disclosed in Sandager et al. (2002) *Journal of Biological Chemistry* 277, 6478-6482 and Milcamps et al. (2005) *Journal of Biological Chemistry* 280, 5370-5377, both of which incorporated herein by reference. This strain contains knockouts for three of the four genes encoding enzymes with DGAT activity, leaving the yeast with roughly 1% of its original DGAT activity. While not limiting the present invention to any particular theory, it is believed that storage lipids are non-essential in yeast as disclosed in Sandager et al. (2002) *Journal of Biological Chemistry* 277, 6478-6482, thus the strain is able to grow without difficulty. The untagged pYES-DGTT2 through DGTT5 constructs were transformed into H1266, along with an empty vector control, and selected for transformants using dropout media lacking uracil. The transformed yeast were grown overnight in media containing glucose, and then transferred to 50-mL cultures containing galactose and raffinose to induce expression of the transgenes. 10-mL samples were collected after roughly two days for lipid extraction. The samples were extracted with a mixture comprising 2:1 methanol:chloroform (v:v), and run on a thin-layer chromatography (TLC) plate with 80:20:1 petroleum ether:diethyl ether:acetic acid as the solvent as disclosed in Bligh et al. (1959) *Canadian Journal of Biochemistry and Physiology* 37, 911-917, incorporated herein by reference. Olive oil was used as a standard to identify the corresponding TAG, free fatty acid and DAG bands in the samples. The plate was developed using an iodine solution to reveal the separated bands.

The empty vector control had no visible band level with the TAG band from olive oil (FIG. 16). The DGTT2 and DGTT3 constructs consistently exhibit a band that co-migrates with the olive oil TAG, with the band produced by DGTT2 being significantly more intense than that produced by DGTT3. Neither DGTT4 nor DGTT5 produced a visible band (as with the empty aforementioned vector) suggesting that they produce little or no TAG. Other bands running lower on the plate show no consistent pattern.

The TLC data indicates that DGTT2 and DGTT3 are capable of producing TAG in yeast. The darker band seen with DGTT2 suggests that it may have a higher rate of activity than DGTT3 in yeast. The DGTT2 construct may also be better expressed in the yeast, or better able to use the existing lipids. While not limiting the present invention to any particular theory, one possible interpretation for the negative results for DGTT4 and DGTT5 is that they lack DGAT activity. An additional possibility is that the conditions within the yeast are inappropriate for exhibiting full activity, e.g. they may require specific DAG or acyl-CoA substrates not produced by the yeast. Further TLC experiments have shown that DGTT4 produces a faint band, suggesting the possibility of such activity.

The yeast expression experiments described herein suggest at least two of the five putative DGTTs have DGAT activity in a heterologous system. A further embodiment of the present invention is the determination of both the function and activity of the putative DGATs identified in *Chlamydomonas*. Four of the five DGATs have been expressed in yeast, and two have been shown to produce TAG via TLC analysis. It may be possible to quantify the amount of TAG produced in the transformed yeast using gas chromatography (GC) based methods as disclosed in Milcamps et al. (2005) *Journal of Biological Chemistry* 280, 5370-5377 and Lardizabal et al. (2001) *Journal of Biological Chemistry* 276, 38862-38869, both of which are hereby incorporated by reference. Lipids could be extracted from the resulting yeast samples, with one part being converted directly into fatty acid methyl esters (to give the total amount of fatty acids) and a second part separated on a TLC plate to isolate the TAG before converting to FAME such that the amount of fatty acids esterified to TAG could be determined. Comparing the ratio of TAG to total fatty acids in the transformed and untransformed yeast could allow for the quantification of the differences in the levels of TAG produced. Such measurements would give a more accurate measure of the amount of TAG produced by DGTT2 and DGTT3, and further indicate whether DGTT4 and DGTT5, which appear negative on the TLC plates, have some slight activity.

Figure 17:
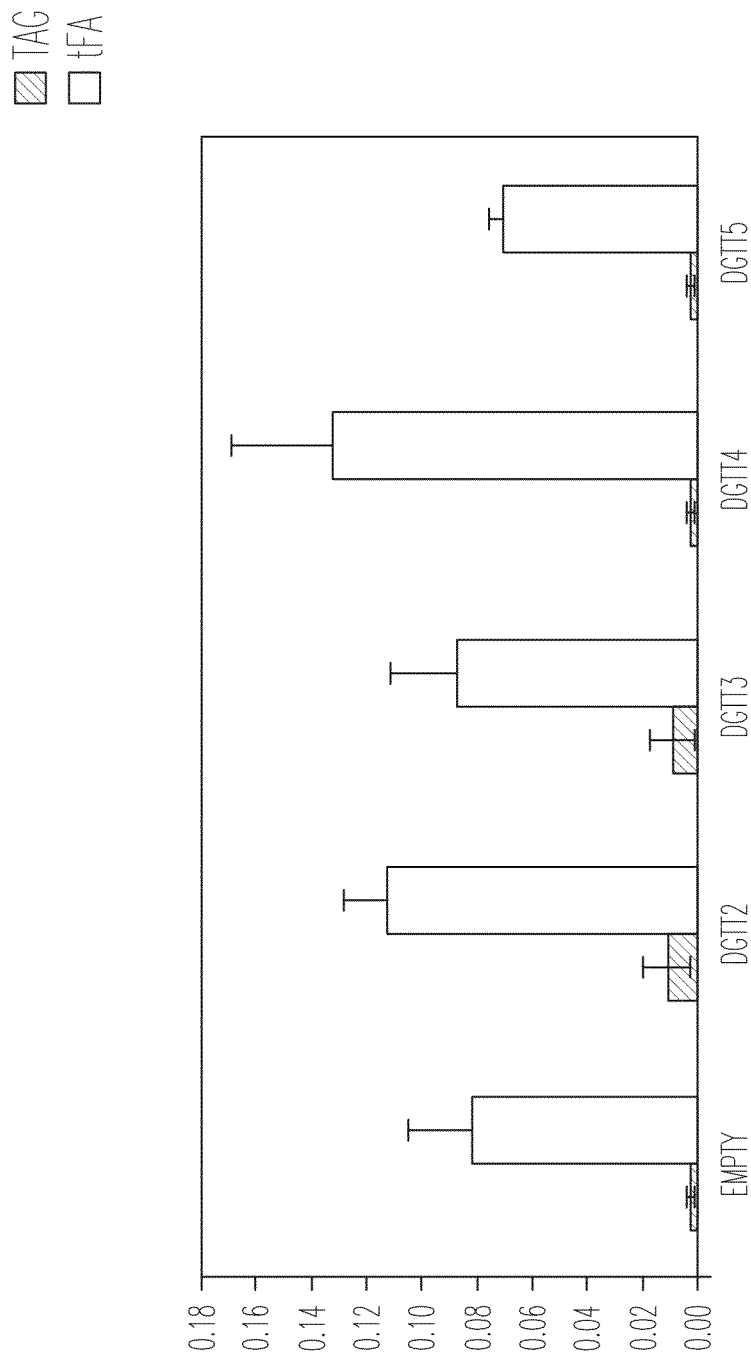
FIG. 17 is a graph showing GC results demonstrating TAG synthesis. The average mole amount of total lipid and TAG is shown, Total mole amount of lipids compared to total amount of TAG in yeast strain H1266 expressing DGTT constructs. The results are averages of four replicates. The amount of TAG is minimal, but DGTT2 and DGTT3 both show an increase, consistent with the results from the TLC experiments. DGTT4 and DGTT5 show no significant increase again consistent with earlier results.
Figure 18:
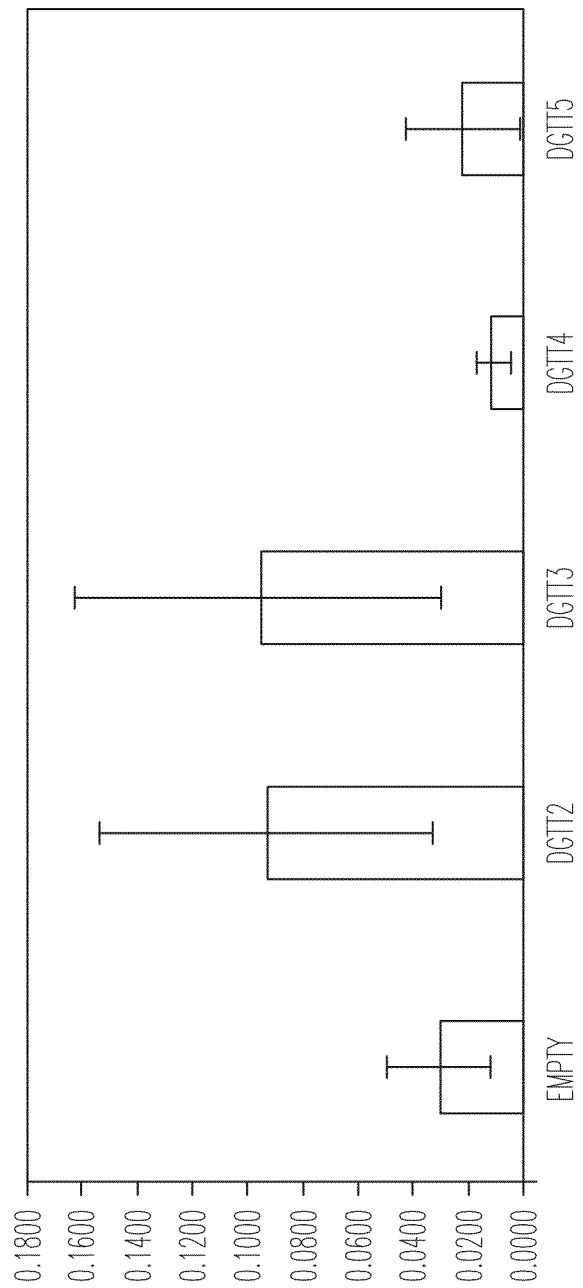
FIG. 18 is a graph of GC results showing the ratio of TAG to total lipid. Comparing the ratios of TAG to total lipid also shows that in yeast expressing DGTT2 and DGTT3, the proportion of lipids in the form of TAG increases, again consistent with earlier results. The amount of lipid in the form of TAG decreases slightly in yeast expressing DGTT4 and DGTT5, but are within the error margin.

GC experiments as described above have been performed, using the mutant H1266 expressing the pYES-DGTT2-5 constructs as shown in FIGS. 17 and 18. The results follow that of the TLC, with DGTT2 and DGTT3 showing a significant increase in TAG compared to the empty vector control, while DGTT4 and DGTT5 show little or no change.

---

We claim:

1. A method comprising:
   a) providing:
      i) algae, and
      ii) a vector comprising a nucleic acid encoding a diacylglycerol acyltransferase operably linked to a promoter, wherein said nucleic acid has greater than 90% sequence identity to a sequence is selected from the group consisting of SEQ ID NO: 5, SEQ ID NO: 8 and SEQ ID NO: 11;
   b) transfecting said algae with said vector under conditions such that said diacylglycerol acyltransferase is expressed.

2. The method of claim 1, wherein said expression is under conditions such that triacylglycerol (TAG), free fatty acid and/or diacylglyerol (DAG) is produced.

3. The method of claim 1, further comprising c) recovering triacylglycerol (TAG), free fatty acid and/or diacylglyerol (DAG) from said algae and/or oil from said algae.

4. The method of claim 1, wherein said expression is ectopic.

5. The method of claim 1, wherein said expression of said nucleic acid is upregulated between 1.5-3 fold relative to wild type expression of said nucleic acid.

6. The method of claim 1, wherein said algae is selected from the group consisting of *Chlamydomonas, Nannochloropsis, Dunaliella, Chlorella* and *Scenedesmus*.

7. The method of claim 1, wherein said algae is *Chlamydomonas reinhardtii*.

8. Algae transfected with a nucleic acid encoding a diacylglycerol acyltransferase operably linked to a promoter, wherein said nucleic acid has greater than 90% sequence identity to a sequence selected from the group consisting of SEQ ID NO: 5, SEQ ID NO: 8 and SEQ ID NO: 11.

9. The algae of claim 8, wherein said promoter is a heterologous promoter.

10. The algae of claim 8, wherein said promoter is an inducible promoter.

11. A non-algae plant tissue comprising a nucleic acid encoding an algae diacylglycerol acyltransferase operably linked to a promoter, wherein said nucleic acid has greater than 90% sequence identity to a sequence selected from the group consisting of SEQ ID NO: 5, SEQ ID NO: 8 and SEQ ID NO: 11.

12. The non-algae plant tissue of claim 11, selected from the group consisting of soybean (*Glycine max*), rutabaga (*Brassica napobrassica*), rapeseed (*Brassica napus*), canola, *Brassica campestris*, sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*) plant tissue.

13. The non-algae plant tissue of claim 11, selected from the group consisting of roots, shoots, leaves, pollen, seeds, tumors, and cells.

14. A method comprising:
 a) providing:
  i) a rutabaga, and
  ii) a vector comprising a nucleic acid encoding a diacylglycerol acyltransferase operably linked to a promoter, wherein said nucleic acid has greater than 90% sequence identity to a sequence selected from the group consisting of SEQ ID NO: 5, SEQ ID NO: 8 and SEQ ID NO: 11;
 b) transfecting said rutabaga with said vector under conditions such that said diacylglycerol acyltransferase is expressed.

15. A rutabaga plant tissue comprising a nucleic acid encoding a diacylglycerol acyltransferase operably linked to a promoter, wherein said nucleic acid has greater than 90% sequence identity to a sequence selected from the group consisting of SEQ ID NO: 5, SEQ ID NO: 8 and SEQ ID NO: 11.

16. A vector, comprising a nucleic acid encoding an algae diacylglycerol acyltransferase, wherein said nucleic acid is operably linked to a promoter, and wherein said nucleic acid has greater than 90% sequence identity to a sequence selected from the group consisting of SEQ ID NO: 5, SEQ ID NO: 8 and SEQ ID NO: 11.

17. The vector of claim 16, wherein said vector is a yeast shuttle vector.

* * * * *

SEQUENCE LISTING

```
<160> NUMBER OF SEQ ID NOS: 15

<210> SEQ ID NO 1
<211> LENGTH: 3417
<212> TYPE: DNA
<213> ORGANISM: Chlamydomonas reinhardtii

<400> SEQUENCE: 1
cgcgagctac ctgaggcgag aatgatgcgc gaaagctgcc ctccacgtcg cggggcctgt      60
aagggccgtt cacgatcaac tatttagtat atttgcacct gataaagcac tgctttcgcc     120
atgcaacgca aaatgaagct taagagtgct caactcaccg gacatccagg cgctagtatc     180
gctttctccc gcgaagtact atgcaaagta agcgttgtgc agagctggcc tctgggctc      240 tgtggcccat ggaccgcgac cagatgcgcg accgcgaccc atggaagctg cgcgaccgag     300
gtgcgctgca aagcacagaa accacacgct ctgtatagag gaaccgccaa aataagcata     360
atacacgagc ttgcagcact cactcaagtg agcgggcacc ttctgaaacc cttgacttgg     420
agcgtcgtga gcagaatgaa ccaactagag ctcgtgatgt gtcgattagc tgtgtcttgg     480
ttcctaatca cagctataag ccaagcatgg gtgtggcctc tgctcatcgg cacattgctt     540
tacgtgcaga gcaccacgct cacaattgcc ttcctgctgt aagtgcacta tatgtatggt     600
atctagcgtg ctatggagtt gtcgacgacg ggcgtttccg gggttccaac cgtcgccgaa     660
```

```
atcgaaatag aagcttgaca tggccgactt tgtgcgcagg tacctctatt atgttgtcgt    720
cggcccgggc tctaaagatg acgccaactg caagtggaag ccgaccttcc gcaagtaagg    780
ggcttcttag tctaagcggg gccaggctca tcagccgggg gcacgggata ggccgcgggt    840
gggctttctt gctacctaga tgcaatctac gccccaccgt aggccttatc tccgccctcc    900
acttaccccc atccactcgc aatcccaccc cgtacaccca cacacaaact cattcccaca    960
ggtggcatat ctggaaggtt atggcctctt acttccccgg cgcccgcctg attaagaccg   1020
ccgacctgga tccggctggc cgctatatat tcgtgagcca cccgcacggc gtcatcgcca   1080
tttccgactg gctggcattt gccacagagg cgctgggctt ctccaaactg ttcccaggtg   1140
cgtgacgaca tggcgtttgc gttactatga attctttgag tgcgcgtgcc gtattttgcc   1200
ttgtcggcag catgggccta atgcgacggt acggtcgtgt cggctcccac cttccgggct   1260
agacactagg atttcgtgga tcgagtcccc gatgcccacg cacgcctgcc cccacctcct   1320
gtgcccccgcc gctgcccctc aacctgcctc tcgacctgcc cctcaacctg ccctcaacc    1380
tgcctctcaa cctgcccctc aacctggccg ctcaaggccc cactaatggt cttggtctgg   1440
ttggttttgg agtaaactac cacacacgca taagttccgc aacactcgtc atacacacag   1500
acacacacag acaaacagac acacacacgc gcacacacac agacagacac acacactc    1560
acacacacac acacacggcc tgagtctggg actacgctgc aaactacggc accacgccaa   1620
cctgcccatt gccctgcccc gctgcacaca cgccaggcct ggacctgcgc tgcgccacgc   1680
tggcttcaaa cttctgggtg cctggtttgc gtgagtacat cctatcgcac ggcatgtgcg   1740
gcgtggggcg agacactctg gcgcgcgtgc tgacagggtg agtgggaggc tgaagagaaa   1800
gagcgtacgg taccagcaag ttgatgggtt gtgtttgcca gggggggcag gtgcatgccc   1860
aagcttacca aatagatcct gacttgtcaa agagggctga actgttaaat gcggtgcagc   1920
ttcctgggcc gttgccatgt gcctgtttgg aacacgcttc cccctccccg ccgatgtgtg   1980
cgcacacaga aagccgggcc gtgcggttgt gttggtggtg ggcggcgcgt ctgaggcgct   2040
gttggcggcg gagggaactt atgacctggt gagagggacg gaaggggtga ggactgatgg   2100
gggggagtca tgtcaagccc acactaacgg gaacctagga cataacctgg caggggggagg   2160
aatgttgcgg aggtaggtac ggagtgtggt gcaaaaaccc tagtggtgcg gtcccgagga   2220
acgtgtgccc acaacatgcg tgtgctcaca gcaagacagg aatagaggag cattgtgcaa   2280
accctcaaca ttgctgtgcc tgcatgcaaa ccctcgacgt cctgctcatg tgctcgtgct   2340
tccactacag gtgctgcgca accgcaaggg cttttgtgcgc ctggcgctgc agaccggcgc   2400
cagtctggtg ccggtgctgt cgtacggtga gacagacacc ttccacacct acatcccgcc   2460
gccctgcagc cgggcggccg cggtcatgaa gtgagcccg ccacgcatgg ttcacgttac   2520
cgccacgctt gatactttg gtatatgagg gagtccttcc gccccgctg aagccggcgt    2580
gaccctgcc aacaccagga taccatgggt ttacttgcct tgtcccttgc cttatgcaat   2640
gggttcggtt cagtatgggc tgcaacctgc aatccccccc ccgtgccccc cgcccatcat   2700
gaatgtaacc ccctcccccg cacgtgtgca cgcgaacctc ccgctcgtgc agggtgctga   2760
agcaggtgtt tggcttctcc acgcccctgt gctgggcac cggactgttc ggggggctggg    2820
gcatgctagc gctgcaggtg ccgctcactg tggtggtggg ggcacccata caggtggaca   2880
agtgagtgcc cggctgcgcg cgcgagggaa gtggttgggc atggctgcgg tagcttgcca   2940
gctagctgag gacaggagtg cgggtgtcag ctggcagtac cgacggctct gacaagcaag   3000
ctccccgtca catcccacgc gcccacgcgg cctcgccact gtgcggcccc gactgcacac   3060
```

```
gcacacatac acgctcacac acagggtgtc cagtcccacg gaggctgagg tggcggcgct    3120
gcataagacc tacacggagg cactgcagaa gctgtgggat gacacagtgg acaagtacgg    3180
caagggtgtc aagcggccgc tggccatcgt gcaatgatac tattactatt agctagggac    3240
agcagtggca gactggagcg gcggcagcag cagcagcagc gggggaggca gcggcggtgg    3300
cgtcagcagt ggcaggagcg gcggtagcag cggcaggagc agagggtgcg gtggaatcag    3360
ggcggcgcca gacttggcag cagcgttgtg cgtgcacggc acatgagtgg cactgag       3417

<210> SEQ ID NO 2
<211> LENGTH: 963
<212> TYPE: DNA
<213> ORGANISM: Chlamydomonas reinhardtii

<400> SEQUENCE: 2
atgcaaagta agcgttgtgc agagctggcc tctggggctc tgtggcccat ggaccgcgac     60
cagatgcgcg accgcgaccc atggaagctg cgcgaccgag ctataagcca agcatgggtg    120
tggcctctgc tcatcggcac attgctttac gtgcagagca ccacgctcac aattgccttc    180
ctgctgtggc atatctggaa ggttatggcc tcttacttcc ccggcgcccg cctgattaag    240
accgccgacc tggatccggc tggccgctat atattcgtga ccacccgca cggcgtcatc     300 gccatttccg actggctggc atttgccaca gaggcgctgg gcttctccaa actgttccca    360
ggcctggacc tgcgctgcgc cacgctggct tcaaacttct gggtgcctgg tttgcgtgag    420
tacatcctat cgcacggcat gtgcggcgtg gggcgagaca ctctggcgcg cgtgctgaca    480
ggaaagccgg gccgtgcggt tgtgttggtg gtgggcggcg cgtctgaggc gctgttggcg    540
gcggagggaa cttatgacct ggtgctgcgc aaccgcaagg gctttgtgcg cctggcgctg    600
cagaccggcg ccagtctggt gccggtgctg tcgtacggtg agacagacac cttccacacc    660
tacatcccgc cgcccctgca gccgggcgcc gcgtcatga aggtgctgaa gcaggtgttt    720
ggcttctcca cgcccctgtg ctgggcacc ggactgttcg ggggctgggg catgctagcg    780
ctgcaggtgc cgctcactgt ggtggtgggg gcacccatac aggtggacaa ggtgtccagt    840
cccacggagg ctgaggtggc ggcgctgcat aagacctaca cggaggcact gcagaagctg    900
tgggatgaca cagtggacaa gtacggcaag ggtgtcaagc ggccgctggc catcgtgcaa    960
tga                                                                  963

<210> SEQ ID NO 3
<211> LENGTH: 320
<212> TYPE: PRT
<213> ORGANISM: Chlamydomonas reinhardtii

<400> SEQUENCE: 3

Met Gln Ser Lys Arg Cys Ala Glu Leu Ala Ser Gly Ala Leu Trp Pro
1               5                   10                  15

Met Asp Arg Asp Gln Met Arg Asp Arg Asp Pro Trp Lys Leu Arg Asp
            20                  25                  30

Arg Ala Ile Ser Gln Ala Trp Val Trp Pro Leu Leu Ile Gly Thr Leu
        35                  40                  45

Leu Tyr Val Gln Ser Thr Thr Leu Thr Ile Ala Phe Leu Leu Trp His
    50                  55                  60

Ile Trp Lys Val Met Ala Ser Tyr Phe Pro Gly Ala Arg Leu Ile Lys
65                  70                  75                  80

Thr Ala Asp Leu Asp Pro Ala Gly Arg Tyr Ile Phe Val Ser His Pro
```

```
                    85                  90                  95
His Gly Val Ile Ala Ile Ser Asp Trp Leu Ala Phe Ala Thr Glu Ala
                100                 105                 110
Leu Gly Phe Ser Lys Leu Phe Pro Gly Leu Asp Leu Arg Cys Ala Thr
                115                 120                 125
Leu Ala Ser Asn Phe Trp Val Pro Gly Leu Arg Glu Tyr Ile Leu Ser
    130                 135                 140
His Gly Met Cys Gly Val Gly Arg Asp Thr Leu Ala Arg Val Leu Thr
145                 150                 155                 160
Gly Lys Pro Gly Arg Ala Val Leu Val Val Gly Gly Ala Ser Glu
                165                 170                 175
Ala Leu Leu Ala Ala Glu Gly Thr Tyr Asp Leu Val Leu Arg Asn Arg
                180                 185                 190
Lys Gly Phe Val Arg Leu Ala Leu Gln Thr Gly Ala Ser Leu Val Pro
                195                 200                 205
Val Leu Ser Tyr Gly Glu Thr Asp Thr Phe His Thr Tyr Ile Pro Pro
    210                 215                 220
Pro Cys Ser Arg Ala Ala Ala Val Met Lys Val Leu Lys Gln Val Phe
225                 230                 235                 240
Gly Phe Ser Thr Pro Leu Cys Trp Gly Thr Gly Leu Phe Gly Gly Trp
                245                 250                 255
Gly Met Leu Ala Leu Gln Val Pro Leu Thr Val Val Gly Ala Pro
                260                 265                 270
Ile Gln Val Asp Lys Val Ser Ser Pro Thr Glu Ala Glu Val Ala Ala
                275                 280                 285
Leu His Lys Thr Tyr Thr Glu Ala Leu Gln Lys Leu Trp Asp Asp Thr
    290                 295                 300
Val Asp Lys Tyr Gly Lys Gly Val Lys Arg Pro Leu Ala Ile Val Gln
305                 310                 315                 320

<210> SEQ ID NO 4
<211> LENGTH: 5233
<212> TYPE: DNA
<213> ORGANISM: Chlamydomonas reinhardtii

<400> SEQUENCE: 4
aagcgcggtg tagtatcccg ggtaatgttt taggatgcga ttaagtgtga tcagcgtata    60
gagatgaggc gtgcagacta cagcgcctgc tcgcgtgtgc aaagggccat gcagggggtct  120 gatgggggc gatggtgggc cgggagcgcg gggaacttct ctcgcggctt ccgggcatgc   180
attttgagct atttgcatgt ggatttgcaa cttttcgatat agttacgatt tgcgtgggac   240
cgccccattc acctaagaag cgggcctatt ggccgcccca cccgctggta aattgcgagt   300
ggggcgcgcg tcctagctgg atttaggcca tctgttttg attaaaattg caagtccgtg   360
tgtcgcgctc ccctaaacgt tggcgcgcca taatggcgat tgataaagca ccgacaaatg   420
tgcgaatttg gagcgatggc gtcacggaga agggcaagca aagcatcttc tcatcgctgg   480
tggctatgtt gacgctcttc atctactgtg gtgagtttgt agaggccgga taagtcgacg   540
cgaaccgcgc tccagagggg cgtcgaaaag tttcgttggc aacctgcggg gatgcgcgt    600 gtgaaccgtc acgctcgtgc caatcgacgc cacctggccg gcggccacct ccctgcggca   660
cccgtccccg cctggatcag gctggatgca tgtgctgctg gcgcttgtga tcctgtcctt   720 ctggtaccg tgggcgctgg tgacggtgct gctgctgtac tccaccctgc tgctgccgcc   780
taagccggtg cgtgtgcggg aagctccgcc gacgggcagc ggctccactg ccgcagggcc   840
```

```
cagtcgcatg gctgaagtgc tacttgtgtg gatcgggtgg tatgctgtcg gggctgccgt       900
taaccactgc atttggacgt atggaagcgg tccctgaagc agtcccaaag accgcatagt       960
gattcttgga ccctattcg tgttcgcgcg tgcaggtgct gtggggaccg gtctgtcgct       1020
cctggatctt ccagacctgg cgggagtgag tgctgggaat ccttgtgggt cattaggggc       1080
tagcggcctg gtcgtgccgc gccaggtgga cagggactgc attctgcatg cgtgcaggct       1140
ggagcagcgg tggaggcagc ggcagagcgg cggcaggcag cagcatggcc ccatgaggga       1200
gccagacacg tagcagtacc agcagtaccc aaaagcaaaa aaagagtcgt gtagcggcag       1260
cggcgagcta ccagtcagct gacaatgaca taagagagcc aagcacaaag aagggccgac       1320
cgtgctactg gcatctcgct ttagggcagg cagggctggg cgggcgagct ccgcagcacg       1380
cactccaaaa gcgtctgggg aagggcgtac gcggcctggc cgtagtcagg cgccgcgtgc       1440
tagtagccag tgaactaccg gcgccgcgct caccccttga agtcgacgac gtcgggcagg       1500
ggaaccggtc gggttgcggg gtgtggacct cgccaacgta tctaaccccg ccctgcccc       1560
tacttgcttc tgaaaggtgt tgaatcacct ccgtccaccc gccgcctctc gccaggtact       1620
tcaagttctc ttacgtgttt gatgaggtgc tggactcgaa gaagaagtac atcttcgcgg       1680
agtaagtttt gcgaggtgga catgtggttg ccgccttcaa ggctacacac agctagggtt       1740
ccatccttgt ggctgccatt tgctacacct gcggatgctg caccctttg tcgccctttc       1800
ttgcaggttc ccgcacggtg agctgtcgtg gaggcgtagg agtagcagcg gcagatgtgg       1860
tttgcgcgcg tgcatgggac ttggcctgga tctatgttgg tacccaggtt tactagttaa       1920
gggtttctcg ggagcgtgcg ctctaggagc tctgccagct actggtgctg cgttgcttgc       1980
cgtgctgccg agcacaatgg gaatggaacc gttgcggctg gcccataac ttcctgacgt       2040
acccgtgcac tgcgttgtac cctgtgcatc aagcacctta cggaacctct gactgcccca       2100
cccgccgccc accgctaccg cctaccttcc aaaaccaggt gtcttcccca tgggcccact       2160
gtgagttctg cgttttgcgt gcgcctggtt ctacgtcacg gattcttgga aagggttagc       2220
gctgggtacg agggggcgatt gacgcatttg gtaacgcttt gacgcactgg gagaacgagc       2280
ggcgctgaac ctcaccgttg ccgcggccgc catcacatta gcgggcgcac cagtagcgac       2340
cacagctact gccacgccat gccgggtcat ccttcgttct ggccgccgtc catgccctgg       2400
ccctcctcac gggtttgcgc atgtgcaccc gcagcattgg cgccacagaa tgccagatca       2460
tgtttcccgg ctttgacatc ttcgggctgg cggcgaatgt ggtgagtgcc tgtccgtggc       2520
cttgtggctg gtcgttttt tgagctttgg cgatttgctt tgtgtgagag agtagctgcc       2580
tgacttgtcc acgcctgaga tctttggcgt ttacactccc aggtgttcac ggtcccttc       2640
tggcggcatt tcgtggcgtg gctgggctcc gtgccggcca ccacgcgca cttcaagcgg       2700
gtgctgaagc aaggaagcgt ggcggtcatc gtgggaggca tcgcaggtgc gtggcggctg       2760
gcggctgcta gtgctgtgt ggtggtgcta ggcgtgtgcg tgtgggtcgg tgtaactgga       2820
gcttggctgg ggtgtgtatg ggcgtcagca cataagcagg gttctgtcaa ggacagatgc       2880
cgctgcggcg atgtgctagc agggaggtta gttaggcatg ggaccgtgct atatgggta       2940
cgcaagggtt ttgcccggca ttacctagac gcaagctcgg ggttggctgt cgaagaagat       3000
ggccaatgtg gggctacgag ggtgccgggc tgtacctgcg gtccacatgc acgtgtggtg       3060
cgggcggcat cgccaccagc agtcggctgc cgagcttgca gcgagaacca ctgactctgg       3120
tgtatgtcac cgaccccgcc gcacccgcc cgcagagatg tacatgcaga gccccacgaa       3180
```

| | |
|---|---|
| ggagcaggtg acgaggcggg cgccggcggg tgtgcggggc accaccggca gccaatgtgc | 3240 |
| cgccgtgtcg catgttgcca gtcgtaaaca gctgatcgga tgcaatgcga tgcgatgtgc | 3300 |
| gtcaagcagt atgcgctatg gctgacgcac gtgtctgccg tacgatcgaa cagatcatgt | 3360 |
| tgaaggaccg caagggcttt gttcgtgtgg cggtggagga gggcgtggat ggcggcatcg | 3420 |
| tgccggtcta ccactttggc aactctcagg tgggtgtgaa gctccggaca agggagcgag | 3480 |
| cgcacgtggg ggcgagcgta cgtacatggg agcgggagga ggaagcgagc gcgggaatgt | 3540 |
| aattaaattt ggccgtgcgc tgccaacagc cactgagggc ttgctcagct gcgctcccgg | 3600 |
| cttagcgccg cctacccata gccttgcagc ctggcctcac gcaccaatag gtaccgcctg | 3660 |
| cccacctgca tctatccacg tacgcctgtt tccgtctttc gcttcggctt tccctgctcc | 3720 |
| acgcgccccg gcgcggacct gcaaatgggc tcggccacaa ggcctcctcc cctccaccaa | 3780 |
| cacttccacc tccacctccc gcgccccccag gtgctggact tcggccccca ggccatggcc | 3840 |
| agtgtgtccc gccggctgcg tgcggccctg ggcttcctgt acggagtggc ctacctgccc | 3900 |
| ctgcccaggt gcgtgtgcgt atatgcgtgt gcttgtgcgt gtgcgtgtgc gtgtgcgtgt | 3960 |
| gcgtgtgcgt gtgcgtgtgc gtgtgtgtgt gtgtgtgtgt gcgtgcgtgt gcgcgtgtgt | 4020 |
| gcgcgtgcgt gtgggcccg cacttgcatg ttgtgcggta tcgcgcatgt atgtgtgtcg | 4080 |
| ctcctgtatc cgccctgcaa gcccgcagca ccgcggcctg ctgcttatgc tgcctcgccc | 4140 |
| gctcacccgg tgccgtccgc acggctgcgc ctcccttgca ctcatggaca caggcgccgc | 4200 |
| aacatttaca tggtgtgcgg caagcccgtt cccgtcacgc gcaccgcccg cgacgacccc | 4260 |
| aaggtgtgta tgtgtgtgtt aaagagcaca aggaaaacat tgcgcaaaga cagtatgcga | 4320 |
| tgcagcaaag cgactgttta cggatgttac atgaacttac ctcgcatgcc cgctgcggtg | 4380 |
| agccgccgga cttaccaacc ggaaatcgcg caacccccgc tactcaaacc tcgagggggc | 4440 |
| attagcgtcc acacgctctc aagggtgcaa acccaagcat gtgctcacgg taccgtgtgt | 4500 |
| gtgtatgtat gtgtgcatgt gtgtgttggt gggcggggc ggttgaagcg ttgttggggc | 4560 |
| ctgcagggca attcgtcaag ccccagggcg catgacgaat tgacaagagc attgccggct | 4620 |
| aggtcggctc cgtatgcatg cgtcctctgg ccgacatacc agtccttaag ccccttgctc | 4680 |
| gagcacgacc cctatccgtt ttgccccccaa acaatggtac caccgtctcc tgcctgcctt | 4740 |
| ccaccctgta tcccgccgcc gcagtttgag gaggtggttg acgccactca cgccgctgtg | 4800 |
| atggcggccc tgcaggaggc ctacgaccgc cacaagaccg agtacggctg ggccgaccga | 4860 |
| ccgctggtca tcagctgagc gggcggcggt tgaatgctg ggatctgttg ctggtgctga | 4920 |
| tttgtaagtg tggcttggcg caatacaggc ggcggcagca gtggcggcgg cagcacccag | 4980 |
| ggtagcagga gctgcgcagc cgaaagtgaa ggcgctggga gagttgtgcg tgcaacacag | 5040 |
| agagggaggg aaagggcgac cagaggccaa ggggagacca cgcagcgcgt cgcagcgaca | 5100 |
| tgggcatgcg tagtgtgctg acggccgcag tctgagaggg aagtgtgaaa gtcaggaatg | 5160 |
| aggctttctg gggacgcacg cgcgcatgca tggcctcagc tggtggccat gactccggtg | 5220 |
| cgggactgcg ggc | 5233 |

<210> SEQ ID NO 5
<211> LENGTH: 1322
<212> TYPE: DNA
<213> ORGANISM: Chlamydomonas reinhardtii

<400> SEQUENCE: 5

| | |
|---|---|
| ggatttgcaa ctttcgatat agttacgatt tgcgtgggac cgccccattc acctaagaag | 60 |

```
cgggcctatt ggccgcccca cccgctggta aattgcgagt ggggcgcgcg tcctagctgg    120
atttaggcca tctgttttttg attaaaattg caagtccgtg tgtcgcgctc ccctaaacgt    180
tggcgcgcca taatggcgat tgataaagca ccgacaaatg tgcgaatttg agcgatggc    240 gtcacggaga agggcaagca aagcatcttc tcatcgctgg tggctatgtt gacgctcttc    300
atctactgtg ctggatgca tgtgctgctg gcgcttgtga tcctgtcctt ctggtaccgc    360
tgggcgctgg tgacggtgct gctgctgtac tccaccctgc tgctgccgcc taagccggtg    420
ctgtggggac cggtctgtcg ctcctggatc ttccagacct ggcgggagta cttcaagttc    480
tcttacgtgt ttgatgaggt gctggactcg aagaagaagt acatcttcgc ggagttcccg    540
cacggtgtct cccccatggg cccactcatt ggcgccacag aatgccagat catgtttccc    600
ggctttgaca tcttcgggct ggcggcgaat gtggtgttca cggtcccctt ctggcggcat    660 tcgtggcgt ggctgggctc cgtgccggcc accacacgcg acttcaagcg ggtgctgaag    720
caaggaagcg tggcggtcat cgtgggaggc atcgcagaga tgtacatgca gagccccacg    780
aaggagcaga tcatgttgaa ggaccgcaag ggctttgttc gtgtggcggt ggaggagggc    840
gtggatggcg catcgtgcc ggtctaccac tttggcaact ctcaggtgct ggacttcggc    900
ccccaggcca tggccagtgt gtcccgccgg ctgcgtgcgg ccctgggctt cctgtacgga    960
gtggcctacc tgccctgcc caggcgccgc aacatttaca tggtgtgcgg caagcccgtt    1020
cccgtcacgc gcaccgcccg cgacgacccc aagtttgagg aggtggttga cgccactcac    1080
gccgctgtga tggcggccct gcaggaggcc tacgaccgcc acaagaccga gtacggctgg    1140
gccgaccgac cgctggtcat cagctgagcg ggcggcggtt gaatggctgg gatctgttgc    1200
tggtgctgat ttgtaagtgt ggcttggcgc aatacaggcg gcggcagcag tggcggcggc    1260
agcacccagg gtagcaggag ctgcgcagcc gaaagtgaag gcgctgggag agttgtgcgt    1320
gc                                                                   1322

<210> SEQ ID NO 6
<211> LENGTH: 324
<212> TYPE: PRT
<213> ORGANISM: Chlamydomonas reinhardtii

<400> SEQUENCE: 6

Met Ala Ile Asp Lys Ala Pro Thr Asn Val Arg Ile Trp Ser Asp Gly
1               5                   10                  15

Val Thr Glu Lys Gly Lys Gln Ser Ile Phe Ser Ser Leu Val Ala Met
            20                  25                  30

Leu Thr Leu Phe Ile Tyr Cys Gly Trp Met His Val Leu Leu Ala Leu
        35                  40                  45

Val Ile Leu Ser Phe Trp Tyr Arg Trp Ala Leu Thr Val Leu Leu
    50                  55                  60

Leu Tyr Ser Thr Leu Leu Leu Pro Pro Lys Pro Val Leu Trp Gly Pro
65                  70                  75                  80

Val Cys Arg Ser Trp Ile Phe Gln Thr Trp Arg Glu Tyr Phe Lys Phe
                85                  90                  95

Ser Tyr Val Phe Asp Glu Val Leu Asp Ser Lys Lys Lys Tyr Ile Phe
            100                 105                 110

Ala Glu Phe Pro His Gly Val Phe Pro Met Gly Pro Leu Ile Gly Ala
        115                 120                 125

Thr Glu Cys Gln Ile Met Phe Pro Gly Phe Asp Ile Phe Gly Leu Ala
    130                 135                 140
```

Ala Asn Val Val Phe Thr Val Pro Phe Trp Arg His Phe Val Ala Trp
145                 150                 155                 160

Leu Gly Ser Val Pro Ala Thr Thr Arg Asp Phe Lys Arg Val Leu Lys
                165                 170                 175

Gln Gly Ser Val Ala Val Ile Val Gly Gly Ile Ala Glu Met Tyr Met
            180                 185                 190

Gln Ser Pro Thr Lys Glu Gln Ile Met Leu Lys Asp Arg Lys Gly Phe
        195                 200                 205

Val Arg Val Ala Val Glu Glu Gly Val Asp Gly Ile Val Pro Val
210                 215                 220

Tyr His Phe Gly Asn Ser Gln Val Leu Asp Phe Gly Pro Gln Ala Met
225                 230                 235                 240

Ala Ser Val Ser Arg Arg Leu Arg Ala Ala Leu Gly Phe Leu Tyr Gly
                245                 250                 255

Val Ala Tyr Leu Pro Leu Pro Arg Arg Arg Asn Ile Tyr Met Val Cys
            260                 265                 270

Gly Lys Pro Val Pro Val Thr Arg Thr Ala Arg Asp Asp Pro Lys Phe
        275                 280                 285

Glu Glu Val Val Asp Ala Thr His Ala Ala Val Met Ala Ala Leu Gln
290                 295                 300

Glu Ala Tyr Asp Arg His Lys Thr Glu Tyr Gly Trp Ala Asp Arg Pro
305                 310                 315                 320

Leu Val Ile Ser

<210> SEQ ID NO 7
<211> LENGTH: 3858
<212> TYPE: DNA
<213> ORGANISM: Chlamydomonas reinhardtii

<400> SEQUENCE: 7

```
gaagcccgcc ttgcgggaca gcatgtttgc gagggccatt ttgaatctaa ttgaggtggg      60
ctaaacgggc ttccacacga agctgtgcaa aacttggact cctttgcaag ttgccgaggt     120
cgccatgca gcgactcgcg cgcatggtcc cccgcggtg aacaaatgcc gctcgccttc       180
tcacgtaaac aatataactt gcttaccaat actgtttgca atcgtatacg tgcggcgcag     240
cgtgcgggat acgtcccata acaccactg cataatccgc gttagccaac gagcttcccc      300
agcgcccccg cgcgtgcact ggcggctttc ggcactagcc aagcctttag gcgtagactg     360
ggcgcctgag gcgcggacac acagccgcac cgagacgttg agcgtttcat ccgagctcac     420
tcacgcgcat cgccggcggg acactgcgca cggagcccgc gcgcgtggac acctgggccc     480
ctgcacgaag gcccctgcg agacggaagc agatggcagg tggaaagtca acggcacgg       540
gcgcggcgga cgcgcacgtg cgtacctcgc acttgaccct gaaagctggg gaggacccgc     600
ccccgaatgt tcgcatctac agtgacggtg agcccggata catgcattac acgacagcag     660
acctcatgct ccggcgtatt atgacatcag ggtggacggc tgctgtgcgg cgtatagggc     720
ggctacagcc gtgggcacaa acgcagcaca tgccttacct ctcctcacct gcaatgctac     780
tgccgccgca ggcatcaagc cggacgcgcg gcagaacctg cttgttcaga tcctggccgg     840
catcacgatg tcgatttatg taggcaagtg cattcagctg acaggaaggt ctgggcgcgc     900
tcccagggct ccaactggat agtgattccc acactcggac agcggacacg gccgcacata     960
gcggtaacag cacattcggt cggggccttg ggactgtacc cggcatctaa gcatgccgcg    1020
taactactcg cgcaccgtgc atccgcaacc aaaactttgc ctccattctt gagctcaacc    1080
```

```
caacctcatt ccttgtttgg acgttccccg tcccaaggct tcatgaacta tttcatgctg    1140
ctggtggtgc tctcctactg gagccgcatc tgccgctatg tggtcctggc gctgctaggc    1200
acactggcgc tgccctgcaa gcccgtgctg tggcctgcct tcaacaagct gtggatcttc    1260
aagacctggg tcactactt ccactacagg tgcacagcaa cgggcggctg aatgccttgg     1320
tgtatcgctg gcgggcagga cgtgggcccg gtctgcatg tgctgtgccg ctgcgctgcg     1380
ttgctactcc tgcgctttgc tgcacggtcg cggcgagcag cggccggcga tgaatttaga    1440
agacactaca atctctgtat ttgtcgtcat gcttcgtgcg tgtagtttcc tgattgagga    1500
gccgcttgac cccaacaagc gctacatctt tgtcgagtga gtgcggggac tgcagcacag    1560
gcattctaca tgtggccagg aagtcaaggt tgtattgttg gcttcggcta ctagtatgct    1620
cattttctta ctcccagcca ctttcgctgc cgccctcacc ttgcaggttc ccgcacggcg    1680
cgttccccat tggtgagtgg ttgtttgtcc ggtgacggct gtgcgattac ccgactggac    1740
tgactggggt cacgcatggt gcttggcctg gctcagctcc gcaggtgcct tgtttgtcgc    1800
aacgccttcg ggcagtgcag taatgcgccc gcattccttc actcgtcctt cccccccgcag   1860 gtcccatcgt ggcgggcacg ctcatgcaga ctctgttccc gcacatgatg atctacagcg    1920
tggccgcctc cgtcgtgttc tacatcccct tctggcgcca tttcatcacg taagcttgca    1980
acaggacaga ctcccgctgg gtctacagca gtcgccgaca tcccgatttc gctaggaaga    2040
gccgtaccat gccgaatatg ctgccgatct ctcggattca ctgtgttgca aaccctgggc    2100
gctgttgcag gtggatcggc tcggtgcccg caacgcccgg caacttcaag cggctgctga    2160
agaagggcag tgtggcggtg gtggtgggcg gcattgccga ggtaggcgcg cctaggcgat    2220
gggatcaggg tcatgctctg agaggggtcg cgaagccatt caggactggc cactccggcc    2280
aaaccagcta ccatacgcgc tgttcaaacc ctcccttttcc cgctcctgct tgcccacctg    2340
ccccgtccat ctgcagatgt acatgggcaa caagaagaag gagcgcatta agctagtggg    2400
ccgccgcggc ttcgcacgca tcgcgctgga ggagcaggtg gacggcattg tgtgcgtgta    2460
ctacttcggt cagagccaag tgctggactt cgggccctcc tggctggcgg actttagccg    2520
ccgcatgcgc accagcttcg gctacctcac gggatggatg gggctgccgg tgccgcggcc    2580
catccccatc tacgtgagtg ggggagtcgg gggcccggc ctggtggcaa gtcgctttca     2640
cgaaactcgg cgctctgtgt acagtatgtg gccaagaagt agaggggaag gaaaacggat    2700
ggcaaccacg aatactcaaa agccatacgc cacggaaggg tcagacgcta gggatgtatc    2760
gttgctgctc ggctggcggc cacatcattc agcactgccc gtcaccggtc tcgcggcacg    2820
tgcggctgca atgctcgctg catccgcgtc aaccttgccg ccactgctcg tgtacacgca    2880
cacgcagatg gtgaatggga agcccatccc ggtgcccaag gtggctcgtg actcgcccga    2940
gttcgacaag gaggtggata agctgcttga cgccaccatc acggagctgg gcgagatgta    3000
caacaggcac agaggcgagt acggctgggg cgaccgcccg ctgtccatcg agtagatgcc    3060
caacaagtgg attggcacag tggtgccctt gaaatggcat ggccagagtg aaagcgggat    3120
ggatcgttgg agatggttat ggaggggagg aaggaatatc ttgaaaaggc cacgcggatg    3180
ggttcgtgag gcatgcaggg cctttcgggt tggatgggg tcgcactagt cgcacgtgcc      3240
gcgtgggcac gtgtgtgccg taaaccttt atggtatggt gtgtcaagac tagtctagac     3300
gtaccgatgg ctatatggta gctcagctat gcgaaaagct gcgaaacggg ctggcattgc    3360
ctttgggtga acgtgcaagt gttgtgttta gatgcaaggc aggtggatgc agttgtaggt    3420
```

| | |
|---|---:|
| gtagcagacc tttacatcag cacagttggc tagataggtc gcgtcagcca aggagggagc | 3480 |
| tctgcgtttg attgggttga tgctgccagc aggcggcatt aaaatggacg tggcaaggga | 3540 |
| gcaatagagc ctttgaaaga atgccatatc ctgaagacac acgtgcatga cgcaagggtc | 3600 |
| ccgttgctga gctcctgact tgatcatccc ttggatgctg tcacgcaatg tgcttcaagt | 3660 |
| gcgccgctac taacctacta ccgtatggtc acgggtgctc aacatatcac cgctgctgag | 3720 |
| cggtcattac ctgcagccca agtgcccaac cctgcccagt ggaggcccac cctggacttg | 3780 |
| cgggtcacca tcatcctcca cagccccact tgcacagtct gacactgcag gacagaacgc | 3840 |
| ggggcattta ggacgcgg | 3858 |

<210> SEQ ID NO 8
<211> LENGTH: 1956
<212> TYPE: DNA
<213> ORGANISM: Chlamydomonas reinhardtii

<400> SEQUENCE: 8

| | |
|---|---:|
| gcttaccaat actgtttgca atcgtatacg tgcggcgcag cgtgcgggat acgtcccata | 60 |
| aacaccactg cataatccgc gttagccaac gagcttcccc agcgccccg cgcgtgcact | 120 |
| ggcggctttc ggcactagcc aagcctttag gcgtagactg ggcgcctgag gcgcggacac | 180 |
| acagccgcac cgagacgttg agcgtttcat ccgagctcac tcacgcgcat cgccggcggg | 240 |
| acactgcgca cggagcccgc gcgcgtgac acctgggccc ctgcacgaag ggcccctgcg | 300 |
| agacggaagc agatggcagg tggaaagtca acggcacgg gcgcggcgga cgcgcacgtg | 360 |
| cgtacctcgc acttgaccct gaaagctggg gaggaccccgc cccgaatgt tcgcatctac | 420 |
| agtgacggca tcaagccgga cgcgcggcag aacctgcttg ttcagatcct ggccggcatc | 480 |
| acgatgtcga tttatgtagg cttcatgaac tatttcatgc tgctggtggt gctctcctac | 540 |
| tggagccgca tctgccgcta tgtggtcctg gcgctgctag gcacactggc gctgccctgc | 600 |
| aagcccgtgc tgtggcctgc cttcaacaag ctgtggatct tcaagacctg gcgtcactac | 660 |
| ttccactaca gtttcctgat tgaggagccg cttgacccca caagcgcta catctttgtc | 720 |
| gagttcccgc acggcgcgtt ccccattggt cccatcgtgg cgggcacgct catgcagact | 780 |
| ctgttcccgc acatgatgat ctacagcgtg gccgcctccg tcgtgttcta catcccttc | 840 |
| tggcgccatt tcatcacgtg gatcggctcg gtgcccgcaa cgcccggcaa cttcaagcgg | 900 |
| ctgctgaaga agggcagtgt ggcggtggtg gtgggcggca ttgccgagat gtacatgggc | 960 |
| aacaagaaga aggagcgcat taagctagtg ggccgccgcg gcttcgcacg catcgcgctg | 1020 |
| gaggagcagg tggacggcat tgtgtgcgtg tactacttcg gtcagagcca agtgctggac | 1080 |
| ttcgggccct cctggctggc ggactttagc cgccgcatgc gcaccagctt cggctacctc | 1140 |
| acgggatgga tggggctgcc ggtgccgcgg cccatcccca tctacatggt gaatgggaag | 1200 |
| cccatcccgg tgcccaaggt ggctcgtgac tcgcccgagt tcgacaagga ggtggataag | 1260 |
| ctgcttgacg ccaccatcac ggagctgggc gagatgtaca acaggcacag aggcgagtac | 1320 |
| ggctggggcg accgccgct gtccatcgag tagatgccca acaagtggat tggcacagtg | 1380 |
| gtgcccttga atggcatgg ccagagtgaa agcgggatgg atcgttggag atggttatgg | 1440 |
| agggagggaa ggaatatctt gaaaaggcca cgcggatggg ttcgtgaggc atgcagggcc | 1500 |
| tttcgggttg gatgggggtc gcactagtcg cacgtgccgc gtgggcacgt gtgtgccgta | 1560 |
| aaccttttat ggtatggtgt gtcaagacta gtctagacgt accgatggct atatggtagc | 1620 |
| tcagctatgc gaaaagctgc gaaacgggct ggcattgcct ttgggtgaac gtgcaagtgt | 1680 |

-continued

```
tgtgtttaga tgcaaggcag gtggatgcag ttgtaggtgt agcagacctt tacatcagca   1740
cagttggcta gataggtcgc gtcagccaag gagggagctc tgcgtttgat tgggttgatg   1800
ctgccagcag gcggcattaa aatggacgtg gcaagggagc aatagagcct ttgaaagaat   1860
gccatatcct gaagacacac gtgcatgacg caagggtccc gttgctgagc tcctgacttg   1920
atcatccctt ggatgctgtc acgcaatgtg cttcaa                             1956
```

<210> SEQ ID NO 9
<211> LENGTH: 346
<212> TYPE: PRT
<213> ORGANISM: Chlamydomonas reinhardtii

<400> SEQUENCE: 9

```
Met Ala Gly Gly Lys Ser Asn Gly Thr Gly Ala Asp Ala His Val
 1               5                  10                  15

Arg Thr Ser His Leu Thr Leu Lys Ala Gly Glu Asp Pro Pro Asn
                20                  25                  30

Val Arg Ile Tyr Ser Asp Gly Ile Lys Pro Asp Ala Arg Gln Asn Leu
                35                  40                  45

Leu Val Gln Ile Leu Ala Gly Ile Thr Met Ser Ile Tyr Val Gly Phe
 50                  55                  60

Met Asn Tyr Phe Met Leu Leu Val Val Leu Ser Tyr Trp Ser Arg Ile
 65                  70                  75                  80

Cys Arg Tyr Val Val Leu Ala Leu Leu Gly Thr Leu Ala Leu Pro Cys
                 85                  90                  95

Lys Pro Val Leu Trp Pro Ala Phe Asn Lys Leu Trp Ile Phe Lys Thr
                100                 105                 110

Trp Arg His Tyr Phe His Tyr Ser Phe Leu Ile Glu Glu Pro Leu Asp
                115                 120                 125

Pro Asn Lys Arg Tyr Ile Phe Val Glu Phe Pro His Gly Ala Phe Pro
                130                 135                 140

Ile Gly Pro Ile Val Ala Gly Thr Leu Met Gln Thr Leu Phe Pro His
145                 150                 155                 160

Met Met Ile Tyr Ser Val Ala Ala Ser Val Val Phe Tyr Ile Pro Phe
                165                 170                 175

Trp Arg His Phe Ile Thr Trp Ile Gly Ser Val Pro Ala Thr Pro Gly
                180                 185                 190

Asn Phe Lys Arg Leu Leu Lys Lys Gly Ser Val Ala Val Val Gly
                195                 200                 205

Gly Ile Ala Glu Met Tyr Met Gly Asn Lys Lys Glu Arg Ile Lys
                210                 215                 220

Leu Val Gly Arg Gly Phe Ala Arg Ile Ala Leu Glu Glu Gln Val
225                 230                 235                 240

Asp Gly Ile Val Cys Val Tyr Tyr Phe Gly Gln Ser Gln Val Leu Asp
                245                 250                 255

Phe Gly Pro Ser Trp Leu Ala Asp Phe Ser Arg Arg Met Arg Thr Ser
                260                 265                 270

Phe Gly Tyr Leu Thr Gly Trp Met Gly Leu Pro Val Pro Arg Pro Ile
                275                 280                 285

Pro Ile Tyr Met Val Asn Gly Lys Pro Ile Pro Val Pro Lys Val Ala
                290                 295                 300

Arg Asp Ser Pro Glu Phe Asp Lys Glu Val Asp Lys Leu Leu Asp Ala
305                 310                 315                 320
```

Thr Ile Thr Glu Leu Gly Glu Met Tyr Asn Arg His Arg Gly Glu Tyr
            325                 330                 335

Gly Trp Gly Asp Arg Pro Leu Ser Ile Glu
            340                 345

<210> SEQ ID NO 10
<211> LENGTH: 4005
<212> TYPE: DNA
<213> ORGANISM: Chlamydomonas reinhardtii

<400> SEQUENCE: 10

| | | | | | |
|---|---|---|---|---|---|
| tctgctggat | agcgagacaa | gaattcgctt | gcacaatcat | tgggcgggaa | gctttcctcg | 60 |
| ggtgttcgca | aagctcccat | ggagttcttt | attaaagcat | gtaactgaca | atcagtataa | 120 |
| ctagcctagt | tacgtagcgc | aatccatgct | tgcttgcaaa | gttgtaaacc | agtaaacgag | 180 |
| cgtcgctttt | atttccattc | ttcaaggagt | gctgtatgag | tctataaacc | agtcaggagc | 240 |
| ttgcctcttt | cttagggccg | aacgagaatg | ccgctcgcaa | agctgcgaaa | cgtggtgctg | 300 |
| gagtacgcgg | ccatagccat | ctacgtcagg | taattttgct | taagacgcga | ctgttctgtg | 360 |
| aaactgacga | gctcaggaaa | tcggctgggc | cgaaccacca | tggcgtctcc | cgtccaaagc | 420 |
| gttcttgcgc | accccctccc | ccgcccaagc | tctcgccccg | ctgccacacg | ccctgcaacc | 480 |
| ccaagcctcc | aaccccaaa | ccccatcct | ctccacagcg | ccatctacac | ctcggtggtg | 540 |
| ctgctgccct | cggcgctcgc | gctgttctac | ctgtttgggg | ccaccagccc | ctcggcctgg | 600 |
| ctgctgctag | ccgccttcct | ggccctcacc | ttcacgccgc | tgcagctgac | caccggtgcg | 660 |
| ctgtcggagc | ggttcgtgca | gttcagtgtg | gcgcgggcgg | cggcctactt | ccccaccccgc | 720 |
| gtggtggtca | cggacccgga | ggtgagggcg | ctgtggggc | gctgtacggg | gggctgctgg | 780 |
| gggtgggggg | cgaaggttgt | gggggccgga | cctgtgggga | aaggggggagg | agtagtctgg | 840 |
| ggtcacgagg | gaggagacag | ggggcggggc | tgcacggtta | aggcagtgga | aactgggtaa | 900 |
| gagcatcgg | aacagggaac | ggtgggcagt | gcatcaggcg | taggtgagtg | gttgcgtgcc | 960 |
| gatgaccgga | gcaggtgggg | aaggcggggt | ttattgcact | cccaaaagaa | accaagaccc | 1020 |
| ggaaccagcc | cacaaagggt | atcgtagtgg | catcgggttg | aacggcgaca | ccaccgccct | 1080 |
| gcattggctt | tggcattgac | tgcggtcctg | tgccctcccc | cccccaggc | cttccgcact | 1140 |
| gaccgcggct | acttgttcgg | attctgcccg | cactcggctc | tgcccatcgc | actgccatc | 1200 |
| gccttcgcca | ccacctcgcc | gctgctgccc | aaggagctgc | gcggccgcac | acacggcttg | 1260 |
| gcgtcgtccg | tgtgcttcag | cgcgcccata | ggtgtgtgtg | gcgggggggg | cggcgcgggg | 1320 |
| ggaggatggg | ccgggagagc | acccggtgac | aggttggtgg | tgtggcgggt | tgttctccgg | 1380 |
| gtaggtggcg | aagccgtcct | gtgctctcca | ccgctaccgc | gactgctacc | gtggctgctc | 1440 |
| cccagaacat | cacccacatg | tgtgttccct | ctcctgctcc | tcctacgcct | ccctcctcct | 1500 |
| cctccctccc | cacgtgctgc | agtgcggcag | ctgtactggt | ggctgggcgt | gcggcccgcc | 1560 |
| acgcggcaga | gcatcagcgg | cctgttgcgg | gcgcgcaagg | tggcggtgct | ggtgccgggg | 1620 |
| ggcgtgcagg | aggtgctcaa | catggagcac | ggcaaggagg | tgtgtgcggc | tggggtgtgt | 1680 |
| gtgtcgtgtg | cgtgtgcgtg | tgtgttagga | aagcgcaaag | gagagggccg | acaccgtgct | 1740 |
| tgcaaaatgc | agcaagaaag | caagcgtttt | gtgtgtgaca | agagaaacga | acgagtgcgt | 1800 |
| gtgtgtgtgt | gtgtgttaaa | cacaaaaaca | aacggaacaa | agccgctgtg | tgtgtgtgtg | 1860 |
| tgtgtgtgt | gcgtcgttag | gcgttgtttg | gtataatgtt | cggtgagcgt | gtgaggttgc | 1920 |
| gcggcaaccct | tacggtatgt | ggggttggcg | agattcaatg | caaacagcgc | actgtgacgc | 1980 |

```
cgcatggaga gctctgcaca gcattgctag catacaacca tcaccctggc cctcacactg    2040
cttggccccc cctttgacaa ttgggaccta catggttggg ctcgaacatt taaccaccct    2100
gtggacgggt tctgggtctt ggcttctttg ggattggaat acgctacctc cccgcttcg     2160 ctagtttggc ttggtttggt gtagtttggc ctggtacaat ccccccgcac acacatgcac    2220
acacgtacac tcacacacac acacaatgcc ccccccccg cacaaacagg tggcctacct     2280
ctccagccgc accggcttcg tgcgactggc cgtgcagcac ggcgcgccgc tggtgccagt    2340
gtgggcgttc ggccagacgc gcgcgtacag ctggttccgg ccggggccgc cgctcgtgcc    2400
cacgtggctc gtggagcgca tctcacgtgc cgccggcgcc gtacccatcg gcatgtttgg    2460
gcagtacggc acgcccatgc cgcaccgcga gcccctcacc attgtggtgg gtcgccccat    2520
cccggtgccg gagctggcgc cgggccagct cgagcccgag cccgaggtgc tggcggcgct    2580
cctcaagcgc ttcacggacg acctgcaggt gtgcgcgcgc gcgtgcgtgt gcctgtgtta    2640
aataaaggaa cgaaagcccg tgtgtgcgt gtgtgtgtgt atgtgtgtgt gtgtgtgtgt     2700
gtgcgtgtgt gtctgtgtgt gtgtgtgtgt gtgtgtgtgt gtgtgtgtgt gtgtgtgtgt    2760
gtgtgtgtgt gtgtgtgtgt gtgtgcgtgc gtgtgtgtct gtgtgtggag gtaggagatg    2820
gggagcacgg gaaggcagtc acgatgagtg gattacggca tgcgctggcg gccagtcgtg    2880
ccacttgtgt cccaaagaga aaggactgct gttttactgc cactgcaatc attgacacac    2940
acgcacacat tcacacacat acacacacgc acacacgcgc acacacacac acacacacat    3000
acctcttctg gcccgcacag gcgctgtacg acaagcacaa ggcgcagttc ggcaagggcg    3060
aggagctggt cataatgtag gcgcggggag gcggggccgg ggaggtgtgg tggatgggtg    3120
gtggtggtgg tggggcgctg gtgccgtggt tgtgtgggga gagggcgcag cgcaggttat    3180
tgcggctgcg ccgtgagagg ttgaccggta aagaagcagg tgtgccgggc accaggagtt    3240
ctaaattctc attttttgtac ggcccactcg gcagaaagct agcgtataga gaggcaaaga    3300
gcggaagcag gtggtgaggg aaagaactga atgctgatgt ctcaagacta aaactgttag    3360
tgctggtgtg gaaggctgga gcccggaggg cacgtgtatg tggcgtgagt gcatttgcca    3420
gatggaaggt ggagtggttg caccggtgcc tcctaatggt ggtgtggaac ctagctgtcg    3480
cgggtgtttg acatgcatgc aaggccgggt gcattaagcc cagtggaccg caagcggttc    3540
gatgcagcaa cacgtgcaag ccaggcttga gctgtcactc acgtcagtgc ccccttcacc    3600
gcacatgctt acaagctcag attcgcttga cagggagttg ctaggcaacg cacagggagc    3660
caacaagtaa aaccgtgcac agtcgcacat agcttgcgct tacacgcata cggtattggc    3720
ggcgtcggcc tcatcggcct gctgacacac catgcatccc cggataccgg cggatgcacc    3780
cacatgacct ccctgccgcc tttcagcgtt tatgtacagc cccgtccttt gcacacgcac    3840
gtggctgcag gccctgtagt cgacacagcc tgacacgcac cccatgcaca tgcgggaggt    3900
cttcgctggg gttcggtccg attcctcctt cccaaacagc cacgcaacac cgtgtccgtg    3960
ccccacctga ttcgccgtgc tgacacgccc gctcctacag tcccc              4005
```

<210> SEQ ID NO 11
<211> LENGTH: 1776
<212> TYPE: DNA
<213> ORGANISM: Chlamydomonas reinhardtii

<400> SEQUENCE: 11

```
ttcaaggagt gctgtatgag tctataaacc agtcaggagc ttgcctcttt cttagggccg       60
```

```
aacgagaatg ccgctcgcaa agctgcgaaa cgtggtgctg gagtacgcgg ccatagccat    120
ctacgtcagc gccatctaca cctcggtggt gctgctgccc tcggcgctcg cgctgttcta    180
cctgtttggg gccaccagcc cctcggcctg gctgctgcta gccgccttcc tggccctcac    240
cttcacgccg ctgcagctga ccaccggtgc gctgtcggag cggttcgtgc agttcagtgt    300
ggcgcgggcg gcggcctact tccccacccg cgtggtggtc acggacccgg aggccttccg    360
cactgaccgc ggctacttgt tcggattctg cccgcactcg gctctgccca tcgcactgcc    420
catcgccttc gccaccacct cgccgctgct gcccaaggag ctgcgcggcc gcacacacgg    480
cttggcgtcg tccgtgtgct tcagcgcgcc catagtgcgg cagctgtact ggtggctggg    540
cgtgcggccc gccacgcggc agagcatcag cggcctgttg cgggcgcgca aggtggcggt    600
gctggtgccg gggggcgtgc aggaggtgct caacatggag cacggcaagg aggtggccta    660
cctctccagc cgcaccggct tcgtgcgact ggccgtgcag cacggcgcgc cgctggtgcc    720
agtgtgggcg ttcggccaga cgcgcgcgta cagctggttc cggccggggc cgccgctcgt    780
gcccacgtgg ctcgtggagc gcatctcacg tgccgccggc gccgtaccca tcggcatgtt    840
tgggcagtac ggcacgccca tgccgcaccg cgagcccctc accattgtgg tgggtcgccc    900
catcccggtg ccggagctgg cgccgggcca gctcgagccc gagcccgagg tgctggcggc    960
gctcctcaag cgcttcacgg acgacctgca ggcgctgtac gacaagcaca aggcgcagtt   1020
cggcaagggc gaggagctgg tcataatgta ggcgcgggga ggcggggccg gggaggtgtg   1080
gtggatgggt ggtggtggtg gtggggcgct ggtgccgtgg ttgtgtgggg agagggcgca   1140
gcgcaggtta ttgcggctgc gccgtgagag gttgaccggt aaagaagcag gtgtgccggg   1200
caccaggagt tctaaattct cattttttgta cggcccactc ggcagaaagc tagcgtatag   1260
agaggcaaag agcggaagca ggtggtgagg gaaagaactg aatgctgatg tctcaagact   1320
aaaactgtta gtgctggtgt ggaaggctgg agcccggagg gcacgtgtat gtggcgtgag   1380
tgcatttgcc agatggaagg tggagtggtt gcaccggtgc ctcctaatgg tggtgtggaa   1440
cctagctgtc gcgggtgttt gacatgcatg caaggccggg tgcattaagc ccagtggacc   1500
gcaagcggtt cgatgcagca acacgtgcaa gccaggcttg agctgtcact cacgtcagtg   1560 ccccccttcac cgcacatgct tacaagctca gattcgcttg acagggagtt gctaggcaac   1620
gcacagggag ccaacaagta aaaccgtgca cagtcgcaca tagcttgcgc ttacacgcat   1680
acggtattgg cggcgtcggc ctcatcggcc tgctgacaca ccatgcatcc ccggataccg   1740
gcggatgcac ccacatgacc tccctgccgc ctttca                             1776
```

<210> SEQ ID NO 12
<211> LENGTH: 327
<212> TYPE: PRT
<213> ORGANISM: Chlamydomonas reinhardtii

<400> SEQUENCE: 12

```
Met Pro Leu Ala Lys Leu Arg Asn Val Val Leu Glu Tyr Ala Ala Ile
1               5                   10                  15

Ala Ile Tyr Val Ser Ala Ile Tyr Thr Ser Val Leu Leu Pro Ser
            20                  25                  30

Ala Leu Ala Leu Phe Tyr Leu Phe Gly Ala Thr Ser Pro Ser Ala Trp
        35                  40                  45

Leu Leu Leu Ala Ala Phe Leu Ala Leu Thr Phe Thr Pro Leu Gln Leu
    50                  55                  60

Thr Thr Gly Ala Leu Ser Glu Arg Phe Val Gln Phe Ser Val Ala Arg
```

Ala Ala Ala Tyr Phe Pro Thr Arg Val Val Thr Asp Pro Glu Ala
 65                  70                  75                  80

Phe Arg Thr Asp Arg Gly Tyr Leu Phe Gly Phe Cys Pro His Ser Ala
             85                  90                  95

Leu Pro Ile Ala Leu Pro Ile Ala Phe Ala Thr Thr Ser Pro Leu Leu
         100                 105                 110

Pro Lys Glu Leu Arg Gly Arg Thr His Gly Leu Ala Ser Ser Val Cys
     115                 120                 125

Phe Ser Ala Pro Ile Val Arg Gln Leu Tyr Trp Trp Leu Gly Val Arg
 130                 135                 140

Pro Ala Thr Arg Gln Ser Ile Ser Gly Leu Leu Arg Ala Arg Lys Val
145                 150                 155                 160

Ala Val Leu Val Pro Gly Gly Val Gln Glu Val Leu Asn Met Glu His
             165                 170                 175

Gly Lys Glu Val Ala Tyr Leu Ser Ser Arg Thr Gly Phe Val Arg Leu
         180                 185                 190

Ala Val Gln His Gly Ala Pro Leu Val Pro Val Trp Ala Phe Gly Gln
     195                 200                 205

Thr Arg Ala Tyr Ser Trp Phe Arg Pro Gly Pro Leu Val Pro Thr
 210                 215                 220

Trp Leu Val Glu Arg Ile Ser Arg Ala Ala Gly Ala Val Pro Ile Gly
225                 230                 235                 240

Met Phe Gly Gln Tyr Gly Thr Pro Met Pro His Arg Glu Pro Leu Thr
             245                 250                 255

Ile Val Val Gly Arg Pro Ile Pro Val Pro Glu Leu Ala Pro Gly Gln
         260                 265                 270

Leu Glu Pro Glu Pro Glu Val Leu Ala Ala Leu Leu Lys Arg Phe Thr
     275                 280                 285

Asp Asp Leu Gln Ala Leu Tyr Asp Lys His Lys Ala Gln Phe Gly Lys
 290                 295                 300

Gly Glu Glu Leu Val Ile Met
305                 310

<210> SEQ ID NO 13
<211> LENGTH: 3263
<212> TYPE: DNA
<213> ORGANISM: Chlamydomonas reinhardtii

<400> SEQUENCE: 13
cctgcagtgg caagggctgc aaggaggcag cggcagcgcc agcacgcgat ggcggcgctg      60
cctgcgccgc ccccataacc gccactactg ccaccatcac cactaccacc gccactgcaa     120
tcaacgccac cacaactgtt gccgccaccg cgcattcccc gcgcccccgc ccgggcccgg     180
gcccgccaaa gctggtggtg atgacccccg gggatccgcc ggtgccgcgg ccgccgccgg     240
gcgtacggca gtacactgac ggccggtcgg cgtcgtacgt actgccgctg ccgtatcgcc     300
tgctggccca ggtgggtgtg acattgacac gttgctgaac ttgctacagc acaaggatgt     360
ccacatgtgt tcggttggcc cacggcgcac gcgcacacgc ttgtcctcgt atcttcctga     420
gtccacgctc cttcgcctct gacagactta cacgcacccc attgtctaag ccggctctcc     480
gagaccaccc tgactagcgc cctccctccc gccgcgattg cagctgactc tgggtttgta     540
cgtgggcttt ccctacatcc tgctgggggtt gttgctgggc acggctgccg gctcgcgcgc     600
cgccgccgcc gccctggctc tgacgctggg cagcctgctg gtgccggccc caccgcacat     660

```
ccggcagggc atgctggact cggcactgtt caggtgggtg gctgcgtgga ggtgggtgga    720
ggttagagcg agatgaccaa ccccatgggc ttcgcttgtg tggaatgcgc cctgcgtgta    780
cggggtatct acctgcttcc gacctcttgc cttgcgcccc cgccccaacc ctgcccgcct    840
cgaaccctgc tgcctcctcg cccctgcccc gccccgcccc gccccaggct gtggcgcgcc    900
tacttcaact acagctacgc ctacgaccaa ctgcccgact tcaaccgccc acacatcttt    960
gtcaacagcc cgcacggcgc cttcccgctg tcgcaggtag gtgggggcgt gtgcgtgtgc   1020
aagtgtgtac atgcagggtc gctggccggg tgcacgtgtg ctatagccta cagggtgacg   1080
gggttagacg gctgccaacc tccaaaacac tcccaggccc tgggggcttc gtgggtccca   1140
ttccattacc cctcccccac agccctcacc acgcgcctca ccccccacctg ccacacccccc  1200 accttccgca cccccacctg ccgcaccccc acagatcctg tgcatctccc tgtccaacat   1260
cgtgtggccg ggcttccccg tgcacagcct ggcggcctcg gtgctgtggt acataccgct   1320
gtggcgccac atgaaggcgg cgctgggggc gcgcccgcc agcgggaca acgcgcgcat     1380 gctgctgagg caccgcgggt gggcgggcgt ggcgtggcgt ggcgtgtaat ggaatgtgca    1440
accgggaggg ctgttgcgtg tgcagtacag tattacacgg tgtcacaata gcagtcagct   1500
ggtgcggtaa tgttgcagtc ggaagaaggt gctataacac agcctactag agctagagta   1560
ggccgacggc gttgcaggcg gcgcgccccc ggggtacaga gcagggtgat cgttcttcca   1620
cgtcactggc ccttgaactg cgtcagcagg tccctattat aaccaacgca gtctataaca   1680
cactcagcgt gccgatgcgc atgcaggtcg gtggcggtgc tggcgggcgg cattgcggag   1740
atgtacacgt catcgccctc ccgcgccgcc gctgccaccg aaccagatga ggctgcggct   1800
gcgggtgggg cgatcgacac gactgaagcc gccggcgcca ccggctcaag cagcaccacc   1860
actagcccgc cgcagccaaa ggagcagcag cgcgatgggg agcagcgcca ggggccgcgc   1920
aaggggctga aggggctgct gaaaggcccg aaggacgatc ccgatccggc ggcggaggag   1980
gagcagggcc tcgggttggc acctgaacgc atcaagctgc tgggccggcg cggcttcgtg   2040
cggctggcgg tggagatggg tgtgcccatt gtacccatat accacatggg caacagcaag   2100
gtgtgtgtgc gtgtgtgtgt gtgtgtgtgt ttgtgcgtgt gtgtatgtgt gtgtgtgtgt   2160
aagtgtgtct ttgtgtgtgt gtgtgtgtgt gtgtgtgtgt gtgtaagtgt gtctttgtgt   2220
gtgtgtgtgt gtgtgagtgt gtgtgtgtgt gtgtgtgtgt gagtgtgtgt gtgtgtaagt   2280
gtgtctttgt gtgtgtgtgt gtgtgtgtgt gtacggcgcg gcagggatgg gtgaagcgcc   2340
ttgagaggga ggaagtaggc gcaggcaggg aagcggccaa gcgggtgcgc gctccagttg   2400
ctccatgcag ttgactgacc tcacggcaca cttggtgagt tggcccttcc taagcgccac   2460
ctgcgccgcc tgtgccctgc agatcctgac cttcgggccg cagtcactgc agcagctgtc   2520
gcgccgcctg cgcatggcgc tgggcgccgt gttcggtgag tcctggcctt cttgccctgc   2580 cccctagtg caatgctagt gggacttttg agcgccccac gccccacgcc tgacgcccct    2640
ctccccttcc attgctcgtt caacccgtgc ttgaatgctt gccgtgcaaa tgcgcgtact   2700
ccacggcggc gccatacgcc caagtgcccg gcgcttcccc cgattgggac ctgttccttc   2760
gggctcggac aagtaccctt ccctccctcc ttccccaccc cagcccttac ccccctcacc   2820
gcctcatgcc ccgcttcaaa caggcgtgtg gggcctgcct gtgccgcgcc cccagccgct   2880
catgatgtgt gtgggcagcc ccattcccgt gccgtacgtg gatccagccg ccgagccgga   2940
gcgcttcgag gccgtggtgg cggcggtgca cgggcaggtg gtggcggcct ttcaggatct   3000
```

```
gtacaacagg taccgcgtgc agtacggctg cggttgggag cgccggccgc tggaggtgtg    3060
ctgagccaac cgccgggtgc ggtggcgtgt gtgcgaggcg tgttgaggtg tatgagcgtg    3120
ggagtggctg attggcacat gcgagtgagg ggttggcggg aagagctcg  aggcgattgg    3180 gcaccgccgc caggtgatga atgcagcttt ggagtttcca aggaactgag gggctggcgg    3240
ctggcggcgg cacggctaaa ggt                                            3263
```

<210> SEQ ID NO 14
<211> LENGTH: 1241
<212> TYPE: DNA
<213> ORGANISM: Chlamydomonas reinhardtii

<400> SEQUENCE: 14

```
atgacccccgc gggatccgcc ggtgccgcgg ccgccgccgg gcgtacggca gtacactgac      60
ggccggtcgg cgtcgtacgt actgccgctg ccgtatcgcc tgctggccca gctgactctg     120
ggtttgtacg tgggctttcc ctacatcctg ctggggttgt tgctgggcac ggctgccggc     180
tcgcgcgccg ccgccgccgc cctggctctg acgctgggca gcctgctggt gccggccccca    240 ccgcacatcc ggcagggcat gctggactcg gcactgttca ggctgtggcg cgcctacttc     300
aactacagct acgcctacga ccaactgccc gacttcaacc gccacacat ctttgtcaac      360 agcccgcacg gcgccttccc gctgtcgcag atcctgtgca tctccctgtc caacatcgtg     420
tggccgggct tccccgtgca cagcctggcg gcctcggtgc tgtggtacat accgctgtgg     480
cgccacatga aggcggcgct gggggccgcg cccgccagcc gggacaacgc gcgcatgctg     540
ctgaggcacc gcgggtcggt ggcggtgctg gcgggcggca ttgcggagat gtacacgtca     600
tcgccctccc gcgccgccgc tgccaccgaa ccagatgagg ctgcggctgc gggtggggcg     660
atcgacacga ctgaagccgc cggcgccacc ggctcaagca gcaccaccac tagcccgccg     720
cagccaaagg agcagcagcg cgatggggag cagcgccagg ggccgcgcaa ggggctgaag     780
gggctgctga aggcccgaa ggacgatccc gatccggcgg cggaggagga gcagggcctc      840
gggttggcac ctgaacgcat caagctgctg gccggcgcg  gcttcgtgcg gctggcggtg     900
gagatgggtg tgcccattgt acccatatac cacatgggca cagcaagat  cctgaccttc     960 gggccgcagt cactgcagca gctgtcgcgc cgcctgcgca tggcgctggg cgccgtgttc    1020
ggcgtgtggg gcctgcctgt gccgcgcccc cagccgctca tgatgtgtgt gggcagcccc    1080
attcccgtgc cgtacgtgga tccagccgcc gagccggagc gcttcgaggc cgtggtggcg    1140
gcggtgcacg gcaggtggt  ggcggccttt caggatctgt acaacaggta ccgcgtgcag    1200
tacggctgcg gttgggagcg ccggccgctg gaggtgtgct g                        1241
```

<210> SEQ ID NO 15
<211> LENGTH: 413
<212> TYPE: PRT
<213> ORGANISM: Chlamydomonas reinhardtii

<400> SEQUENCE: 15

```
Met Thr Pro Arg Asp Pro Pro Val Pro Arg Pro Pro Gly Val Arg
1               5                   10                  15

Gln Tyr Thr Asp Gly Arg Ser Ala Ser Tyr Val Leu Pro Leu Pro Tyr
            20                  25                  30

Arg Leu Leu Ala Gln Leu Thr Leu Gly Leu Tyr Val Gly Phe Pro Tyr
        35                  40                  45

Ile Leu Leu Gly Leu Leu Leu Gly Thr Ala Ala Gly Ser Arg Ala Ala
    50                  55                  60
```

```
Ala Ala Ala Leu Ala Leu Thr Leu Gly Ser Leu Leu Val Pro Ala Pro
 65              70              75              80

Pro His Ile Arg Gln Gly Met Leu Asp Ser Ala Leu Phe Arg Leu Trp
             85              90              95

Arg Ala Tyr Phe Asn Tyr Ser Tyr Ala Tyr Asp Gln Leu Pro Asp Phe
            100             105             110

Asn Arg Pro His Ile Phe Val Asn Ser Pro His Gly Ala Phe Pro Leu
            115             120             125

Ser Gln Ile Leu Cys Ile Ser Leu Ser Asn Ile Val Trp Pro Gly Phe
130             135             140

Pro Val His Ser Leu Ala Ala Ser Val Leu Trp Tyr Ile Pro Leu Trp
145             150             155             160

Arg His Met Lys Ala Ala Leu Gly Ala Ala Pro Ala Ser Arg Asp Asn
            165             170             175

Ala Arg Met Leu Leu Arg His Arg Gly Ser Val Ala Val Leu Ala Gly
            180             185             190

Gly Ile Ala Glu Met Tyr Thr Ser Ser Pro Ser Arg Ala Ala Ala Ala
        195             200             205

Thr Glu Pro Asp Glu Ala Ala Ala Ala Gly Gly Ala Ile Asp Thr Thr
210             215             220

Glu Ala Ala Gly Ala Thr Gly Ser Ser Ser Thr Thr Thr Ser Pro Pro
225             230             235             240

Gln Pro Lys Glu Gln Gln Arg Asp Gly Glu Gln Arg Gln Gly Pro Arg
            245             250             255

Lys Gly Leu Lys Gly Leu Leu Lys Gly Pro Lys Asp Asp Pro Asp Pro
            260             265             270

Ala Ala Glu Glu Glu Gln Gly Leu Gly Leu Ala Pro Glu Arg Ile Lys
            275             280             285

Leu Leu Gly Arg Arg Gly Phe Val Arg Leu Ala Val Glu Met Gly Val
    290             295             300

Pro Ile Val Pro Ile Tyr His Met Gly Asn Ser Lys Ile Leu Thr Phe
305             310             315             320

Gly Pro Gln Ser Leu Gln Leu Ser Arg Arg Leu Arg Met Ala Leu
            325             330             335

Gly Ala Val Phe Gly Val Trp Gly Leu Pro Val Pro Arg Pro Gln Pro
            340             345             350

Leu Met Met Cys Val Gly Ser Pro Ile Pro Val Pro Tyr Val Asp Pro
            355             360             365

Ala Ala Glu Pro Glu Arg Phe Glu Ala Val Val Ala Ala Val His Gly
            370             375             380

Gln Val Val Ala Ala Phe Gln Asp Leu Tyr Asn Arg Tyr Arg Val Gln
385             390             395             400

Tyr Gly Cys Gly Trp Glu Arg Arg Pro Leu Glu Val Cys
            405             410
```